US012697385B2

(12) United States Patent
Inamdar et al.

(10) Patent No.: US 12,697,385 B2
(45) Date of Patent: *Aug. 4, 2026

(54) COMBINATION THERAPY FOR CANCER WITH ANTI-B7-H4 ANTIBODIES AND ANTI-PD-1 ANTIBODIES

(71) Applicant: FIVE PRIME THERAPEUTICS, INC., Thousand Oaks, CA (US)

(72) Inventors: Sandeep P. Inamdar, South San Francisco, CA (US); Helen L. Collins, South San Francisco, CA (US); Hong Xiang, South San Francisco, CA (US); Xiang Zhang, South San Francisco, CA (US); Neyssa Marina, South San Francisco, CA (US)

(73) Assignee: FIVE PRIME THERAPEUTICS, INC., Thousand Oaks, CA (US)

( * ) Notice: Subject to any disclaimer, the term of this patent is extended or adjusted under 35 U.S.C. 154(b) by 1346 days.

This patent is subject to a terminal disclaimer.

(21) Appl. No.: 17/224,865

(22) Filed: Apr. 7, 2021

(65) Prior Publication Data

US 2021/0332137 A1 Oct. 28, 2021

Related U.S. Application Data

(63) Continuation of application No. PCT/US2019/056210, filed on Oct. 15, 2019.

(60) Provisional application No. 62/854,494, filed on May 30, 2019, provisional application No. 62/802,091, filed on Feb. 6, 2019, provisional application No. 62/745,464, filed on Oct. 15, 2018.

(51) Int. Cl.
| | |
|---|---|
| *A61P 35/00* | (2006.01) |
| *A61K 39/395* | (2006.01) |
| *A61K 39/00* | (2006.01) |
| *C07K 16/28* | (2006.01) |

(52) U.S. Cl.
CPC .......... *A61K 39/3955* (2013.01); *A61P 35/00* (2018.01); *A61K 39/00* (2013.01); *A61K 2039/505* (2013.01); *A61K 2039/507* (2013.01); *A61K 2039/545* (2013.01); *C07K 16/2818* (2013.01); *C07K 16/2827* (2013.01); *C07K 2317/24* (2013.01); *C07K 2317/41* (2013.01); *C07K 2317/51* (2013.01); *C07K 2317/515* (2013.01); *C07K 2317/565* (2013.01); *C07K 2317/76* (2013.01)

(58) Field of Classification Search
CPC . A61K 39/3955; A61P 35/00; C07K 26/2827; C07K 16/2818
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,472,509 A | 9/1984 | Gansow et al. |
| 4,938,948 A | 7/1990 | Ring et al. |
| 5,122,464 A | 6/1992 | Wilson et al. |
| 5,196,066 A | 3/1993 | Kusuda et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,516,637 A | 5/1996 | Huang et al. |
| 5,571,698 A | 11/1996 | Ladner et al. |
| 5,580,717 A | 12/1996 | Dower et al. |
| 5,585,097 A | 12/1996 | Bolt et al. |
| 5,624,821 A | 4/1997 | Winter et al. |
| 5,648,260 A | 7/1997 | Winter et al. |
| 5,658,727 A | 8/1997 | Barbas et al. |
| 5,672,694 A | 9/1997 | Campbell et al. |
| 5,677,425 A | 10/1997 | Bodmer et al. |
| 5,693,780 A | 12/1997 | Newman et al. |
| 5,698,426 A | 12/1997 | Huse |
| 5,733,743 A | 3/1998 | Johnson et al. |
| 5,750,753 A | 5/1998 | Kimae et al. |
| 5,780,225 A | 7/1998 | Wigler et al. |
| 5,807,715 A | 9/1998 | Morrison et al. |
| 5,821,047 A | 10/1998 | Garrard et al. |
| 5,869,046 A | 2/1999 | Presta et al. |
| 5,965,726 A | 10/1999 | Pavlakis et al. |

(Continued)

FOREIGN PATENT DOCUMENTS

| | | |
|---|---|---|
| CN | 101951959 A | 1/2011 |
| CN | 104945508 A | 9/2015 |

(Continued)

OTHER PUBLICATIONS

Freshwater et al, 2017. Journal for Immunotherapy of Cancer: 5:43; 9 pages as printed.*
Abadi et al., Host B7x promotes pulmonary metastasis of breast cancer, J. Immun., 190(7):3806-3814 (2013).
Abdiche et al., Assessing kinetic and epitopic diversity across orthogonal monoclonal antibody generation platforms, mAbs, 8:264-277 (2016).
Abdiche et al., Exploring blocking assays using octet, prote on, and biacore biosensors, Analytical Biochem., 386(2):172-180 (2009).

(Continued)

*Primary Examiner* — Zachary C Howard
(74) *Attorney, Agent, or Firm* — MARSHALL, GERSTEIN & BORUN LLP

(57) ABSTRACT

The present disclosure provides methods of administering antibodies and antigen-binding fragments thereof that specifically bind to human B7-H4 to a subject in need thereof, for example, a cancer patient, in combination with a PD-1/PD-L1 antagonist, such as an anti-PD-1 antibody.

41 Claims, 3 Drawing Sheets

Specification includes a Sequence Listing.

(56)                    References Cited

U.S. PATENT DOCUMENTS 5,969,108  A    10/1999   Mccafferty et al.
    6,121,022  A     9/2000   Presta et al.
    6,165,745  A    12/2000   Ward et al.
    6,174,666  B1    1/2001   Pavlakis et al.
    6,194,551  B1    2/2001   Idusogie et al.
    6,277,022  B1    8/2001   Melin
    6,291,664  B1    9/2001   Pavlakis et al.
    6,414,132  B1    7/2002   Pavlakis et al.
    6,602,684  B1    8/2003   Umana et al.
    6,737,056  B1    5/2004   Presta
    6,794,498  B2    9/2004   Pavlakis et al.
    6,891,030  B2    5/2005   Chen
    6,946,292  B2    9/2005   Kanda et al.
    7,214,775  B2    5/2007   Hanai et al.
    7,304,149  B2   12/2007   Murphy et al.
    7,504,256  B1    3/2009   Ogawa et al.
    7,619,068  B2   11/2009   Pilkington et al.
    7,622,565  B2   11/2009   Chen
    7,658,921  B2    2/2010   Dall et al.
    7,687,061  B2    3/2010   Hanai et al.
    7,709,226  B2    5/2010   Foote
    7,875,702  B2    1/2011   Chen
    7,888,477  B2    2/2011   Bangur et al.
    7,931,896  B2    4/2011   Chen
    7,964,195  B2    6/2011   Papkoff et al.
    8,129,347  B2    3/2012   Chen
    8,182,813  B2    5/2012   Brasel et al.
    8,206,715  B2    6/2012   Wong et al.
    8,236,767  B2    8/2012   Chen
    8,263,079  B2    9/2012   Doody et al.
    8,323,645  B2   12/2012   Veiby et al.
    8,444,971  B2    5/2013   Papkoff et al.
    8,513,199  B2    8/2013   Brasel et al.
    8,591,886  B2   11/2013   Ponath et al.
    8,609,816  B2   12/2013   Korman et al.
    8,652,465  B2    2/2014   Freeman et al.
    8,703,916  B2    4/2014   Chen
    8,759,490  B2    6/2014   Veiby et al.
    8,906,369  B2   12/2014   Papkoff et al.
    9,005,616  B2    4/2015   Langermann et al.
    9,011,853  B2    4/2015   Langermann et al.
    9,121,853  B2    9/2015   Kwon et al.
    9,221,910  B2   12/2015   Fertig et al.
    9,279,008  B2    3/2016   Scholler et al.
    9,296,822  B2    3/2016   Korman et al.
    9,421,277  B2    8/2016   Veiby et al.
    9,422,351  B2    8/2016   Scholler et al.
    9,447,186  B2    9/2016   Zang et al.
    9,555,124  B2    1/2017   Chen
    9,562,099  B2    2/2017   Leong et al.
    9,574,000  B2    2/2017   Langermann et al.
    9,676,854  B2    6/2017   Liu et al.
    9,926,378  B2    3/2018   Veiby et al.
    9,957,312  B2    5/2018   Langermann et al.
   10,059,768  B2    8/2018   Leong et al.
   11,306,144  B2    4/2022   Kaplan et al.
   11,814,431  B2 * 11/2023   Kaplan ........... G01N 33/57492
 2003/0055224  A1    3/2003   Gao et al.
 2003/0060612  A1    3/2003   Goddard et al.
 2003/0165504  A1    9/2003   Retter et al.
 2003/0181692  A1    9/2003   Ni et al.
 2003/0208058  A1   11/2003   Fiscella et al.
 2004/0014194  A1    1/2004   Beyer et al.
 2004/0126807  A1    7/2004   Goddard et al.
 2005/0163772  A1    7/2005   Dong et al.
 2006/0088523  A1    4/2006   Andya et al.
 2006/0223077  A1   10/2006   Ni et al.
 2006/0253928  A1   11/2006   Bakker et al.
 2007/0036783  A1    2/2007   Humeau et al.
 2007/0178551  A1    8/2007   Gerngross
 2007/0218032  A1    9/2007   Kwon et al.
 2007/0248600  A1   10/2007   Hansen et al.
 2008/0050370  A1    2/2008   Glaser et al.
 2008/0060092  A1    3/2008   Dickey et al.
 2008/0206235  A1    8/2008   Chen 2009/0005301  A1    1/2009   Ni et al.
 2009/0118175  A1    5/2009   Macina
 2009/0176317  A1    7/2009   Kwon et al.
 2009/0226530  A1    9/2009   Lassner et al.
 2011/0020325  A1    1/2011   Kwon et al.
 2011/0085970  A1    4/2011   Terrett et al.
 2012/0014947  A1    1/2012   Fu
 2013/0078234  A1    3/2013   Takahashi et al.
 2014/0037551  A1    2/2014   Zang et al.
 2014/0294861  A1   10/2014   Scholler et al.
 2014/0322129  A1   10/2014   Leong et al.
 2014/0335541  A1   11/2014   Kwon et al.
 2014/0356364  A1   12/2014   Liu et al.
 2014/0364585  A1   12/2014   Zhang et al.
 2015/0315275  A1   11/2015   Liu et al.
 2016/0017040  A1    1/2016   Leong et al.
 2016/0146806  A1    5/2016   Langermann et al.
 2016/0159910  A1    6/2016   Leong et al.
 2016/0185870  A1    6/2016   Van et al.
 2016/0304581  A1   10/2016   Zang et al.
 2016/0304607  A1   10/2016   Sadineni et al.
 2017/0015758  A1    1/2017   Hammond et al.
 2017/0029525  A1    2/2017   Zang et al.
 2017/0044259  A1    2/2017   Tipton et al.
 2017/0044268  A1    2/2017   Gurney et al.
 2017/0143827  A1    5/2017   Sadineni et al.
 2017/0158771  A1    6/2017   Glennie et al.
 2017/0204185  A1    7/2017   Chen
 2017/0233808  A1    8/2017   Haining et al.
 2017/0334999  A1 * 11/2017   Sathyanarayanan ........................
                                             C07K 16/3015
 2018/0106862  A1    4/2018   Whetsel
 2018/0106864  A1    4/2018   Moeneclaey
 2018/0118831  A1    5/2018   Epstein et al.
 2018/0186878  A1    7/2018   Rosenthal
 2019/0085080  A1    3/2019   Kaplan et al.
 2020/0081497  A1    3/2020   Hung et al.
 2020/0255528  A1    8/2020   Kaplan et al.
 2021/0070861  A1    3/2021   Quan et al.
 2021/0070862  A1    3/2021   Inamdar et al.
 2021/0079096  A1    3/2021   Kaplan et al.
 2024/0043542  A1    2/2024   Kaplan et al.

FOREIGN PATENT DOCUMENTS

CN         106804108   A      6/2017
   CN         107299085   A     10/2017
   CN         107405401   A     11/2017
   CN         111094352   A      5/2020
   CN         111868089   A     10/2020
   CN         111971308   A     11/2020
   EP           1331266   A1     7/2003
   SG            162030   A1     7/2010
   WO        1986/05807   A1    10/1986
   WO        1989/01036   A1     2/1989
   WO        1990/02809   A1     3/1990
   WO        1991/10737   A1     7/1991
   WO        1992/01047   A1     1/1992
   WO        1992/18619   A1    10/1992
   WO        1993/11236   A1     6/1993
   WO        1994/29351   A2    12/1994
   WO        1995/15982   A2     6/1995
   WO        1995/20401   A1     8/1995
   WO        1997/13844   A1     4/1997
   WO        1997/34631   A1     9/1997
   WO        1998/23289   A1     6/1998
   WO        1999/54342   A1    10/1999
   WO        2000/36107   A2     6/2000
   WO        2000/42072   A2     7/2000
   WO        2000/61739   A1    10/2000
   WO        2001/29246   A1     4/2001
   WO        2001/40269   A2     6/2001
   WO        2001/62891   A2     8/2001
   WO        2002/02587   A1     1/2002
   WO        2002/06317   A2     1/2002
   WO        2002/10187   A1     2/2002
   WO        2002/16581   A2     2/2002
   WO        2002/30954   A1     4/2002
   WO        2002/31140   A1     4/2002

(56)                    References Cited

FOREIGN PATENT DOCUMENTS

| WO | 2002/60919 | A2 | 8/2002 |
|----|------------|----|--------|
| WO | 2002/71928 | A2 | 9/2002 |
| WO | 2003/04989 | A2 | 1/2003 |
| WO | 2002/62203 | A3 | 2/2003 |
| WO | 2003/76579 | A2 | 9/2003 |
| WO | 2003/11878 | A3 | 11/2003 |
| WO | 2003/97802 | A2 | 11/2003 |
| WO | 2003/97803 | A2 | 11/2003 |
| WO | 2003/104399 | A2 | 12/2003 |
| WO | 2003/104438 | A2 | 12/2003 |
| WO | 2004/000221 | A2 | 12/2003 |
| WO | 2004/058167 | A2 | 7/2004 |
| WO | 2004/065540 | A2 | 8/2004 |
| WO | 2004/101756 | A2 | 11/2004 |
| WO | 2004/113500 | A2 | 12/2004 |
| WO | 2005/035724 | A2 | 4/2005 |
| WO | 2005/051990 | A2 | 6/2005 |
| WO | 2005/052121 | A2 | 6/2005 |
| WO | 2005/062788 | A2 | 7/2005 |
| WO | 2003/101400 | A3 | 9/2005 |
| WO | 2006/053110 | A2 | 5/2006 |
| WO | 2006/074418 | A2 | 7/2006 |
| WO | 2006/098887 | A2 | 9/2006 |
| WO | 2006/104677 | A2 | 10/2006 |
| WO | 2006/105021 | A2 | 10/2006 |
| WO | 2006/121991 | A2 | 11/2006 |
| WO | 2006/133396 | A2 | 12/2006 |
| WO | 2007/001459 | A2 | 1/2007 |
| WO | 2007/005874 | A2 | 1/2007 |
| WO | 2007/039818 | A2 | 4/2007 |
| WO | 2007/067991 | A2 | 6/2007 |
| WO | 2007/082154 | A2 | 7/2007 |
| WO | 2008/067283 | A2 | 6/2008 |
| WO | 2008/071447 | A2 | 6/2008 |
| WO | 2008/083228 | A2 | 7/2008 |
| WO | 2008/083239 | A2 | 7/2008 |
| WO | 2008/154333 | A2 | 12/2008 |
| WO | WO-2008/156712 | A1 | 12/2008 |
| WO | 2009/009116 | | 1/2009 |
| WO | 2009/036379 | A2 | 3/2009 |
| WO | 2009/073533 | A2 | 6/2009 |
| WO | 2010/105256 | A1 | 9/2010 |
| WO | 2011/020024 | A2 | 2/2011 |
| WO | 2011/028683 | | 3/2011 |
| WO | 2012/009568 | A2 | 1/2012 |
| WO | 2012/130831 | A1 | 10/2012 |
| WO | 2012/145493 | A1 | 10/2012 |
| WO | 2013/025779 | A1 | 2/2013 |
| WO | 2013/067492 | A1 | 5/2013 |
| WO | 2013/079174 | A1 | 6/2013 |
| WO | 2014/100439 | A2 | 6/2014 |
| WO | 2014/100483 | A1 | 6/2014 |
| WO | 2014/100823 | A1 | 6/2014 |
| WO | 2014/159835 | A1 | 10/2014 |
| WO | 2014/194293 | A1 | 12/2014 |
| WO | 2015/017600 | A1 | 2/2015 |
| WO | 2015/031667 | A2 | 3/2015 |
| WO | 2015/069770 | A1 | 5/2015 |
| WO | 2016/040724 | A1 | 3/2016 |
| WO | 2016/070001 | A1 | 5/2016 |
| WO | WO-2016137985 | A1 | 9/2016 |
| WO | 2016/168771 | A2 | 10/2016 |
| WO | 2016/197204 | A1 | 12/2016 |
| WO | 2017/011580 | A2 | 1/2017 |
| WO | 2017/015623 | A2 | 1/2017 |
| WO | 2017/019846 | A1 | 2/2017 |
| WO | 2017/048878 | A1 | 3/2017 |
| WO | 2017/058754 | A1 | 4/2017 |
| WO | 2017/079117 | A1 | 5/2017 |
| WO | 2017/106656 | A1 | 6/2017 |
| WO | 2017/129790 | A1 | 8/2017 |
| WO | 2017/147368 | A1 | 8/2017 |
| WO | 2017/149150 | A1 | 9/2017 |
| WO | 2017/201502 | A1 | 11/2017 |
| WO | 2018/049474 | A1 | 3/2018 |
| WO | 2018/075978 | A1 | 4/2018 |
| WO | 2018/078145 | A1 | 5/2018 |
| WO | 2018/098363 | A2 | 5/2018 |
| WO | 2018/106862 | A1 | 6/2018 |
| WO | 2018/106864 | A1 | 6/2018 |
| WO | 2019/040780 | A1 | 2/2019 |
| WO | 2019/165075 | A1 | 8/2019 |
| WO | 2019/165077 | A1 | 8/2019 |
| WO | 2019/169212 | A1 | 9/2019 |
| WO | 2020/081497 | A1 | 4/2020 |

OTHER PUBLICATIONS

Al-Lazikani et al., Standard conformations for the canonical structures of Immunoglobulins, J. Mol. Biol., 273:927-948 (1997).

Ames et al., Conversion of murine fabs isolated from a combinatorial phage display library to full length immunoglobulins, J. Immunol. Methods, 184(2):177-186 (1995).

Anderson et al., Assessing lead time of selected ovarian cancer biomarkers: a nested case-control study, J. Natl. Cancer Institute, 102(1):26-38 (2010).

Arigami et al., Expression of B7-H4 in blood of patients with gastric cancer predicts tumor progression and prognosis, J. Surgical Oncology, 102:748-752 (2010).

Arnold et al., The impact of glycosylation on the biological function and structure of human Immunoglobulins, Ann. Rev. Immun., 25:21-50 (2007).

ATCC Catalog No. PTA-5180—Mouse hybridoma: Ovr110 A57.1, 2 pages.

Ausubel et al., Current protocols in molecular biology, Greene publishing and wiley interscience, New York, TOC, 7 (1987).

Awadallah et al., Detection of B7-H4 and p53 in pancreatic cancer: potential role as a cytological diagnostic adjunct, Pancreas, 36(2):200-6 (2008).

Azuma et al., Potential role of decoy b7-h4 in the pathogenesis of rheumatoid arthritis: a mouse model informed by clinical data, PLOS Medicine, 6(10):1-15, e1000166, Public Library of Science, United States (2009).

Balwit et al., The iSBTc/SITC primer on tumor immunology and biological therapy of cancer: a summary of the 2010 program, J. Translational Medicine, 9:18 (2011).

Barach et al., Tcell conihibition in prostate cancer: new immune evasion pathways and emerging therapeutics, Trends Mol. Med., 17(1):47-55 (2011).

Boyd et al., Deep sequencing and human antibody repertoire analysis, Current Opinion in Immunology, 40:103-109 (2016).

Bregar et al., Characterization of immune regulatory molecules b7-h4 and pd-l1 in low and high grade endometrial tumors, Gynecologic Oncology, 145(3):446-452 (2017).

Bricogne, Bayesian statistical viewpoint on structure determination: basic concepts and examples, Meth. Enzymol., 276:361-423 (1997).

Bricogne, Direct phase determination by entropy maximization and likelihood ranking: status report and perspectives, Acta. Crystallogr D. Biol. Crystallogr., D49(Pt 1):37-60 (1993).

Brinkman et al., Phage display of disulfide-stabilized fv fragments, J. Immunol. Methods, 182:41-50 (1995).

Burton et al., Human antibodies from combinatorial libraries, Advances in Imnnunology, 57:191-280 (1994).

Carreno et al., Therapeutic opportunities in the b7/cd28 family of ligands and receptors, Current Opinion in Pharmacology, 5(4):424-430 (2005).

Champe et al., Monoclonal antibodies that block the activity of leukocyte function-associated antigen 1 recognize three discrete epitopes in the inserted domain of CD11a, J. Biol. Chem., 270:1388-1394 (1995).

Chayen, The role of oil in macromolecular crystallization, Structure, 5(10):1269-1274 (1997).

Chen et al., Analysis of B7-H4 expression in metastatic pleural adenocarcinoma and therapeutic potential of its antagonists, BMC Cancer, 17(1):652 (2017).

Chen et al., B7-H4 Expression associates with cancer progression and predicts patient's survival in human esophageal squamous cell carcinoma, Cancer Immunology Immunotherapy, 60(7):1047-1055 (2011).

(56)         References Cited

OTHER PUBLICATIONS

Chen et al., Increase of circulating B7-H4-expressing CD68+ macrophage correlated with clinical stage of lung carcinomas, J. Immunotherapy, 35(4):354-358 (2012).

Chen et al., Increased B7-H4 Expression during esophageal squamous cell carcinogenesis is associated with IL-6/STAT3 signaling pathway activation in mice, Oncology Letters, 13(4):2207-2215 (2017).

Chen et al., Induced expression of B7-H4 on the surface of lung cancer cell by the tumor-associated macrophages: a potential mechanism of immune escape, Cancer Letters, 317(1):99-105 (2012).

Chen et al., Nuclear localization of B7-H4 in pulmonary adenocarcinomas presenting as a solitary pulmonary nodule, Oncotarget, 7(36):58563-58568 (2016).

Chen et al., Overexpression of B7-H4 in Tumor infiltrated dendritic cells, J. Immun. Immunochemistry, 32(4):353-364 (2011).

Chen et al., The coexpression and clinical significance of costimulatory molecules B7-H1, B7-H3, and B7-H4 in human pancreatic cancer, Onco. Targets and Therapy, 7:1465-1472 (2014).

Cheung et al., Epitope-specific antibody response to the surface antigen of duck hepatitis b virus in infected ducks, Virology, 176(2):546-552 (1990).

Chinnadurai et al., B7-H4 Mediates inhibition of T cell responses by activated murine hepatic stellate cells, Hepatology, 52(6):2177-2185 (2010).

Choi et al., Genomic organization and expression analysis of B7-H4, an immune inhibitory molecule of the B7 family, J. Immunology, 171(9):4650-4654 (2003).

Chothia et al., Canonical structures for the hypervariable regions of immunoglobulins, J. Moi. Biol., 196(4):901-917 (1987).

Chothia et al., Structural repertoire of the human VH segments, J. Mol. Biol., 227(3):799-817 (1992).

Chumsae et al., Discovery of a chemical modification by citric acid in a recombinant monoclonal antibody, Analytical Chemistry, 86(18):8932-8936 (2014).

Clackson et al., Making antibody fragments using phage display libraries, Nature, 352:624-628 (1991).

Coales et al., Epitope mapping by amide hydrogen/deuterium exchange coupled with immobilization of antibody, on-line proteolysis, liquid chromatography and mass spectrometry, Rapid Commun. Mass Spectrom., 23(5):639-647 (2009).

Cockett et al., High level expression of tissue inhibitor of metalloproteinases in chinese hamster ovary cells using glutamine synthetase gene amplification, Bio/Technology, 8(7):662-667 (1990).

Conroy et al., Antibodies: From novel repertoires to defining and refining the structure of biologically important targets, Methods, 116:12-22 (2017).

Cui et al., B7-H4 is predictive of poor prognosis in patients with gastric cancer, Med. Sci. Monitor, 22:4233-4237 (2016).

Cunningham et al., High-resolution epitope mapping of hGH-receptor interactions by alanine-scanning mutagenesis, Science, 244:1081-1085 (1989).

D'Aria et al., Abstract# 1601: B7-H4 (DD-O110) is overexpressed in endocervicai adenorcarcinoma in situ and invasive adenocarcinoma, Cancer Research, retrieved from https//cacerres.aacrjournals.org/content/59/9_Supplement/1601, last visited Apr. 30, 2020, 4 (2009).

Dall'Acqua et al., Properties of human IgG1s engineered for enhanced binding to the neonatal Fe receptor (FcRn), J. Biol. Chem., 281(33):23514-23524 (2006).

Damschroder et al., Analysis of human and primate CD2 molecules by protein sequence and epitope mapping with anti-human CD2 antibodies, Molecular Immunology, 41:985-1000 (2004).

Dangaj et al., Blocking the B7-H4 pathway with novel recombinant antibodies enhances T cell-mediated antitumor responses, Oncolmmunology, 2:8 e25913 (2013).

Dangaj et al., novel recombinant human b7-h4 antibodies overcome tumoral immune escape to potentiate t-cell antitumor responses, Cancer Research, 73(15):4820-4829 (2013).

Davies et al., Expression of GnTIII in a recombinant anti-CD20 CHO production cell line: Expression of antibodies with altered glycoforms leads to an increase in ADCC through higher affinity for FC gamma RIII, Biotechnol. Bioeng., 74(4):288-294 (2001).

Driessens et al., Costimulatory and coinhibitory receptors in anti-tumor immunity, Immunol. Rev., 229(1):126-144 (2009).

Li et al., Progress in molecular typing of triple negative breast cancer, Journal of New Medicine, No. 2 (2018).

Wang et al., B7-H4 Overexpression contributes to poor prognosis and drug-resistance in triple-negative breast cancer, Cancer Cell International, 18:100 (2018).

Wang et al., Could B7-H4 serve as a target to activate anti-cancer immunity? International Immunopharmacology, 38: 97-103 (2016).

Wang et al., Roles of coinhibitory molecules B7-H3 and B7-H4 in esophageal squamous cell carcinoma, Tumour Biology, Online Publication, Springer Publishing, United States 1-11 (2015).

Wilcox et al., CD14+ hla-DR-/Lo Myeloid-derived suppressor cens express immunosuppressive B7-H family members and are depleted following taxane-based chemotherapy in melanoma, Blood, 114(22):464, 2020, 6 (2009).

Wu et al., Abstract 547: Development of antigen-targeted vaccines and immune checkpoint inhibitors for cancer therapy, immune response modifiers: Cancer Vaccines, 1 (No Date).

Xu et al., Addressing polyspecificity of antibodies selected from an in vitro yeast presentation system: a FAGS-based, high-throughput selection and analytical tool, PEDS, (26)10: 663-70 (2013).

Xu et al., B7-H3 and B7-H4 Are independent predictors of a poor prognosis in patients with pancreatic cancer, Oncol. Letters, 11(3):1841-1846 (2016).

Yamane-Ohnuki et al., Establishment of FUT8 knockout chinese hamster ovary cells: an ideal host cell line for producing completely defucosylated antibodies with enhanced antibody-dependent cellular cytotoxicity, Wiley Interscience, Advance Publication Online, 1-9 (2004).

Ye et al., Does B7-H4 expression correlate with clinicopathologic characteristics and survival in ovarian cancer?: a systematic review and prisma-compliant meta-analysis, Medicine, 97(32):e11821 (2018).

Zang et al., B7-H3 and B7x Are highly expressed in human prostate cancer and associated with disease spread and poor outcome, Proc. Natl. Acad. Sci., 104(49):19458-19463 (2007).

Zang et al., B7x: a Widely expressed B7 family member that inhibits T cell activation, Proc. Natl. Acad. Sci., 100(18):10388-10392 (2003).

Zhang et al., B7-H4 Promotes tumor growth and metastatic progression in lung cancer by impacting cell proliferation and survival, Oncotarget, 8(12):18861-18871 (2017).

Zhang et al., Circulating B7-H4 in serum predicts prognosis in patients with hepatocellular carcinoma, Genetics and Molecular Research, 14(4):13041-13048 (2015).

Zhang et al., Preparation and characterization of monoclonal antibody against human B7-H4 molecule, Monoclonal Antibodies in Immunodiagnosis and Immunotherapy, 33(4):270-274 (2014).

Zhang et al., The costimulatory molecule B7-H4 promote tumor progression and cell proliferation through translocating into nucleus, Oncogene, 32(46): 5347-5358 (2013).

Zhou et al., Silencing of B7-H4 suppresses the tumorigenicity of the Mgc-803 human gastric cancer cell line and promotes cell apoptosis via the mitochondrial signaling pathway, Int. J. Oncology, 52(4):1267-1276 (2018).

Zhou et al., Structural repertoire of HIV-1-neutralizing antibodies targeting the CD4 supersite in 14 donors, Cell, 161:1280-1292 (2015).

Zhu et al., B7-H4 Expression is associated with cancer progression and predicts patient survival in human thyroid cancer, Asian Pacific J. Cancer Prevention, 14(5):3011-3015 (2013).

Zou, Immunosuppressive networks in the tumour environment and their therapeutic relevance, Nature Reviews, 5:263-274 (Apr. 2005, e-pub. Mar. 18, 2015).

Arosio, P. et al, Aggregation mechanism of an IgG2 and two IgG1 monoclonal antibodies at low pH: from oligomers to larger aggregates, Pharm Res., 30(3): 641-54 (2013).

Caldas et al. Humanization of the anti-CD18 antibody 6.7: an unexpected effect of a framework residue in binding to antigen, Mol. Immunol., 39(15):941-952 (2003).

(56) References Cited

OTHER PUBLICATIONS

Casadevall et al., Immunoglobulin isotype influences affinity and specificity, Proceedings of the National Academy of Sciences, 109(31):12272-12273 (2012).

Daugherty et al., "Chapter 8: Formulation and delivery issues for monoclonal antibody therapeutics", Curr. Tren. in Mon. Ant. Dev. Man., 103-129 (2010).

Du et al., Molecular Basis of Recognition of Human Osteopontin by 23C3, a Potential Therapeutic Antibody for Treatment of Rheumatoid Arthritis, Journal of Molecular Biology, 382(4):835-842 (2008).

Hyungjun J. et al., Structure and Cancer Immunotherapy of the B7 Family Member B7x, Cell Reports, Elesvier Ind., 9(3): 1089-1098 (2014).

Kunik et al., Structural Consensus among Antibodies Defines the Antigen Binding Site, PLOS Computational Biology, 8(2):e1002388 (2012).

Pozsgai, E., et al., β-Sarcoglycan Gene Transfer Leads to Functional Improvement in a Model of LGMD2E (S61.002), Neurology, 82(10):1-3 (2014).

Stanton et al., Clinical significance of tumor-infiltrating lymphocytes in breast cancer, J. Immunotherapy Cancer, 4:59 (2016).

Shimazaki, Japanese Journal of Zootechnical Science, 61(7): 655-660 (1990).

Wang et al., Antibody Structure, Instability, and Formulation, Journal of Pharmaceutical Sciences, 96(1):1-26 (2007).

Presta et al., Engineering therapeutic antibodies for improved function, Biochemical Society Transactions, 30(4):487-490 (2002).

Qian et al., B7-H4 Expression in various tumors determined using a novel developed monoclonal antibody, Clinical and Experimental Medicine, 11(3):163-170 (2011).

Qian et al., Development of a novel monoclonal antibody to B7-H4: characterization and biological activity, European Journal of Medical Research, 16(7):295-302 (2011).

Rabinovich et al., Immunosuppressive strategies that are mediated by tumor cells, Annu. Rev. Immunol., 25:267-296 (2007).

Rader et al., A phage display approach for rapid antibody humanization: designed combinatorial v gene libraries, PNAS., 95:8910-8915 (1998).

Rahbar et al., B7-H4 Expression by nonhematopoietic cells in the tumor microenvironment promotes antitumor immunity, Cancer Immunology Research, 3(2):184-195 (2015).

Rahbar et al., B7-H4 is a positive regulator of antitumor immunity, Oncoimmunology, 5(1):e1050575 (2016).

Raju, Glycosylation variations with expression systems and their impact on biological activity of therapeutic Immunoglobulins, BioProcess International, 1(4):44-53 (2003).

Riechmann et al., Reshaping human antibodies for therapy, Nature, 332:323-329 (1988).

Roguska et al., A comparison of two murine monoclonal antibodies humanized by CDR-grafting and variable domain resurfacing, Protein Eng., 9(10):895-904 (1996).

Roguska et al., Humanization of murine monoclonal antibodies through variable domain resurfacing, Proc. Natl. Acad. Sci. USA, 91(3):969-973 (1994).

Routier et al., Tile glycosylation pattern of a humanized IgGI antibody (01 .3) expressed in CHO cells, Glycoconjugate Journal, 14:201-207 (1997).

Roversi et al., Modelling prior distributions of atoms for macromolecular refinement and completion, Acta. Crystallogr. D. Biol. Crystallogr., 56(Pt 10):1316-1323 (2000).

Sadun et al., Immune signatures of murine and human cancers reveal unique mechanisms of tumor escape and new targets for cancer immunotherapy, Cancer Therapy: Preclinical, 13(13):4016-4025 (2007).

Salceda et al., The immunomodulatory protein B7-H4 is overexpressed in breast and ovarian cancers and promotes epithelial cell transformation, Experimental Cell Research, 306(1):128-141 (2005).

Sambrook et al., Molecular cloning: a laboratory manual, 3rd edition, J.F. Sambrook and D.W. Russell, ed., Cold Spring Harbor Laboratory Press: Cold Spring Harbor, NY, 2:107 (2001).

Sankin et al., The expanding repertoire of targets for immune checkpoint inhibition in bladder cancer: What lies beneath the tip of the iceberg, PD-L1, Urologic Oncology, 36(10):459-468 (2018).

Schalper et al., Differential expression and significance of PD-L1, IDO-1, and B7-H4 in human lung cancer, Clin. Cancer Research, 23(2):370-378 (2017).

Seliger et al., 'The complex role of B7 molecules in rumor immunology., Trends Mol. Med., 14(12):550-559 (2008).

Shaffer et al., Dissecting the tumor micro-environment in triple negative breast cancer identifies a mutually exclusive expression pattern of the immune co-inhibitory molecules B7-H 4 and PD-L1, Journal for Immunotherapy of Cancer, 3(2):017 (2015).

Sheehan et al., Phage and yeast display, Microbiol. Spectr., 3(1):AID-0028-2014 (2015).

Shen et al., B7-H4 Is a prognostic biomarker for poor survival in patients with pancreatic cancer, Human Pathology, 66:79-85 (2017).

Shi et al., Serum B7-H4 expression is a significant prognostic indicator for patients with gastric cancer, World Journal of Surgical Oncology, 12:188 (2014).

Shields et al., High resolution mapping of the binding site on human IgG1 for FcγRI, FcγII. FcγIII, and FcRn and design of IgG1 variants with improved binding to the FcγR, J. Biol. Chem., 276(9):6591-6604 (2001).

Shields et al., Lack of fucose on human IgG1 N-linked oligosaccharide improves binding to human FcγRIII and antibody-dependent cellular toxicity, J. Biol. Chem., 277:26733-26740 (Jul. 26, 2002, e-pub. May 1, 2002).

Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chemistry, 278(5):3466-3473 (2003).

Shrestha et al., Monitoring immune checkpoint regulators as predictive biomarkers in hepatocellular carcinoma, Frontiers in Oncology, 8:269 (2018).

Sica et al., B7-H4, a Molecule of the B7 family, Negatively regulates T cell immunity, Immunity, 18(6):849-861 (2003).

Siegel et al., High efficiency recovery and epitope-specific sorting of an scFv yeast display library, J. Immunol. Methods, 286(1-2):141-153, (2004).

Simon et al., B7-H4 is a novel membrane-bound protein and a candidate serum and tissue biomarker for ovarian cancer, Cancer Research, 66(3):1570-1575 (2006).

Simon et al., B7-H4 Is over-expressed in early-stage ovarian cancer and is independent of CA125 expression, Gynecologic Oncology, 106(2):334-341 (2007).

Simon et al., Evaluation of B7-H4 (DD-O110) as a prognostic marker in tissue and serum of ovarian cancer patients, Cancer Research, Abstract 4882, retrieved from https://cancerres.aacrjournals. org/content/65/9_Supplement/1153.2, last visited Apr. 30, 2020, 4 (2005).

Smith et al., B7-H4 as a potential target for immunotherapy for gynecologic cancers: A closer look, Gynecologic Oncology, 134(1):181-189 (2014).

Smith et al., Mouse model recapitulating human fcy receptor structural and functional diversity, PNAS, 109(16):6181-6186 (Apr. 17, 2012, e-pub. Apr. 2, 2012).

Smith et al., Tumor regression and delayed onset toxicity following B7-H4 car T cell therapy, Mol. Therapy, 24(11):1987-1999 (2016).

Song et al., Prognostic role of high B7-H4 expression in patients with solid tumors: a meta-analysis, Oncotarget, Advance Publications:1-11, Impact Journals, United States (2016).

Sood, PDEF and PDEF-induced proteins as candidate tumor antigens for T cell and antibody-mediated immunotherapy of breast cancer, Immunol. Res., 46:206-215 (2010, e-pub. Sep. 10, 2009).

Sun et al., B7-H3 and B7-H4 expression in non-small-cell lung cancer, Lung Cancer, 53(2):143-151 (2006).

Tan et al., Prognostic role of B7-H4 in patients with non-small cell lung cancer: A meta-analysis, Oncotarget, 8(16):27137-27144 (2017).

Terrett et al., Preclinical development of anti B7-H4 therapeutic antibodies, Cancer Research, Abstract 4986, retrieved from https://canerres.accrjournals.org/content/68/9 Supplement/4986, last visited Apr. 30, 2020, 3 (2008).

(56) References Cited

OTHER PUBLICATIONS

Thompson et al., B7-H1, Glycoprotein blockade: A novel strategy to enhance immunotherapy in patients with renal cell carcinoma., Urology, 66(Suppl. 5A):10-14 (2005).

Thompson et al., Serum-soluble B7x Is elevated in renal cell carcinoma patients and is associated with advanced stage, Cancer Research, 68(15):6054-6058 (2008).

Tramontano et al., Framework residue 71 is a major determinant of the position and conformation of the second hypervariable region in the vh domains of Immunoglobulins, J. Mol. Biol., 215(1):175-182 (1990).

Tringler et al., B7-H4 is highly expressed in ductal and lobular breast cancer, Clinical Cancer Research, 11(5):1842-1848 (2005).

Tringler et al., B7-H4 overexpression in ovarian tumors, Gynecologic Oncology, 100(1):44-52 (2006).

Umana et al., Engineered glycoforms of an antineuro-Biastoma IgG 1 with optimized antibody-dependent cellular cytotoxic activity, Nat. Biotechnol., 17:176-180 (1999).

Van Regenmortel, MHV., Development of a preventive HIV vaccine requires solving inverse problems which is unattainable by rational vaccine design, Front. Immunol., 8:2009 (2018).

Verhoeyen et al., Reshaping human antibodies: Grafting an antilysozyme activity, Science, 239(4857):1534-1536 (1988).

Wagener et al., Monoclonal antibodies for carcinoembryonic antigen and related antigens as a model system: a systematic approach for the determination of epitope specificities of monoclonal antibodies, J. Immunol., 130(5):2308-2315 (1983).

Wagener et al., Use of biotin-labeled monoclonal antibodies and avidin-peroxidase conjugates for the determination of epitope specificities in a solid-phase competitive enzyme immunoassay, J. Immunol. Methods, 68(1-2):269-274 (1984).

Jun Gong et al., "Development of PD-1 and PDL1 inhibitors as a form of cancer immunotherapy: a comprehensive review of registration trials and future considerations", Journal for Immuno Therapy of Cancer, vol. 6, No. 8, pp. 1-18 (2018).

Epstein, A.L., B7-H4 as a target for breast cancer immunotherapy, Research Grant W81XWH-11-1-0466, 18 (2012).

Estep et al., High throughput solution-based measurement of antibody-antigen affinity and epitope binning, MAbs, 5(2):270-278 (2013).

Fan et al., B7-H4 expression is Correlated With Tumor Progression and Clinical Outcome in Urothelial Cell Carcinoma, International Journal of Clinical and Experimental Pathology, 7(10):6768-6775 (Oct. 1, 2014, e-pub. Sep. 15, 2014).

Ferrara et al., Modulation of therapeutic antibody effector functions by glycosylation engineering: influence of golgi enzyme localization domain and co-expression of heterologous b1, 4-n-acetylglucosaminyltransferase III and golgi a-mannosidase, Biotechnology and Bioengineering, 93(5):851-861 (2006, e-pub. Jan. 24, 2006).

Ferrara et al., Recombinant renewable polyclonal antibodies, mAbs, 7:32-41 (2015).

Ferreira et al., Circulating tumor cell technologies, Mol. Oncol., 10(3):374-94 (2016).

Filies et al., The new B7s: Playing a pivotal role in tumor immunity, J. Immunother., 30:251-260 (2007).

Foecking et al., Powerful and versatile enhancer-promoter unit for mammalian expression vectors, Gene, 45(1):101-105 (1986).

Fukuda et al., Higher preoperative serum levels of pd-l1 and b7-h4 are associated with invasive and metastatic potential and predictable for poor response to VEGF-targeted therapy and unfavorable prognosis of renal cell carcinoma, Cancer Medicine, 5(8):1810-1820 (2016).

Gao et al., Effect of VTCN1 on progression and metastasis of ovarian carcinoma in vitro and vivo, Biomedicine & Pharmacotherapy, 73:129-134 (2015).

GCC Office Action, dated Jan. 20, 2020, for GCC Patent Application No. GC2018-35987, 6 pages.

Geng et al., Expression of costimulatory molecules B7-H1, B7-H4 and Foxp3+tregs in gastric cancer and its clinical significance, Int. J. Clin. Oncology, 20(2):273-281 (2015).

Giege et al., Crystallogenesis of biological macromolecules: Facts and perspectives, Acta Crystallogr D. Biol. Crystallogr., 50(Pt 4):339-350 (1994).

Goding, Production of monoclonal antibodies, Chapter 3 in monoclonal antibodies: Principles and Practice, Academic Press, New York, 59-103 (1986).

Goldberg et al., Abstract C243: B7-H4 protein expression in invasive ductal carcinoma and its association with tumor progression, Molecular Cancer Therapeutics, retrieved from https://mct.aacrjournals.org/content/8/12_Supplement/C243, last visited Apr. 30, 2020, 4 (2009).

Hammerling et al., Production of antibody-producing hybridomas in the rodent systems, in research monographs in immunology, Elsevier/North-Holland Biomedical Press, 3:563-587 (1981).

Han et al., Negative roles of B7-H3 and B7-H4 in the microenvironment of cervical cancer, Experimental cell research, Author's accepted manuscript, Academic Press, United States (2018).

Han et al., Roles of immune inhibitory molecule B7-H4 in cervical cancer, Oncology Reports, 37(4):2308-2316 (2017).

Hansen et al., The B7 family of Immunoregulatory receptors: a comparative and evolutionary perspective, Mol. Immun., 46(3):457-472 (2009).

Harlow et al., Antibodies a Laboratory Manual, Cold Spring Harbor Press, 89 (1988).

He et al., The inhibitory role of B7-H4 in antitumor immunity: association with cancer progression and survival, Clinical & Developmental Immunology, 2011:695834, (8 pages), Hindawi Publishing Corporation, Egypt (2011).

Herber et al., Meeting report: mechanism and therapeutic reversal of immune suppression in cancer, Cancer Res., 67(11):5067-5069 (2007).

Horsten et al., Production of non-fucosylated antibodies by co-expression of heterologous GDP-6-deoxy-D-lyxo-4-hexulose reductase, Glycobiology, 20(12):1607-18 (2010).

Huang et al., B7-H3, B7-H4, Foxp3 and IL-2 Expression in cervical cancer: Associations with patient outcome and clinical significance, Oncology Reports, 35(4):2183-2190 (2016).

Huang et al., Clinical significance of the B7-H4 as a novel prognostic marker in breast cancer, Gene, Author's Manuscript, Elsevier, Netherlands (2017).

Ichikawa et al., Role of B7-H1 and B7-H4 molecules in down-regulating effector phase of t-cell immunity: novel cancer escaping mechanisms, Frontiers in Bioscience, 10:2856-2860 (2005).

Iida et al., Two mechanisms of the enhanced antibody-dependent cellular cytotoxicity (ADCC) efficacy of non-fucosylated therapeutic antibodies in human blood, BMC Cancer, 9:58 (12 pages), BioMed Central, England (2009).

Iizuka et al., Unstable B7-H4 cell surface expression and T-cell redirection as a means of cancer therapy, Oncology Reports, 36(5):2625-2632 (2016).

Imai-Nishiya Harue et al., Double knockdown of a1,6-fucosyltransferase (FUT8) and GDP-mannose 4,6-dehydratase (GMD) In antibody-producing cells: A new strategy for generating fully non-fucosylated therapeutic antibodies with enhanced ADCC, BMC Biotechnology, 7:84 (2007).

International Preliminary Report on Patentability, issued Aug. 27, 2020, for PCT Application No. PCT/US2019/018965, filed Feb. 21, 2019.

International Preliminary Report on Patentability, issued Aug. 27, 2020, for PCT Application No. PCT/US2019/018966, filed Feb. 21, 2019.

International Preliminary Report on Patentability, issued Sep. 8, 2020, for PCT Application No. PCT/US2019/020189, filed Mar. 1, 2019.

International Search Report and Written Opinion for International Application No. PCT/US2018/047805, International Search Authority, United States, mailed on Dec. 12, 2018.

International Search Report and Written Opinion, mailed Jan. 28, 2020, for PCT Application No. PCT/US2019/056210, filed Oct. 15, 2019.

International Search Report and Written Opinion, mailed Jun. 12, 2019, for PCT Application No. PCT/US2019/018965, filed Feb. 21, 2019, 11 pages.

(56)　　　　　References Cited

OTHER PUBLICATIONS

International Search Report and Written Opinion, mailed Jun. 14, 2019, for PCT Application No. PCT/US2019/018963, filed Feb. 21, 2019.

International Search Report and Written Opinion, mailed May 17, 2019, for PCT Application No. PCT/US2019/020189, filed Mar. 1, 2019.

Janakiram et al., The third group of the B7-CD28 immune check-point family: HHLA2, TMIGD2, B7x, and B7-H3, Immunological Reviews, 276(1):26-39, (2017).

Jennewein et al., The Immunoregulatory roles of antibody glycosylation, Trends in Immunology, 38(5):358-372 (2017).

Jeon et al., Structure and cancer immunotherapy of the B7 family member B7x, Cell. Rep., 9(3):1089-98 (2014).

Jiang et al., Tumor expression of B7-H4 predicts poor survival of patients suffering from gastric cancer, Cancer Immunology, 59(11):1707-1714 (2010).

Jiang et al.,, B7-H4 expression and increased death risk of cancer patients: A meta-analysis, J. Cancer Res. Clin. Oncol., 8:229-234 (2011).

Jones et al., Replacing the complementarity-determing regions in a human antibody with those from a mouse, Nature, 321:522-525 (1986).

Kabat et al., Attempts to locate complementarity-determining residues in the variable positions of light and heavy chains, Ann. NY Acad. Sci., 190:382-391 (1971).

Kabat et al., Sequences of proteins of immunological interest, 5th ed., public health service, National Institutes of Health, Bethesda, MO. TOC, 21 (1991).

Kamimura et al., Possible involvement of soluble B7-H4 in T cell-mediated inflammatory immune responses, Biochem. Biophysical Res. Communications, 389(2):349-353 (2009).

Kanda et al., Comparison of biological activity among nonfucosylated therapeutic Igg1 antibodies with three different N-linked Fc oligosaccharides: The high-mannose, Hybrid, and Complex Types, Glycobiology, 17(1):104-118 (Jan. 2007, e-pub. Sep. 29, 2006).

Kaplan et al., FPA 150, a novel B7-H4 therapeutic antibody with checkpoint blockade and ADCC activities, ESMO 2017 Congress, Madrid, Spain; Poster, 1 (2017).

Kettleborough et al., Isolation of tumor cell-specific single-chain Fv from immunized mice using Page-antibody libraries and the Reconstruction of whole antibodies from these antibody fragments, Eur. J. Immunol., 24(4):952-958 (1994).

Khan et al., Cross-neutralizing anti-HIV-1 human single chain variable fragments(scFvs) against CD4 binding site and N332 glycan identified from a recombinant phage library, Sci. Rep., 7:45163; doi: 10.1038/srep45163, 12 (2017).

Kim et al., Guided selection of human antibody light chains against TAG-72 using A phage display chain shuffling approach, J. Microbiol., 45:572-577 (2007).

Kim et al., Immune signature of metastatic breast cancer: identifying predictive markers of immunotherapy response, Oncotarget, Advance Publications:1-12, Impact Journals, United States (2017).

Kirkland et al., Analysis of the fine specificity and cross-reactivity of monoclonal anti-lipid A antibodies, J. Immunol., 137(11):3614-3619 (1986).

Kitamura et al., Prognostic biomarkers of renal cell carcinoma: Recent advances, Indian J. Urol., 24(1):10-15 (2008).

Klatte et al., Best of the 2006 AUA annual meeting: highlights from the 2006 annual meeting of the Am. Urological Assoc., 8(3):120-164 (2006).

Kohler et al., Continuous cultures of fused cells secreting antibody of predefined specificity, Nature, 256:495-497 (1975).

Konitzer et al., Generation of a highly diverse panel of antagonistic chicken monoclonal antibodies against the GIP receptor, mAbs, 9:536-549 (2017).

Krambeck et al., B7-H4 expression in renal cell carcinoma and tumor vasculature: Associations with cancer progression and survival, Proc. Nat. Acad. Sci. USA, 103(27):10391-10396 (2006).

Kryczek et al., B7-H4 expression identifies a novel suppressive macrophage population in human ovarian carcinoma, J. Experimental Med., 203(4):871-881 (2006).

Kryczek et al., Relationship between B7-H4, regulatory t cells, and patient outcome in human ovarian carcinoma, Cancer Research, 67(18):8900-8905(2007).

Kuroki et al., Biochemical characterization of 25 distinct carcinoembryonic antigen (CEA) Epitopes recognized by 57 monoclonal antibodies and categorized into seven groups in terms of domain structure of the CEA molecule, Hybridoma, 11(4):391-407 1992).

Kuroki et al., Determination of epitope specificities of a large number of monoclonal antibodies by solid-phase mutual inhibition assays using biotinylated antigen, Immunol. Invest., 21(6):523-538 (Oct. 1992, e-pub. Jul. 7, 2009).

Kuroki et al., Serological mapping of the tag-72 tumor-associated antigen using 19 distinct monoclonal antibodies, Cancer Res., 50:4872-4879 (1990).

Lee et al., Molecular-level analysis of the serum antibody repertoire in young adults before and after seasonal Influenza vaccination, Nature Medicine, 22:1456-1464 (2016).

Lefranc et al., IMGT, The intenational immuno Genetics database, Nucleic Acids Res., 27(1):209-212 (1999).

Lefranc, The IMGT unique numbering for Immunoglobulins, t-cell receptors, and Ig-like domains, The Immunologist., 7(4):132-136 (1999).

Leong et al., An anti-B7-H4 antibody-drug conjugate for the treatment of breast cancer, Mol. Pharm., 12(6):1717-1729 (2015).

Leung et al., Host B7-H4 regulates antitumor t cell responses through inhibition of myeloid-derived suppressor cells in a 4T1 tumor transplantation model, J. Immunology, 190(12):6651-6661 (2013).

Leung et al., Synergistic effects of host B7-H4 deficiency and gemcitabine treatment on tumor regression and anti-tumor T cell immunity in a mouse model, Cancer Immunology, 66(4):491-502 (2017).

Li et al., Co-inhibitory molecule b7 superfamily member 1 expressed by tumor-infiltrating myeloid cells induces dysfunction of anti-tumor CD8+ T cells, Immunity Cell Press, 48:1-14 (2018).

Li et al., Summary of the primer on tumor immunology and the biological therapy of cancer, J. Translational Medicine, 7:11 (2009).

Liu et al., B7-H4 expression in bladder urothelial carcinoma and immune escape mechanisms, Oncology Letters, 8(6):2527-2534.

Liu et al., B7-H4 Expression in human infiltrating ductal carcinoma-associated macrophages, Molecular Medicine Report, 14(3):2135-2142 (2016).

Liu et al., Expression of immune checkpoint molecules in endometrial carcinoma, Experimental and Therapeutic Medicine, 10(5):1947-1952 (2015).

Liu et al., High-throughput screening for developability during early-stage antibody discovery using self-interaction nanoparticle spectroscopy, MAbs, 6(2):483-492 (2014).

Loke et al., Emerging mechanisms of immune regulation: the extended 87 family and regulatory T cells, Arthritis Research & Therapy, 6(5):208-214 (2004).

Longmore et al., Product-identification and substrate-specificity studies of the GDP-L-fucose:2-acetamido-2-deoxy-beta-D-glucoside (FUC To Asn-Linked GlcNAc) 6-alpha-L-fucosyltransferase in a golgi-rich fraction from porcine liver, Carbohydr. Res., 100:365-392 (1982).

MacCallum et al., Antibody-antigen interactions: contact analysis and binding site topography, J. Mol. Biol., 262:732-745 (1996).

MacGregor et al., Molecular pathways: evaluating the potential for B7-H4 as an immunoregulatory target, Clin. Cancer Res., 23(12):2934-2941 (2017).

Mao et al., Recombinant human B7-H4 expressed in *Escherichia coli* inhibits T lymphocyte proliferation and IL-2 secretion in vitro, Acta. Pharmacologica. Sinica., 27(6):741-746 (2006).

Martin, Protein sequence and structure analysis of antibody variable domains, in antibody engineering, Kontermann and Dithei, eds., Chapter 31, 422-439 (2001).

(56)                    References Cited

OTHER PUBLICATIONS

Matsunaga et al., Increased B7-H1 and B7-H4 expressions on circulating monocytes and tumor-associated macrophages are involved in immune evasion in patients with gastric cancer, Yonago Acta Medica, 54(1):1-10 (2011).

McPherson, Crystallization of proteins from polyethylene glycol, J. Biol. Chem., 251(20):6300-6303 (1976).

McPherson, Current approaches to macromolecular crystallization, Eur. J. Biochem., 189:1-23 (1990).

Meng et al., B7-H4 as an Independent prognostic indicator of cancer patients: a meta-analysis, Oncotarget, 8(40):68825-68836 (2017).

Miyatake et al., B7-H4 (DO-O110) immunocytochemistry improves tile sensitivity of cancer cell detection in pelvic wash specimens of metastatic ovarian cancer, Cancer Research, Abstract 4502, retrieved from https://cancerres.aacrjounals.org/content/66/8_Supplement/1056.4, last visited Apr. 30, 2020, 4 (2006).

Miyatake et al., B7-H4 (DD-0110) is overexpressed in uterine endometrioid carcinomas independent of tumor grade, T cell infiltration, or apoptotic index, Cancer Research, Abstract 3604, retrieved from https://canceres.aacrjournals.org/content/65/9_Supplement/849.5, last visited May 1, 2020, 4 (2005).

Miyatake et al., B7-H4 (DD-O110) Is overexpressed in high risk uterine endometrioid adenocarcinomas and inversely correlated with tumor t-cell infiltration, Gynecologic Oncology, 106(1):119-127 (2007).

Moldenhauer et al., Identity of HML-1 antigen on intestinal intraepithelial T celis and of B-ly7 antigen on hairy cell leukaemia, Scand J. Immunol., 32(2):77-82 (1990).

Morel et al., Monoclonal antibodies to bovine serum albumin: Affinity and specificity determinations, Mol. Immunol., 25(1):7-15 (1988).

Mugler et al., B7-H4 Expression in a range of breast pathology: correlation with tumor t-cell infiltration, Applied Immunohistochemistry and Molecular Morphology, 15(4):363-370 (2007).

Murillo et al., Potentiation of therapeutic immune responses against malignancies with monoclonal antibodies, Clinical Cancer Research, 9:5454-5464 (2013).

Niwa et al., Enhanced natural killer cell binding and activation by low-fucose Igg1 antibody results in potent antibody-dependent cellular cytotoxicity induction at lower antigen density, Clinical Cancer Research, 11(6):2327-2336 (2005).

Niwa et al., Enhancement of the antibody-dependent cellular cytotoxicity of low-fucose IgG1 is independent of FcγRIIIa functional polymorphIsm, Clin. Cancer Res., 10:6248-6255 (2004).

Ohaegbulam et al., Tumor-expressed immune checkpoint B7X promotes cancer progression and antigen-specific CD8 T Cell exhaustion and suppressive innate immune cells, Oncotarget, 8(47):82740-82753 (2017).

Palena et al., Review article vaccines against human carcinomas: strategies to improve antitumor immune responses, J. Biomedicine and Biotechnology, 2010(380697):1-12 (2010).

Parola et al., Integrating high-throughput screening and sequencing for monoclonal antibody discovery and engineering, Immunology, 153:31-41 (2018).

Persic et al., An integrated vector system for the eukaryotic expression of antibodies or their fragments after selection from phage display libraries, Gene, 187(1):9-18 (1997).

Podojil et al., Potential targeting of B7-H4 for the treatment of cancer, Immunological Reviews, 276(1):40-51 (2017).

Prasad et al., B7S1, a novel B7 Family member that negatively regulates T cell activation., Immunity, 18(6):863-873 (2003).

"Specialized knowledge in pharmaceutics (I), 7th Version", Practicing Pharmacist Qualification Certification Center under State Food and Drug Administration China medical science press, 6 pages (2015).

Chang et al., Practical approaches to protein formulation development in "Rationale Design of stable protein formulations-theory and practice" (J.F. Carpenter and M.C. Manning eds.) Kluwer Academic/Plenum publishers, New York., pp. 1-25 (2002).

GenBank, immunoglobulin, partial [*Homo sapiens*] CAA69703.1 (Jul. 26, 2016).

Goswami et al., Development and Challenges for mAb-Based Therapeutics, Antibodies 2013, 2, 452-500 (2013).

International Application No. PCT/US2018/047805, International Preliminary Report on Patentability, mailed Mar. 5, 2020.

International Application No. PCT/US2019/056210, International Preliminary Report on Patentability, mailed Apr. 29, 2021.

International Application No. PCT/US2019/018963, International Preliminary Report on Patentability, mailed Sep. 3, 2020.

Kang et al., Rapid Formulation Development for Monoclonal Antibodies, BioProcess International, 14(4):1-4 (Apr. 2016).

Shao et al., Construction of anti-B7-H4-scFv library and screening and identification of anti-B7-H4-scFv, Chin J. Cell Mol. Immunol, 32 (09):1260-1266 (2016).

Uchiyama S., Liquid formulation for antibody drugs, Biochimica et Biophysica Acta (BBA)—Proteins and Proteomics, 1844(11):2041-2052 (Nov. 2014).

Verhoeven et al., Reshaping human antibodies: Grafting an antilysozyme activity, Science, 239(4857):1534-1536 (1988).

Wang W., Instability, stabilization, and formulation of liquid protein pharmaceuticals, International Journal of Pharmaceutics, 185(2):129-188 (Aug. 1999).

Whitaker et al., A Formulation Development Approach to Identify and Select Stable Ultra-High-Concentration Monoclonal Antibody Formulations With Reduced Viscosities, Journal of Pharmaceutical Sciences, 106(11):3230-3241 (Nov. 2017).

Xiaoju et al., Screening and Identification of Antigen Epitope of hB7-H4 Recognized by Monoclonal Antibody with 12 phage Display Peptide Library, Letters in Biotechnology, 26(4):505-509 (Jul. 31, 2015).

Li et al., Co-inhibitory Molecule B7 Superfamily Member 1 Expressed by Tumor-Infiltrating Myeloid Cells Induces Dysfunction of Antitumor CD8+ T Cells, Immunity, 48(4):773-786 (Apr. 2018).

Meyer et al., Better Together: B7H1 Checkpoint Blockade Synergizes with anti-PD1, Immunity, 48(4):621-623 (Apr. 2018).

Nanda et al., Pembrolizumab in Patients With Advanced Triple-Negative Breast Cancer: Phase Ib Keynote-012 Study, Journal of Clinical Oncology, 34(21):2460-2467 (Jul. 2016).

* cited by examiner

SEQUENCE LISTING

<160> NUMBER OF SEQ ID NOS: 41

<210> SEQ ID NO 1
<211> LENGTH: 282
<212> TYPE: PRT
<213> ORGANISM: Homo sapiens

<400> SEQUENCE: 1

Met Ala Ser Leu Gly Gln Ile Leu Phe Trp Ser Ile Ile Ser Ile Ile
1               5                   10                  15

```
Ile Ile Leu Ala Gly Ala Ile Ala Leu Ile Ile Gly Phe Gly Ile Ser
        20              25              30

Gly Arg His Ser Ile Thr Val Thr Thr Val Ala Ser Ala Gly Asn Ile
        35              40              45

Gly Glu Asp Gly Ile Leu Ser Cys Thr Phe Glu Pro Asp Ile Lys Leu
    50              55              60

Ser Asp Ile Val Ile Gln Trp Leu Lys Glu Gly Val Ile Gly Leu Val
65              70              75              80

His Glu Phe Lys Glu Gly Lys Asp Glu Leu Ser Glu Gln Asp Glu Met
                85              90              95

Phe Arg Gly Arg Thr Ala Val Phe Ala Asp Gln Val Ile Val Gly Asn
            100             105             110

Ala Ser Leu Arg Leu Lys Asn Val Gln Leu Thr Asp Ala Gly Thr Tyr
        115             120             125

Lys Cys Tyr Ile Ile Thr Ser Lys Gly Lys Gly Asn Ala Asn Leu Glu
    130             135             140

Tyr Lys Thr Gly Ala Phe Ser Met Pro Glu Val Asn Val Asp Tyr Asn
145             150             155             160

Ala Ser Ser Glu Thr Leu Arg Cys Glu Ala Pro Arg Trp Phe Pro Gln
            165             170             175

Pro Thr Val Val Trp Ala Ser Gln Val Asp Gln Gly Ala Asn Phe Ser
            180             185             190

Glu Val Ser Asn Thr Ser Phe Glu Leu Asn Ser Glu Asn Val Thr Met
        195             200             205

Lys Val Val Ser Val Leu Tyr Asn Val Thr Ile Asn Asn Thr Tyr Ser
    210             215             220

Cys Met Ile Glu Asn Asp Ile Ala Lys Ala Thr Gly Asp Ile Lys Val
225             230             235             240

Thr Glu Ser Glu Ile Lys Arg Arg Ser His Leu Gln Leu Leu Asn Ser
            245             250             255

Lys Ala Ser Leu Cys Val Ser Ser Phe Phe Ala Ile Ser Trp Ala Leu
        260             265             270

Leu Pro Leu Ser Pro Tyr Leu Met Leu Lys
        275             280
```

```
<210> SEQ ID NO 2
<211> LENGTH: 282
<212> TYPE: PRT
<213> ORGANISM: Artificial Sequence
<220> FEATURE:
<223> OTHER INFORMATION: Cynomolgus monkey B7-H4

<400> SEQUENCE: 2
```

```
Met Ala Ser Leu Gly Gln Ile Leu Phe Trp Ser Ile Ile Ser Ile Ile
1               5               10              15

Phe Ile Leu Ala Gly Ala Ile Ala Leu Ile Ile Gly Phe Gly Ile Ser
        20              25              30

Gly Arg His Ser Ile Thr Val Thr Thr Val Ala Ser Ala Gly Asn Ile
        35              40              45

Gly Glu Asp Gly Ile Leu Ser Cys Thr Phe Glu Pro Asp Ile Lys Leu
    50              55              60

Ser Asp Ile Val Ile Gln Trp Leu Lys Glu Gly Val Ile Gly Leu Val
65              70              75              80

His Glu Phe Lys Glu Gly Lys Asp Glu Leu Ser Glu Gln Asp Glu Met
                85              90              95
```

```
Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
            130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175

Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
        210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Leu Ala Ile Ser Trp Ala Leu
            260                 265                 270

Leu Pro Leu Ala Pro Tyr Leu Met Leu Lys
        275                 280
```

<210> SEQ ID NO 3
<211> LENGTH: 283
<212> TYPE: PRT
<213> ORGANISM: Artificial Sequence
<220> FEATURE:
<223> OTHER INFORMATION: Murine B7-H4

<400> SEQUENCE: 3

```
Met Ala Ser Leu Gly Gln Ile Ile Phe Trp Ser Ile Ile Asn Ile Ile
1                   5                   10                  15

Ile Ile Leu Ala Gly Ala Ile Ala Leu Ile Ile Gly Phe Gly Ile Ser
            20                  25                  30

Gly Lys His Phe Ile Thr Val Thr Thr Phe Thr Ser Ala Gly Asn Ile
        35                  40                  45

Gly Glu Asp Gly Thr Leu Ser Cys Thr Phe Glu Pro Asp Ile Lys Leu
        50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
                85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
            115                 120                 125

Thr Cys Tyr Ile Arg Thr Ser Lys Gly Lys Gly Asn Ala Asn Leu Glu
        130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
                165                 170                 175
```

-continued

```
Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Gln Leu Leu Asn Ser
            245                 250                 255

Gly Pro Ser Pro Cys Val Phe Ser Ser Ala Phe Val Ala Gly Trp Ala
            260                 265                 270

Leu Leu Ser Leu Ser Cys Cys Leu Met Leu Arg
            275                 280

<210> SEQ ID NO 4
<211> LENGTH: 282
<212> TYPE: PRT
<213> ORGANISM: Artificial Sequence
<220> FEATURE:
<223> OTHER INFORMATION: Rat B7-H4

<400> SEQUENCE: 4

Met Ala Ser Leu Gly Gln Ile Ile Phe Trp Ser Ile Ile Asn Val Ile
1               5                   10                  15

Ile Ile Leu Ala Gly Ala Ile Val Leu Ile Ile Gly Phe Gly Ile Ser
            20                  25                  30

Gly Lys His Phe Ile Thr Val Thr Thr Phe Thr Ser Ala Gly Asn Ile
            35                  40                  45

Gly Glu Asp Gly Thr Leu Ser Cys Thr Phe Glu Pro Asp Ile Lys Leu
            50                  55                  60

Asn Gly Ile Val Ile Gln Trp Leu Lys Glu Gly Ile Lys Gly Leu Val
65                  70                  75                  80

His Glu Phe Lys Glu Gly Lys Asp Asp Leu Ser Gln Gln His Glu Met
            85                  90                  95

Phe Arg Gly Arg Thr Ala Val Phe Ala Asp Gln Val Val Val Gly Asn
            100                 105                 110

Ala Ser Leu Arg Leu Lys Asn Val Gln Leu Thr Asp Ala Gly Thr Tyr
            115                 120                 125

Thr Cys Tyr Ile His Thr Ser Lys Gly Lys Gly Asn Ala Asn Leu Glu
            130                 135                 140

Tyr Lys Thr Gly Ala Phe Ser Met Pro Glu Ile Asn Val Asp Tyr Asn
145                 150                 155                 160

Ala Ser Ser Glu Ser Leu Arg Cys Glu Ala Pro Arg Trp Phe Pro Gln
            165                 170                 175

Pro Thr Val Ala Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
            195                 200                 205

Lys Val Val Ser Val Leu Tyr Asn Val Thr Ile Asn Asn Thr Tyr Ser
            210                 215                 220

Cys Met Ile Glu Asn Asp Ile Ala Lys Ala Thr Gly Asp Ile Lys Val
225                 230                 235                 240

Thr Asp Ser Glu Val Lys Arg Arg Ser Gln Leu Glu Leu Leu Asn Ser
            245                 250                 255
```

```
Gly Pro Ser Pro Cys Val Ser Ser Val Ser Ala Ala Gly Trp Ala Leu
            260                 265                 270

Leu Ser Leu Ser Cys Cys Leu Met Leu Arg
        275                 280
```

```
<210> SEQ ID NO 5
<211> LENGTH: 11
<212> TYPE: PRT
<213> ORGANISM: Artificial Sequence
<220> FEATURE:
<223> OTHER INFORMATION: VH CDR1

<400> SEQUENCE: 5

Gly Ser Ile Lys Ser Gly Ser Tyr Tyr Trp Gly
1               5                   10
```

```
<210> SEQ ID NO 6
<211> LENGTH: 16
<212> TYPE: PRT
<213> ORGANISM: Artificial Sequence
<220> FEATURE:
<223> OTHER INFORMATION: VH CDR2

<400> SEQUENCE: 6

Asn Ile Tyr Tyr Ser Gly Ser Thr Tyr Tyr Asn Pro Ser Leu Arg Ser
1               5                   10                  15
```

```
<210> SEQ ID NO 7
<211> LENGTH: 12
<212> TYPE: PRT
<213> ORGANISM: Artificial Sequence
<220> FEATURE:
<223> OTHER INFORMATION: VH CDR3

<400> SEQUENCE: 7

Ala Arg Glu Gly Ser Tyr Pro Asn Gln Phe Asp Pro
1               5                   10
```

```
<210> SEQ ID NO 8
<211> LENGTH: 11
<212> TYPE: PRT
<213> ORGANISM: Artificial Sequence
<220> FEATURE:
<223> OTHER INFORMATION: VL CDR1

<400> SEQUENCE: 8

Arg Ala Ser Gln Ser Val Ser Ser Asn Leu Ala
1               5                   10
```

```
<210> SEQ ID NO 9
<211> LENGTH: 7
<212> TYPE: PRT
<213> ORGANISM: Artificial Sequence
<220> FEATURE:
<223> OTHER INFORMATION: VL CDR2

<400> SEQUENCE: 9

Gly Ala Ser Thr Arg Ala Thr
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: VL CDR3
```

<400> SEQUENCE: 10

Gln Gln Tyr His Ser Phe Pro Phe Thr
1               5

<210> SEQ ID NO 11
<211> LENGTH: 120
<212> TYPE: PRT
<213> ORGANISM: Artificial Sequence
<220> FEATURE:
<223> OTHER INFORMATION: VH Amino Acid

<400> SEQUENCE: 11

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: VL Amino Acid

<400> SEQUENCE: 12

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys
            100                 105

<210> SEQ ID NO 13
<211> LENGTH: 26
<212> TYPE: PRT
<213> ORGANISM: Artificial Sequence
<220> FEATURE:
<223> OTHER INFORMATION: VH FR1

-continued

<400> SEQUENCE: 13

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25
```

<210> SEQ ID NO 14
<211> LENGTH: 14
<212> TYPE: PRT
<213> ORGANISM: Artificial Sequence
<220> FEATURE:
<223> OTHER INFORMATION: VH FR2

<400> SEQUENCE: 14

```
Trp Ile Arg Gln Pro Pro Gly Lys Gly Leu Glu Trp Ile Gly
1               5                   10
```

<210> SEQ ID NO 15
<211> LENGTH: 30
<212> TYPE: PRT
<213> ORGANISM: Artificial Sequence
<220> FEATURE:
<223> OTHER INFORMATION: VH FR3

<400> SEQUENCE: 15

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30
```

<210> SEQ ID NO 16
<211> LENGTH: 11
<212> TYPE: PRT
<213> ORGANISM: Artificial Sequence
<220> FEATURE:
<223> OTHER INFORMATION: VH FR4

<400> SEQUENCE: 16

```
Trp Gly Gln Gly Thr Leu Val Thr Val Ser Ser
1               5                   10
```

<210> SEQ ID NO 17
<211> LENGTH: 23
<212> TYPE: PRT
<213> ORGANISM: Artificial Sequence
<220> FEATURE:
<223> OTHER INFORMATION: VL FR1

<400> SEQUENCE: 17

```
Glu Ile Val Met Thr Gln Ser Pro Ala Thr Leu Ser Val Ser Pro Gly
1               5                   10                  15

Glu Arg Ala Thr Leu Ser Cys
            20
```

<210> SEQ ID NO 18
<211> LENGTH: 15
<212> TYPE: PRT
<213> ORGANISM: Artificial Sequence
<220> FEATURE:
<223> OTHER INFORMATION: VL FR2

<400> SEQUENCE: 18

```
Trp Tyr Gln Gln Lys Pro Gly Gln Ala Pro Arg Leu Leu Ile Tyr
1               5                   10                  15
```

-continued

```
<210> SEQ ID NO 19
<211> LENGTH: 32
<212> TYPE: PRT
<213> ORGANISM: Artificial Sequence
<220> FEATURE:
<223> OTHER INFORMATION: VL FR3

<400> SEQUENCE: 19

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 20
<211> LENGTH: 10
<212> TYPE: PRT
<213> ORGANISM: Artificial Sequence
<220> FEATURE:
<223> OTHER INFORMATION: VL FR4

<400> SEQUENCE: 20

Phe Gly Gly Gly Thr Lys Val Glu Ile Lys
1               5                   10

<210> SEQ ID NO 21
<211> LENGTH: 450
<212> TYPE: PRT
<213> ORGANISM: Artificial Sequence
<220> FEATURE:
<223> OTHER INFORMATION: Full-Length Heavy Chain Amino Acid

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Lys Ser Gly
            20                  25                  30

Ser Tyr Tyr Trp Gly Trp Ile Arg Gln Pro Pro Gly Lys Gly Leu Glu
        35                  40                  45

Trp Ile Gly Asn Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Tyr Pro Asn Gln Phe Asp Pro Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

-continued

```
       210            215            220
Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 214
<212> TYPE: PRT
<213> ORGANISM: Artificial Sequence
<220> FEATURE:
<223> OTHER INFORMATION: Full-Length Light chain Amino Acid

<400> SEQUENCE: 22

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Ser Phe Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
              115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 23
<211> LENGTH: 107
<212> TYPE: PRT
<213> ORGANISM: Artificial Sequence
<220> FEATURE:
<223> OTHER INFORMATION: constant region of a human kappa light chain

<400> SEQUENCE: 23

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 24
<211> LENGTH: 321
<212> TYPE: DNA
<213> ORGANISM: Artificial Sequence
<220> FEATURE:
<223> OTHER INFORMATION: constant region of a human kappa light chain

<400> SEQUENCE: 24
cggaccgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 25
<211> LENGTH: 330
<212> TYPE: PRT
<213> ORGANISM: Artificial Sequence
<220> FEATURE:
```

```
<223> OTHER INFORMATION: human IgG1 heavy chain

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 990
<212> TYPE: DNA
<213> ORGANISM: Artificial Sequence
<220> FEATURE:
<223> OTHER INFORMATION: heavy chain constant domain

<400> SEQUENCE: 26
gcctccacca aggggcccatc ggtcttcccc ctggcaccct cctccaagag cacctctggg    60
```

-continued

```
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctggggggga     360 ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gggtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggatgag      720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa                                       990
```

<210> SEQ ID NO 27
<211> LENGTH: 360
<212> TYPE: DNA
<213> ORGANISM: Artificial Sequence
<220> FEATURE:
<223> OTHER INFORMATION: the variable heavy chain-encoding nucleotide

<400> SEQUENCE: 27

```
cagctgcagc tgcaggagtc gggcccagga ctggtgaagc cttcggagac cctgtccctc       60
acctgcactg tctctggtgg ctccatcaaa agtggtagtt actactgggg ctggatccgc      120
cagcccccag ggaaggggct ggagtggatt gggaacatct attatagtgg gagcacctac      180
tacaacccgt ccctcagaag tcgagtcacc atatccgtag acacgtccaa gaaccagttc      240
tccctgaagc tgagttctgt gaccgccgca gacacggcgg tgtactactg cgccagagaa      300
ggatcttacc ccaatcagtt tgatccatgg ggacagggta cattggtcac cgtctcctca      360
```

<210> SEQ ID NO 28
<211> LENGTH: 321
<212> TYPE: DNA
<213> ORGANISM: Artificial Sequence
<220> FEATURE:
<223> OTHER INFORMATION: variable light chain-encoding nucleotide
      sequence

<400> SEQUENCE: 28

```
gaaatagtga tgacgcagtc tccagccacc ctgtctgtgt ctccagggga aagagccacc       60
ctctcctgca gggccagtca gagtgttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcag taccactcct tcccctttcac ttttggcgga      300 gggaccaagg ttgagatcaa a                                                 321
```

<210> SEQ ID NO 29

-continued

```
<211> LENGTH: 385
<212> TYPE: PRT
<213> ORGANISM: Artificial Sequence
<220> FEATURE:
<223> OTHER INFORMATION: B7-H4 IgV-huIgG1

<400> SEQUENCE: 29

Met Ala Ser Leu Gly Gln Ile Leu Phe Trp Ser Ile Ile Ser Ile Ile
1               5                   10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
    50                  55                  60

Ser Asp Ile Val Ile Gln Trp Leu Lys Glu Gly Val Leu Gly Leu Val
65                  70                  75                  80

His Glu Phe Lys Glu Gly Lys Asp Glu Leu Ser Glu Gln Asp Glu Met
                85                  90                  95

Phe Arg Gly Arg Thr Ala Val Phe Ala Asp Gln Val Ile Val Gly Asn
                100                 105                 110

Ala Ser Leu Arg Leu Lys Asn Val Gln Leu Thr Asp Ala Gly Thr Tyr
            115                 120                 125

Lys Cys Tyr Ile Ile Thr Ser Lys Gly Lys Gly Asn Ala Asn Leu Glu
        130                 135                 140

Tyr Lys Thr Gly Ala Phe Ser Gly Ser Glu Pro Lys Ser Ser Asp Lys
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
                180                 185                 190

Arg Thr Pro Glu Val Thr Cys Val Val Val Asp Val Ser His Glu Asp
            195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
            275                 280                 285

Leu Pro Pro Ser Arg Asp Glu Leu Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
                340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
    370                 375                 380
```

Lys
385

<210> SEQ ID NO 30
<211> LENGTH: 447
<212> TYPE: PRT
<213> ORGANISM: Artificial Sequence
<220> FEATURE:
<223> OTHER INFORMATION: anti-PD-1 antibody  heavy chain

<400> SEQUENCE: 30

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
                35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

-continued

```
Pro Ser Gln Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
        370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Glu Gly Asn Val Phe Ser Cys Ser Val Met His Glu Ala Leu
            420             425             430

His Asn His Tyr Thr Gln Lys Ser Leu Ser Leu Ser Leu Gly Lys
        435             440             445
```

<210> SEQ ID NO 31
<211> LENGTH: 218
<212> TYPE: PRT
<213> ORGANISM: Artificial Sequence
<220> FEATURE:
<223> OTHER INFORMATION: anti-PD-1 antibody light chain

<400> SEQUENCE: 31

```
Glu Ile Val Leu Thr Gln Ser Pro Ala Thr Leu Ser Leu Ser Pro Gly
1               5               10              15

Glu Arg Ala Thr Leu Ser Cys Arg Ala Ser Lys Gly Val Ser Thr Ser
        20              25              30

Gly Tyr Ser Tyr Leu His Trp Tyr Gln Gln Lys Pro Gly Gln Ala Pro
        35              40              45

Arg Leu Leu Ile Tyr Leu Ala Ser Tyr Leu Glu Ser Gly Val Pro Ala
    50              55              60

Arg Phe Ser Gly Ser Gly Ser Gly Thr Asp Phe Thr Leu Thr Ile Ser
65              70              75              80

Ser Leu Glu Pro Glu Asp Phe Ala Val Tyr Tyr Cys Gln His Ser Arg
            85              90              95

Asp Leu Pro Leu Thr Phe Gly Gly Gly Thr Lys Val Glu Ile Lys Arg
        100             105             110

Thr Val Ala Ala Pro Ser Val Phe Ile Phe Pro Pro Ser Asp Glu Gln
        115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
        180             185             190

His Lys Val Tyr Ala Cys Glu Val Thr His Gln Gly Leu Ser Ser Pro
        195             200             205

Val Thr Lys Ser Phe Asn Arg Gly Glu Cys
    210             215
```

<210> SEQ ID NO 32
<211> LENGTH: 120
<212> TYPE: PRT
<213> ORGANISM: Artificial Sequence
<220> FEATURE:
<223> OTHER INFORMATION: anti-PD-1 antibody VH amino Acid sequence

<400> SEQUENCE: 32

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120
```

```
<210> SEQ ID NO 33
<211> LENGTH: 111
<212> TYPE: PRT
<213> ORGANISM: Artificial Sequence
<220> FEATURE:
<223> OTHER INFORMATION: anti-PD-1 antibody VL Amino Acid Sequence
```

<400> SEQUENCE: 33

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110
```

```
<210> SEQ ID NO 34
<211> LENGTH: 5
<212> TYPE: PRT
<213> ORGANISM: Artificial Sequence
<220> FEATURE:
<223> OTHER INFORMATION: anti-PD-1 antibody  VH-CDR1
```

<400> SEQUENCE: 34

```
Asn Tyr Tyr Met Tyr
1               5
```

```
<210> SEQ ID NO 35
<211> LENGTH: 17
<212> TYPE: PRT
<213> ORGANISM: Artificial Sequence
<220> FEATURE:
<223> OTHER INFORMATION: anti-PD-1 antibody  VH-CDR2
```

<400> SEQUENCE: 35

```
Gly Ile Asn Pro Ser Asn Gly Gly Thr Asn Phe Asn Glu Lys Phe Lys
1               5                   10                  15

Asn

<210> SEQ ID NO 36
<211> LENGTH: 11
<212> TYPE: PRT
<213> ORGANISM: Artificial Sequence
<220> FEATURE:
<223> OTHER INFORMATION: anti-PD-1 antibody  VH-CDR3

<400> SEQUENCE: 36

Arg Asp Tyr Arg Phe Asp Met Gly Phe Asp Tyr
1               5                   10

<210> SEQ ID NO 37
<211> LENGTH: 15
<212> TYPE: PRT
<213> ORGANISM: Artificial Sequence
<220> FEATURE:
<223> OTHER INFORMATION: anti-PD-1 antibody  VL-CDR1

<400> SEQUENCE: 37

Arg Ala Ser Lys Gly Val Ser Thr Ser Gly Tyr Ser Tyr Leu His
1               5                   10                  15

<210> SEQ ID NO 38
<211> LENGTH: 7
<212> TYPE: PRT
<213> ORGANISM: Artificial Sequence
<220> FEATURE:
<223> OTHER INFORMATION: anti-PD-1 antibody  VL-CDR2

<400> SEQUENCE: 38

Leu Ala Ser Tyr Leu Glu Ser
1               5

<210> SEQ ID NO 39
<211> LENGTH: 9
<212> TYPE: PRT
<213> ORGANISM: Artificial Sequence
<220> FEATURE:
<223> OTHER INFORMATION: anti-PD-1 antibody  VL-CDR3

<400> SEQUENCE: 39

Gln His Ser Arg Asp Leu Pro Leu Thr
1               5

<210> SEQ ID NO 40
<211> LENGTH: 288
<212> TYPE: PRT
<213> ORGANISM: Homo sapiens

<400> SEQUENCE: 40

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
```

-continued

```
    65                    70                    75                    80

Ala Phe Pro Glu Asp Arg Ser Gln Pro Gly Gln Asp Cys Arg Phe Arg
                85                    90                    95

Val Thr Gln Leu Pro Asn Gly Arg Asp Phe His Met Ser Val Val Arg
                100                   105                   110

Ala Arg Arg Asn Asp Ser Gly Thr Tyr Leu Cys Gly Ala Ile Ser Leu
                115                   120                   125

Ala Pro Lys Ala Gln Ile Lys Glu Ser Leu Arg Ala Glu Leu Arg Val
    130                   135                   140

Thr Glu Arg Arg Ala Glu Val Pro Thr Ala His Pro Ser Pro Ser Pro
145                   150                   155                   160

Arg Pro Ala Gly Gln Phe Gln Thr Leu Val Val Gly Val Val Gly Gly
                165                   170                   175

Leu Leu Gly Ser Leu Val Leu Leu Val Trp Val Leu Ala Val Ile Cys
                180                   185                   190

Ser Arg Ala Ala Arg Gly Thr Ile Gly Ala Arg Arg Thr Gly Gln Pro
                195                   200                   205

Leu Lys Glu Asp Pro Ser Ala Val Pro Val Phe Ser Val Asp Tyr Gly
    210                   215                   220

Glu Leu Asp Phe Gln Trp Arg Glu Lys Thr Pro Glu Pro Pro Val Pro
225                   230                   235                   240

Cys Val Pro Glu Gln Thr Glu Tyr Ala Thr Ile Val Phe Pro Ser Gly
                245                   250                   255

Met Gly Thr Ser Ser Pro Ala Arg Arg Gly Ser Ala Asp Gly Pro Arg
                260                   265                   270

Ser Ala Gln Pro Leu Arg Pro Glu Asp Gly His Cys Ser Trp Pro Leu
                275                   280                   285
```

<210> SEQ ID NO 41
<211> LENGTH: 290
<212> TYPE: PRT
<213> ORGANISM: Homo sapiens

<400> SEQUENCE: 41

```
Met Arg Ile Phe Ala Val Phe Ile Phe Met Thr Tyr Trp His Leu Leu
1               5                    10                    15

Asn Ala Phe Thr Val Thr Val Pro Lys Asp Leu Tyr Val Val Glu Tyr
                20                    25                    30

Gly Ser Asn Met Thr Ile Glu Cys Lys Phe Pro Val Glu Lys Gln Leu
                35                    40                    45

Asp Leu Ala Ala Leu Ile Val Tyr Trp Glu Met Glu Asp Lys Asn Ile
    50                    55                    60

Ile Gln Phe Val His Gly Glu Glu Asp Leu Lys Val Gln His Ser Ser
65                    70                    75                    80

Tyr Arg Gln Arg Ala Arg Leu Leu Lys Asp Gln Leu Ser Leu Gly Asn
                85                    90                    95

Ala Ala Leu Gln Ile Thr Asp Val Lys Leu Gln Asp Ala Gly Val Tyr
                100                   105                   110

Arg Cys Met Ile Ser Tyr Gly Gly Ala Asp Tyr Lys Arg Ile Thr Val
                115                   120                   125

Lys Val Asn Ala Pro Tyr Asn Lys Ile Asn Gln Arg Ile Leu Val Val
    130                   135                   140

Asp Pro Val Thr Ser Glu His Glu Leu Thr Cys Gln Ala Glu Gly Tyr
145                   150                   155                   160
```

-continued

```
Pro Lys Ala Glu Val Ile Trp Thr Ser Ser Asp His Gln Val Leu Ser
            165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290
```

COMBINATION THERAPY FOR CANCER WITH ANTI-B7-H4 ANTIBODIES AND ANTI-PD-1 ANTIBODIES

CROSS-REFERENCE TO RELATED APPLICATIONS

This application is a Continuation Application of PCT/US2019/056210, filed internationally on Oct. 15, 2019, which claims the benefit of priority to U.S. Provisional Application 62/745,464, filed on Oct. 15, 2018, U.S. Provisional Application 62/802,091, filed on Feb. 6, 2019, and U.S. Provisional Application 62/854,494, filed on May 30, 2019, the disclosures of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 204122000501SEQLIST.TXT, date recorded: Apr. 6, 2021, size: 46 KB).

FIELD

The present disclosure relates to methods of administering antibodies that specifically bind to human B7-H4 in combination with a PD-1/PD-L1 antagonist, such as pembrolizumab, for the treatment of diseases such as cancer. Advantageous dose regimens are provided.

1. BACKGROUND

B7-H4 (also known as B7x, B7-S1, and VTCN1) is an immune regulatory molecule that shares homology with other B7 family members, include PD-L1. It is a type I transmembrane protein comprised of both IgV and IgC ectodomains. While B7-H4 expression in healthy tissues is relatively limited at the protein level, B7-H4 is expressed in several solid tumors such as gynecological carcinomas of the breast, ovary, and endometrium. Expression of B7-H4 in tumors tends to correlate with poor prognosis. The receptor for B7-H4 is unknown, but it is believed to be expressed on T cells. B7-H4 is believed to directly inhibit T cell activity.

Given the expression and function of B7-H4, antibodies that specifically bind to B7-H4 are being developed for therapies involving the modulation of B7-H4 activity, e.g., for the treatment of cancer.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to down regulate T cell activation and cytokine secretion upon binding to PD-1. Inhibition of the PD-1/PD-L1 interaction, e.g., by anti-PD-1 or anti-PD-L1 antibodies, mediates potent antitumor activity.

Accordingly, there is a need for efficacious dosing regimens for administration of antibodies that bind to B7-H4 and inhibitors of the PD-1/PD-L1 interaction.

2. SUMMARY

Provided herein are methods of administering anti-B7-H4 antibodies and antigen-binding fragments thereof, in combination with a PD-1/PD-L1 antagonist, using a therapeutically effective dose regimen. Anti-B7-H4 antibodies and antigen-binding fragments thereof may be the 20502 antibody or an antigen-binding fragment thereof; or an antibody or antigen-binding fragment comprising the heavy and light chain variable region CDRs of the 20502 antibody; or an antibody or antigen-binding fragment comprising the heavy and light chain variable regions of the 20502 antibody, including afucosylated forms of any of the foregoing. A PD-1/PD-L1 antagonist may be an anti-PD-1 antibody such as pembrolizumab, or an antibody or antigen-binding fragment comprising the heavy and light chain variable region CDRs of pembrolizumab; or an antibody or antigen-binding fragment comprising the heavy and light chain variable regions of pembrolizumab.

In certain aspects, a method of treating a solid tumor in a human subject comprises administering to the subject (a) about 0.1 to about 20 mg/kg of an antibody or antigen-binding fragment thereof that specifically binds to human B7-H4 and comprises the heavy chain variable region (VH) complementarity determining region (CDR) 1, VH CDR2, VH CDR3 and light chain variable region (VL) CDR1, VL CDR2, and VL CDR3 sequences of the 20502 antibody; and (b) about 200 mg of pembrolizumab. In certain embodiments, (a) and (b) are administered concurrently or sequentially.

In certain aspects, a method of treating a solid tumor in a human subject comprises administering to the subject (a) a pharmaceutical composition comprising (i) antibodies or antigen-binding fragment thereof, wherein the antibodies or antigen-binding fragments thereof specifically bind to human B7-H4 and comprise the heavy chain variable region (VH) complementarity determining region (CDR) 1, VH CDR2, VH CDR3 and light chain variable region (VL) CDR1, VL CDR2, and VL CDR3 sequences of the 20502 antibody and (ii) a pharmaceutically acceptable excipient, wherein at least 95% of the antibodies or antigen-binding fragments thereof in the composition are afucosylated, and wherein about 0.1 to about 20 mg/kg of the antibodies or antigen-binding fragments thereof are administered; and (b) a pharmaceutical composition comprising pembrolizumab, wherein about 200 mg of pembrolizumab is administered. In certain embodiments, (a) and (b) are administered concurrently or sequentially.

In certain aspects, the CDRs of the antibodies or antigen-binding fragments are the Kabat-defined CDRs, the Chothia-defined CDRs, or the AbM-defined CDRs. In certain aspects, the VH CDR1, VH CDR2, VH CDR3, VL CDR1, VL CDR2, and CDR3 sequences comprise the amino acid sequences set forth in SEQ ID NOs: 5-10, respectively.

In certain aspects, about 20 mg/kg or 20 mg/kg of the anti-B7-H4 antibody or antigen-binding fragment thereof is administered to the subject. In certain aspects, about 10 mg/kg or 10 mg/kg of the anti-B7-H4 antibody or antigen-binding fragment thereof is administered to the subject. In certain aspects, about 3 mg/kg or 3 mg/kg of the anti-B7-H4 antibody or antigen-binding fragment thereof is administered to the subject. In certain aspects, about 1 mg/kg or 1 mg/kg of the anti-B7-H4 antibody or antigen-binding fragment thereof is administered to the subject. In certain aspects, about 0.3 mg/kg or 0.3 mg/kg of the anti-B7-H4 antibody or antigen-binding fragment thereof is administered to the subject. In certain aspects, about 0.1 mg/kg or 0.1 mg/kg of the anti-B7-H4 antibody or antigen-binding fragment thereof is administered to the subject.

In certain aspects, the anti-B7-H4 antibody or antigen-binding fragment thereof and/or pembrolizumab are administered about once every three weeks.

In certain aspects, the anti-B7-H4 antibody or antigen-binding fragment thereof and/or pembrolizumab are administered intravenously.

In certain aspects, B7-H4 has been detected in the solid tumor using immunohistochemistry (IHC) prior to the administration.

In certain aspects, the anti-B7-H4 antibody or antigen-binding fragment thereof comprises a VH comprising the amino acid sequence set forth in SEQ ID NO:11 and/or a VL comprising the amino acid sequence set forth in SEQ ID NO:12. In certain aspects, the anti-B7-H4 antibody or antigen-binding fragment comprises a heavy chain constant region and/or a light chain constant region. In certain aspects, the heavy chain constant region is a human immunoglobulins IgG1 heavy chain constant region and/or the light chain constant region is a human immunoglobulin IgGκ light chain constant region. In certain aspects, the antibody or antigen-binding fragment thereof comprises a heavy chain constant region comprising the amino acid sequence set forth in SEQ ID NO:25 and/or a light chain constant region comprising the amino acid sequence set forth in SEQ ID NO:23. In certain aspects, the anti-B7-H4 antibody or antigen-binding fragment thereof comprises a heavy chain comprising the amino acid sequence set forth in SEQ ID NO:21 and/or a light chain comprising the amino acid sequence set forth in SEQ ID NO: 22.

In certain aspects, the antibody or antigen-binding fragment thereof is a human antibody or antigen-binding fragment thereof.

In certain aspects, the anti-B7-H4 antibody or antigen-binding fragment thereof is afucosylated.

In certain aspects, the antibody or antigen-binding fragment thereof is a full length antibody. In certain aspects, the antibody or antigen-binding fragment thereof is an antigen-binding fragment. In certain aspects, the antigen-binding fragment comprises or is a Fab, Fab', F(ab')$_2$, single chain Fv (scFv), disulfide linked Fv, V-NAR domain, IgNar, intra-body, IgGΔCH2, minibody, F(ab')$_3$, tetrabody, triabody, diabody, single-domain antibody, DVD-Ig, Fcab, mAb2, (scFv)$_2$, or scFv-Fc.

In certain aspects, fucosylation is undetectable in the composition comprising anti-B7-H4 antibodies.

In certain aspects, the solid tumor expresses B7-H4.

In certain aspects, the solid tumor is unresectable, locally advanced, or metastatic.

In certain aspects, the solid tumor is selected from the group consisting of breast cancer, ductal carcinoma, endometrial carcinoma, ovarian cancer, urothelial cancer, non-small cell lung cancer, pancreatic cancer, thyroid cancer, kidney cancer and bladder cancer. In certain aspects, the solid tumor is breast cancer, ovarian cancer, endometrial cancer, or urothelial cancer. In certain aspects, the breast cancer is advanced breast cancer. In certain aspects, the breast cancer is HER2-negative. In certain aspects, the breast cancer is triple negative breast cancer. In certain aspects, the breast cancer is hormone receptor (HR)-positive breast cancer. In certain aspects, the non-small cell lung cancer is squamous cell carcinoma. In certain aspects, the subject has not received prior therapy with a PD-1/PD-L1 antagonist.

In certain aspects, the method further comprises monitoring the number of immune cells in the tumor. In certain aspects, the method further comprises monitoring the number of natural killer (NK) cells, CD4+ cells, and/or CD8+ cells in the tumor. In certain aspects, the method further comprises monitoring cytokine levels in the subject. In certain aspects, the method further comprises monitoring IL-2, IL-6, IL-10, TNF, and/or interferon gamma (IFNγ) levels in the subject.

In certain aspects, administration of the anti-B7-H4 antibody or antigen-binding fragment thereof and the anti-PD-1 antibody or antigen-binding fragment thereof produces a synergistic effect.

In certain aspects, a method of treating a solid tumor in a human subject comprises administering to the subject (i) about 20 mg/kg of an anti-B7-H4 antibody that specifically binds to human B7-H4 and comprises a VH comprising the amino acid sequence of SEQ ID NO:11 and a VL comprising the amino acid sequence of SEQ ID NO: 12; and (ii) about 200 mg of an anti-PD-1 antibody comprising a VH comprising the amino acid sequence of SEQ ID NO:32 and a VL comprising the amino acid sequence of SEQ ID NO:33, wherein the anti-B7-H4 antibody and the anti-PD-1 antibody are administered intravenously about once every three weeks.

In certain aspects, a method of treating a solid tumor in a human subject comprises administering to the subject (a) a pharmaceutical composition comprising (i) anti-B7-H4 antibodies that specifically bind to human B7-H4 and comprise a VH comprising the amino acid sequence of SEQ ID NO:11 and a VL comprising the amino acid sequence of SEQ ID NO:12 and (ii) a pharmaceutically acceptable excipient, wherein at least 95% of the anti-B7-H4 antibodies thereof in the composition are afucosylated, and wherein about 20 mg/kg of the antibodies are administered; and (b) a pharmaceutical composition comprising an anti-PD-1 antibody or antigen-binding fragment thereof comprising a VH comprising the amino acid sequence of SEQ ID NO:32 and a VL comprising the amino acid sequence of SEQ ID NO:33 and a pharmaceutically acceptable excipient, wherein about 200 mg of the antibody or antigen-binding fragment is administered, wherein the anti-B7-H4 antibody and the anti-PD-1 antibody are administered intravenously about once every three weeks.

In certain aspects, the anti-B7-H4 antibody comprises a heavy chain comprising the amino acid sequence set forth in SEQ ID NO:21 and a light chain comprising the amino acid sequence set forth in SEQ ID NO:22. In certain aspects, the anti-PD-1 antibody comprises a heavy chain comprising the amino acid sequence set forth in SEQ ID NO:30 and a light chain comprising the amino acid sequence set forth in SEQ ID NO:31.

In certain aspects, the solid tumor is breast cancer, optionally wherein the breast cancer is triple negative breast cancer, or ovarian cancer.

3. BRIEF DESCRIPTION OF THE FIGURES

FIGS. 1A, 1B, and 1C show in vivo anti-tumor efficacy of an anti-B7-H4 antibody in combination with an anti-PD-1 antibody. (See Example 4.)

4. DETAILED DESCRIPTION

Figures 1A, 1B, 1C:
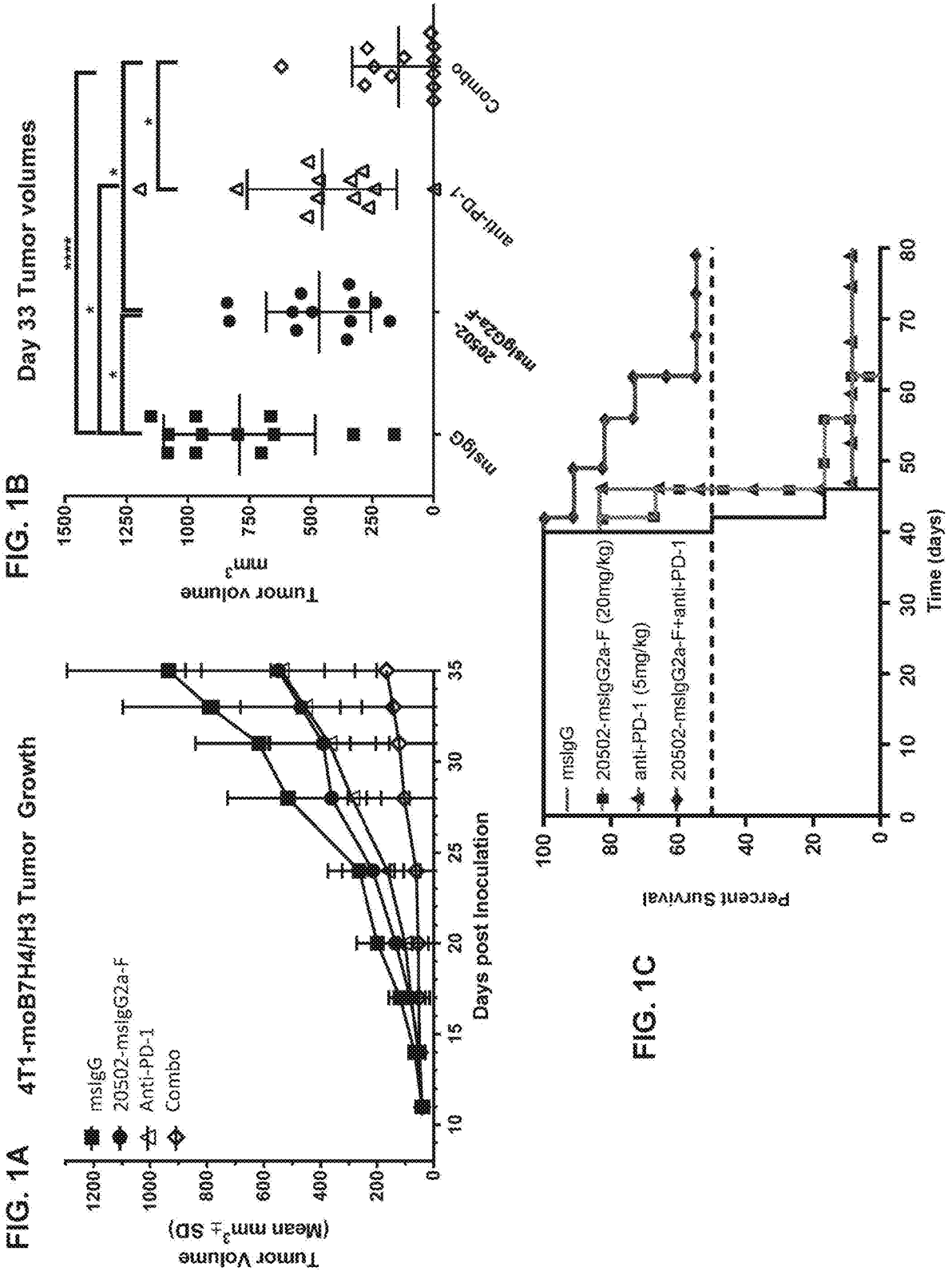

Provided herein are methods of administering antibodies (e.g., monoclonal antibodies) and antigen-binding fragments thereof that specifically bind to B7-H4 (e.g., human B7-H4), in combination with a PD-1/PD-L1 antagonist (e.g., pembrolizumab). The anti-B7-H4 antibodies and antigen-binding fragments thereof can be administered in combination with a PD-1/PD-L1 antagonist (e.g., pembrolizumab), for example, to treat a solid tumor in a subject. In a particular embodiment, about 20 mg/kg, about 10 mg/kg, about 3 mg/kg, about 1 mg/kg, about 0.3 mg/kg, or about 0.1 mg/kg of the antibody or antigen-binding fragment thereof is administered in combination with about 200 mg of pembrolizumab to the subject, e.g., wherein the administration occurs about every three weeks.

4.1 Terminology

As used herein, the term "B7-H4" refers to mammalian B7-H4 polypeptides including, but not limited to, native B7-H4 polypeptides and isoforms of B7-H4 polypeptides. "B7-H4" encompasses full-length, unprocessed B7-H4 polypeptides as well as forms of B7-H4 polypeptides that result from processing within the cell. As used herein, the term "human B7-H4" refers to a polypeptide comprising the amino acid sequence of SEQ ID NO:1. A "B7-H4 polynucleotide," "B7-H4 nucleotide," or "B7-H4 nucleic acid" refer to a polynucleotide encoding B7-H4.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, chimeric antibodies, humanized antibodies, human antibodies, fusion proteins comprising an antibody, and any other modified immunoglobulin molecule so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgAQ1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

The term "antibody fragment" refers to a portion of an intact antibody. An "antigen-binding fragment," "antigen-binding domain," or "antigen-binding region," refers to a portion of an intact antibody that binds to an antigen. An antigen-binding fragment can contain an antigen recognition site of an intact antibody (e.g., complementarity determining regions (CDRs) sufficient to specifically bind antigen). Examples of antigen-binding fragments of antibodies include, but are not limited to Fab, Fab', F(ab')$_2$, and Fv fragments, linear antibodies, and single chain antibodies. An antigen-binding fragment of an antibody can be derived from any animal species, such as rodents (e.g., mouse, rat, or hamster) and humans or can be artificially produced.

The terms "anti-B7-H4 antibody," "B7-H4 antibody" and "antibody that binds to B7-H4" refer to an antibody that is capable of specifically binding B7-H4 with sufficient affinity such that the antibody is useful as a diagnostic and/or therapeutic agent in targeting B7-H4. As used herein, the terms "specifically binding," "immunospecifically binding," "immunospecifically recognizing," and "specifically recognizing" are analogous terms in the context of antibodies or antigen-binding fragments thereof. These terms indicate that the antibody or antigen-binding fragment thereof binds to an epitope via its antigen-binding domain and that the binding entails some complementarity between the antigen-binding domain and the epitope. Accordingly, an antibody that "specifically binds" to human B7-H4 (SEQ ID NO:1) may also bind to B7-H4 from other species (e.g., cynomolgus monkey, mouse, and/or rat B7-H4) and/or B7-H4 proteins produced from other human alleles, but the extent of binding to an un-related, non-B7-H4 protein (e.g., other B7 protein family members such as PD-L1) is less than about 10% of the binding of the antibody to B7-H4 as measured, e.g., by a radioimmunoassay (RIA). In a specific embodiment, provided herein is an antibody or antigen-binding fragment thereof that specifically binds to human, cynomolgus monkey, mouse, and rat B7-H4.

A "monoclonal" antibody or antigen-binding fragment thereof refers to a homogeneous antibody or antigen-binding fragment population involved in the highly specific binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

As used herein, the terms "variable region" or "variable domain" are used interchangeably and are common in the art. The variable region typically refers to a portion of an antibody, generally, a portion of a light or heavy chain, typically about the amino-terminal 110 to 120 amino acids or 110 to 125 amino acids in the mature heavy chain and about 90 to 115 amino acids in the mature light chain, which differ in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

The term "Kabat numbering" and like terms are recognized in the art and refer to a system of numbering amino acid residues in the heavy and light chain variable regions of an antibody or an antigen-binding fragment thereof. In certain aspects, CDRs can be determined according to the Kabat numbering system (see, e.g., Kabat E A & Wu T T (1971) Ann NY Acad Sci 190:382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

TABLE 1

| Loop | Kabat | AbM | Chothia |
| --- | --- | --- | --- |
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 (Kabat Numbering) |
| H1 | H31-H35 | H26-H35 | H26-H32 (Chothia Numbering) |
| H2 | H50-H65 | H50-H58 | H52-H56 |
| H3 | H95-H102 | H95-H102 | H95-H102 |

As used herein, the term "constant region" and "constant domain" are interchangeable and have their common meanings in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain. In certain aspects, an antibody or antigen-binding fragment comprises a constant region or portion thereof that is sufficient for antibody-dependent cell-mediated cytotoxicity (ADCC).

As used herein, the term "heavy chain" when used in reference to an antibody can refer to any distinct type, e.g., alpha (a), delta (8), epsilon (8), gamma (γ), and mu (u), based on the amino acid sequence of the constant domain, which give rise to IgA, IgD, IgE, IgG, and IgM classes of antibodies, respectively, including subclasses of IgG, e.g., IgG1, IgG2, IgG3, and IgG4. Heavy chain amino acid sequences are well known in the art. In specific embodiments, the heavy chain is a human heavy chain.

As used herein, the term "light chain" when used in reference to an antibody can refer to any distinct type, e.g., kappa (κ) or lambda (2) based on the amino acid sequence of the constant domains. Light chain amino acid sequences are well known in the art. In specific embodiments, the light chain is a human light chain.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g. mouse, rat, rabbit, etc.) with the desired specificity, affinity, and capability while the constant regions are homologous to the sequences in antibodies or antigen-binding fragments thereof derived from another (usually human) to avoid eliciting an immune response in that species.

The term "humanized" antibody or antigen-binding fragment thereof refers to forms of non-human (e.g. murine) antibodies or antigen-binding fragments that are specific immunoglobulin chains, chimeric immunoglobulins, or fragments thereof that contain minimal non-human (e.g., murine) sequences. Typically, humanized antibodies or antigen-binding fragments thereof are human immunoglobulins in which residues from the complementary determining region (CDR) are replaced by residues from the CDR of a non-human species (e.g. mouse, rat, rabbit, hamster) that have the desired specificity, affinity, and capability ("CDR grafted") (Jones et al., Nature 321:522-525 (1986); Riechmann et al., Nature 332:323-327 (1988); Verhoeyen et al., Science 239:1534-1536 (1988)). In some instances, certain Fv framework region (FR) residues of a human immunoglobulin are replaced with the corresponding residues in an antibody or fragment from a non-human species that has the desired specificity, affinity, and capability. The humanized antibody or antigen-binding fragment thereof can be further modified by the substitution of additional residues either in the Fv framework region and/or within the non-human CDR residues to refine and optimize antibody or antigen-binding fragment thereof specificity, affinity, and/or capability. In general, the humanized antibody or antigen-binding fragment thereof will comprise variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., Proc. Natl. Acad. Sci., USA, 91 (3): 969-973 (1994), and Roguska et al., Protein Eng. 9 (10): 895-904 (1996). In some embodiments, a "humanized antibody" is a resurfaced antibody.

The term "human" antibody or antigen-binding fragment thereof means an antibody or antigen-binding fragment thereof having an amino acid sequence derived from a human immunoglobulin gene locus, where such antibody or antigen-binding fragment is made using any technique known in the art. This definition of a human antibody or antigen-binding fragment thereof includes intact or full-length antibodies and fragments thereof.

An "afucosylated" antibody or antigen-binding fragment thereof or an antibody or antigen-binding fragment thereof "lacking fucose" refers to an IgG1 or IgG3 isotype antibody or antigen-binding fragment thereof that lacks fucose in its constant region glycosylation. Glycosylation of human IgG1 or IgG3 occurs at Asn297 as core fucosylated biantennary complex oligosaccharide glycosylation terminated with up to 2 Gal residues. In some embodiments, an afucosylated antibody lacks fucose at Asn297. These structures are designated as G0, G1 (a 1,6 or a 1,3), or G2 glycan residues, depending on the amount of terminal Gal residues. See, e.g., Raju, T. S., BioProcess Int. 1:44-53 (2003). CHO type glycosylation of antibody Fc is described, e.g., in Routier, F. FL, Glycoconjugate J. 14:201-207 (1997).

Methods of measuring fucose include any methods known in the art. For purposes herein, fucose is detected by the method described in Example 1 of WO2015/017600, which is herein incorporated by reference in its entirety. Briefly, glycan analysis is performed by releasing glycans from the antibody (e.g., by enzymatic release), labeling the glycans with anthranilic acid (2-AA), and then purifying the labeled glycans. Normal phase HPLC with fluorescent detection is used to separate the glycans and measure the relative amount of each glycan in the antibody. The glycans may be positively identified as lacking or including fucose by mass spectrometry. In some embodiments, fucose is undetectable in a composition comprising a plurality of afucosylated antibodies or antigen-binding fragments thereof. In some embodiments, an afucosylated antibody or antigen-binding fragment thereof has enhanced affinity for Fc gamma RIIIA. In some embodiments, an afucosylated antibody or antigen-binding fragment thereof has enhanced affinity for Fc gamma RIIIA(V158). In some embodiments, an afucosylated antibody or antigen-binding fragment thereof has enhanced affinity for Fc gamma RIIIA(F158).

"Binding affinity" generally refers to the strength of the sum total of non-covalent interactions between a single binding site of a molecule (e.g., an antibody or antigen-binding fragment thereof) and its binding partner (e.g., an antigen). Unless indicated otherwise, as used herein, "binding affinity" refers to intrinsic binding affinity which reflects a 1:1 interaction between members of a binding pair (e.g., antibody or antigen-binding fragment thereof and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody or antigen-binding fragment thereof to an antigen, and $k_{off}$ refers to the dissociation of, e.g., an antibody or antigen-binding fragment thereof from an antigen. The $k_{on}$ and $k_{off}$ can be determined by techniques known to one of ordinary skill in the art, such as BIAcore® or KinExA.

As used herein, an "epitope" is a term in the art and refers to a localized region of an antigen to which an antibody or antigen-binding fragment thereof can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody or antigen-binding fragment thereof specifically binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegć R et al., (1994) Acta Crystallogr D Biol Crystallogr 50 (Pt 4): 339-350; McPherson A (1990) Eur J Biochem 189:1-23; Chayen N E (1997) Structure 5:1269-1274; McPherson A (1976) J Biol Chem 251:6300-6303). Antibody/antigen-binding fragment thereof:antigen crystals can be studied using well known X-ray diffraction techniques and can be refined using computer software such as X-PLOR (Yale University, 1992, distributed by Molecular Simulations, Inc.; see, e.g., Meth Enzymol (1985) volumes 114 & 115, eds Wyckoff H W et al.,; U.S. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter C W; Roversi P et al., (2000) Acta Crystallogr D Biol Crystallogr 56 (Pt 10): 1316-1323). Mutagenesis mapping studies can be accomplished using any method known to one of skill in the art. See, e.g., Champe M et al., (1995) J Biol Chem 270:1388-1394 and Cunningham B C & Wells J A (1989) Science 244:1081-1085 for a description of mutagenesis techniques, including alanine scanning mutagenesis techniques.

The terms "programmed cell death protein 1" and "PD-1" refer to an immunoinhibitory receptor belonging to the CD28 family. PD-1 is expressed predominantly on previously activated T-cells in vivo, and binds to two ligands, PD-L1 and PD-L2. The term "PD-1" as used herein includes human PD-1 (hPD-1), naturally occurring variants and isoforms of hPD-1, and species homologs of hPD-1.

The terms "programmed cell death 1 ligand 1" and "PD-L1" refer to one of two cell surface glycoprotein ligands for PD-1 (the other being PD-L2) that down regulate T-cell activation and cytokine secretion upon binding to PD-1. The term "PD-L1" as used herein includes human PD-L1 (hPD-L1), naturally occurring variants and isoforms of hPD-1, and species homologs of hPD-L1.

The term "PD-1/PD-L1 antagonist" refers to a moiety that disrupts the PD-1/PD-L1 signaling pathway. In some embodiments, the antagonist inhibits the PD-1/PD-L1 signaling pathway by binding to PD-1 and/or PD-L1. In some embodiments, the PD-1/PD-L1 antagonist also binds to PD-L2. In some embodiments, a PD-1/PD-L1 antagonist blocks binding of PD-1 to PD-L1 and optionally PD-L2. Nonlimiting exemplary PD-1/PD-L1 antagonists include PD-1 antagonists, such as antibodies that bind to PD-1, e.g., nivolumab (OPDIVO) and pembrolizumab (KEYTRUDA); PD-L1 antagonists, such as antibodies that bind to PD-L1 (e.g., atezolizumab (TECENTRIQ), durvalumab and avelumab); fusion proteins, such as AMP-224; and peptides, such as AUR-012.

"Pembrolizumab" refers to the humanized anti-PD-1 monoclonal antibody that is the active ingredient in the commercial pharmaceutical preparation referred to as KEYTRUDA®, marketed by Merck & Co.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure. As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

As used herein, the term "host cell" can be any type of cell, e.g., a primary cell, a cell in culture, or a cell from a cell line. In specific embodiments, the term "host cell" refers to a cell transfected with a nucleic acid molecule and the progeny or potential progeny of such a cell. Progeny of such a cell may not be identical to the parent cell transfected with the nucleic acid molecule, e.g., due to mutations or environmental influences that may occur in succeeding generations or integration of the nucleic acid molecule into the host cell genome.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The terms "administer," "administering," "administration," and the like, as used herein, refer to methods that may be used to enable delivery of a drug, e.g., an anti-B7-H4 antibody or antigen-binding fragment thereof to the desired site of biological action (e.g., intravenous administration). Administration techniques that can be employed with the agents and methods described herein are found in e.g., Goodman and Gilman, *The Pharmacological Basis of Therapeutics*, current edition, Pergamon; and Remington's, *Pharmaceutical Sciences*, current edition, Mack Publishing Co., Easton, Pa.

As used herein, the terms "subject" and "patient" are used interchangeably. The subject can be an animal. In some embodiments, the subject is a mammal such as a non-human animal (e.g., cow, pig, horse, cat, dog, rat, mouse, monkey or other primate, etc.). In some embodiments, the subject is a cynomolgus monkey. In some embodiments, the subject is a human.

The term "therapeutically effective amount" refers to an amount of a drug, e.g., an anti-B7-H4 antibody or antigen-binding fragment thereof, effective to treat a disease or disorder in a subject. In the case of cancer, the therapeutically effective amount of the drug can reduce the number of cancer cells; reduce the tumor size or burden; inhibit, to some extent, cancer cell infiltration into peripheral organs; inhibit, to some extent, tumor metastasis; inhibit, to some extent, tumor growth; relieve, to some extent, one or more of the symptoms associated with the cancer; and/or result in a favorable response such as increased progression-free survival (PFS), disease-free survival (DFS), overall survival (OS), complete response (CR), partial response (PR), or, in some cases, stable disease (SD), a decrease in progressive disease (PD), a reduced time to progression (TTP), or any combination thereof. To the extent the drug can prevent growth and/or kill existing cancer cells, it can be cytostatic and/or cytotoxic.

Terms such as "treating," "treatment," "to treat," "alleviating," and "to alleviate" refer to therapeutic measures that cure, slow down, lessen symptoms of, and/or halt progression of a pathologic condition or disorder. Thus, those in need of treatment include those already diagnosed with or suspected of having the disorder. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; increased progression-free survival (PFS), disease-free survival (DFS), overall survival (OS), complete response (CR), partial response (PR), stable disease (SD), a decrease in progressive disease (PD), a reduced time to progression (TTP), or any combination thereof.

The terms "cancer" and "cancerous" refer to or describe the physiological condition in mammals in which a population of cells are characterized by unregulated cell growth. Examples of cancer include, but are not limited to, gynecological cancers (e.g., breast cancer (including triple negative breast cancer, hormone receptor (HR)-positive breast cancer, ductal carcinoma, ovarian cancer, and endometrial cancer)), non-small cell lung cancer, pancreatic cancer, thyroid cancer, kidney cancer (e.g., renal cell carcinoma) and bladder cancer (e.g., urothelial cell carcinoma). The cancer can be a "cancer that expresses B7-H4" or a "B7-H4 expressing cancer" or a "B7-H4 positive cancer". Such terms refer to a cancer comprising cells that express B7-H4. The cancer can be a solid tumor that expresses B7-H4. The cancer may be a primary tumor or may be advanced or metastatic cancer.

A "refractory" cancer is one that progresses even though an anti-tumor treatment, such as a chemotherapy, is administered to the cancer patient.

A "recurrent" cancer is one that has regrown, either at the initial site or at a distant site, after a response to initial therapy.

As demonstrated herein, administration of an anti-B7-H4 antibody or antigen-binding fragment thereof and an anti-PD-1 antibody or antigen-binding fragment thereof can provide "synergy" or be "synergistic," i.e., the effect achieved when the active ingredients are used together is greater than the sum of the effects that results from using the active ingredients separately. A synergistic effect can be attained when the active ingredients are: (1) co-formulated and administered or delivered simultaneously in a combined, unit dosage formulation; (2) delivered serially, by alternation, or in parallel as separate formulations; or (3) by some other regimen. When delivered in alternation therapy, a synergistic effect can be attained when the compounds are administered or delivered sequentially, e.g., by different injections in separate syringes.

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided. In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited are not changed by the presence of more than that which is recited, but excludes prior art embodiments Unless specifically stated or obvious from context, as used herein, the term "or" is understood to be inclusive. The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the terms "about" and "approximately," when used to modify a numeric value or numeric range, indicate that deviations of 5% to 10% above and 5% to 10% below the value or range remain within the intended meaning of the recited value or range.

Any compositions or methods provided herein can be combined with one or more of any of the other compositions and methods provided herein.

4.2 Methods of Treating Cancer

In one aspect, presented herein are methods for treating cancer in a human subject comprising administering to a subject in need thereof (i) an anti-B7-H4 antibody or antigen-binding fragment thereof described herein or a pharmaceutical composition thereof as described herein, in combination with (ii) a PD-1/PD-L1 inhibitor described herein or a pharmaceutical composition thereof as described herein, and wherein (i) and (ii) are administered concurrently or sequentially. For administration "concurrently," in some embodiments, the agents as in (i) and (ii) are administered as separate formulations on the same day, with one being administered after the other; or in other embodiments, the agents as in (i) and (ii) are mixed together prior to administration and thus administered as a mixture. For example, in some embodiments, the agents as in (i) and (ii) may be packaged and stored in the same vial (i.e., fixed dose formulation), or alternatively, vials containing each separate agent may be mixed together just prior to administration. For administration "sequentially," the agents as in (i) and (ii) are administered as separate formulations on different days. In various embodiments, the agents may be administered in vivo by various routes, including, but not limited to, intravenous.

The combination of the anti-B7-H4 antibody or antigen-binding fragment thereof and the PD-1/PD-L1 inhibitor can be synergistic.

In one aspect, the PD-1 inhibitor is pembrolizumab. The heavy and light chain sequences of pembrolizumab are listed in the following table. In the context of the heavy and light chain sequences, the CDR sequences are shown in bold, and the variable region sequences are underlined.

TABLE 2

Pembrolizumab sequences

| Domain | Amino Acid Sequence (SEQ ID NO) |
|---|---|
| Heavy | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSSASTKGPSVF PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEFLGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLGK (SEQ ID NO: 30) |
| Light | EIVLTQSPATLSLSPGERATLSCRASKGVSTSGYSYLHWYQQK PGQAPRLLIYLASYLESGVPARFSGSGSGTDFTLTISSLEPED FAVYYCQHSRDLPLTFGGGTKVEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNR GEC (SEQ ID NO: 31) |
| VH | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSS (SEQ ID NO: 32) |
| VL | EIVLTQSPATLSLSPGERATLSCRASKGVSTSGYSYLHWYQQK PGQAPRLLIYLASYLESGVPARFSGSGSGTDFTLTISSLEPED FAVYYCQHSRDLPLTFGGGTKVEIK (SEQ ID NO: 33) |
| VH-CDR1 | NYYMY (SEQ ID NO: 34) |
| VH-CDR2 | GINPSNGGTNFNEKFKN (SEQ ID NO: 35) |
| VH-CDR3 | RDYRFDMGFDY (SEQ ID NO: 36) |
| VL-CDR1 | RASKGVSTSGYSYLH (SEQ ID NO: 37) |
| VL-CDR2 | LASYLES (SEQ ID NO: 38) |
| VL-CDR3 | QHSRDLPLT (SEQ ID NO: 39) |

In one aspect, the PD-1 inhibitor is antibody or antigen-binding fragment comprising the heavy and light chain variable region CDRs of pembrolizumab; or an antibody or antigen-binding fragment comprising the heavy and light chain variable regions of pembrolizumab.

In one aspect, a method of treating cancer in a human subject comprises administering to a subject in need thereof (i) an anti-B7-H4 antibody or antigen-binding fragment thereof described herein or a pharmaceutical composition thereof as described herein, wherein about 0.005 to about 20 mg/kg of the anti-B7-H4 antibody or antigen-binding fragment of is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks.

In one aspect, a method of treating cancer in a human subject comprises administering to a subject in need thereof (i) an anti-B7-H4 antibody or antigen-binding fragment thereof described herein or a pharmaceutical composition thereof as described herein, wherein about 0.1 mg/kg of the anti-B7-H4 antibody or antigen-binding fragment thereof is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein about 0.3 mg/kg of the anti-B7-H4 antibody or antigen-binding fragment thereof is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein about 1 mg/kg of the anti-B7-H4 antibody or antigen-binding fragment thereof is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein about 3 mg/kg of the anti-B7-H4 antibody or antigen-binding fragment of is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein about 10 mg/kg of the anti-B7-H4 antibody or antigen-binding fragment thereof is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein about 20 mg/kg of the anti-B7-H4 antibody or antigen-binding fragment thereof is administered, and (ii) pembrolizumab or a pharmaceutical composition thereof as described herein, wherein about 200 mg of pembrolizumab is administered, and wherein (i) and (ii) are administered concurrently or sequentially at a frequency of, e.g., about once every three weeks.

In one aspect, a method of treating cancer in a human subject comprises administering to a subject in need thereof (i) an anti-B7-H4 antibody or antigen-binding fragment thereof described herein or a pharmaceutical composition thereof as described herein, wherein 0.1 mg/kg of the anti-B7-H4 antibody or antigen-binding fragment thereof is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein 0.3 mg/kg of the anti-B7-H4 antibody or antigen-binding fragment thereof is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein 1 mg/kg of the anti-B7-H4 antibody or antigen-binding fragment thereof is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein 3 mg/kg of the anti-B7-H4 antibody or antigen-binding fragment of is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein 10 mg/kg of the anti-B7-H4 antibody or antigen-binding fragment thereof is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks. In one aspect, a method of treating cancer in a human subject comprises administering to a subject in need thereof (i) an anti-B7-H4 antibody or antigen-binding fragment thereof described herein or a pharmaceutical composition thereof as described herein, wherein 20 mg/kg of the anti-B7-H4 antibody or antigen-binding fragment thereof is administered, and (ii) pembrolizumab or a pharmaceutical composition thereof as described herein, wherein 200 mg of pembrolizumab is administered, and wherein (i) and (ii) are administered concurrently or sequentially at a frequency of once every three weeks.

In certain embodiments of the methods provided herein, the anti-B7-H4 antibody or antigen-binding fragment thereof, or the pharmaceutical composition comprising anti-B7-H4 antibodies or antigen-binding fragments thereof, is administered intravenously. In certain embodiments of the methods provided herein, pembrolizumab or the pharmaceutical composition thereof is administered intravenously.

In certain embodiments, provided herein are methods of treating a cancer selected from the group consisting of: breast cancer (e.g., advanced breast cancer, triple negative breast cancer, hormone receptor (HR)-positive breast cancer, or ductal carcinoma), endometrial carcinoma, ovarian cancer, urothelial cancer, non-small cell lung cancer (e.g., squamous cell carcinoma), head and neck squamous cell cancer (HNSCC), Hodgkin's lymphoma (e.g., classical Hodgkin lymphoma), melanoma, pancreatic cancer, thyroid cancer, kidney cancer (e.g., renal cell carcinoma), bladder cancer (e.g., urothelial carcinoma), gastric cancer, cervical cancer and microsatellite instability-high cancer. In a certain embodiment, provided herein are methods of treating advanced breast cancer (including triple-negative breast cancer, hormone receptor (HR)-positive), ovarian cancer, endometrial cancer, or urothelial cancer. In a certain embodiment, provided herein are methods of treating a breast cancer. In a certain embodiment, the breast cancer is triple negative breast cancer. In a certain embodiment, provided herein are methods of treating a hormone-receptor (HR)-positive breast cancer. In a certain embodiment, provided herein are methods of treating an ovarian cancer. In a certain embodiment, provided herein are methods of treating an endometrial cancer. In a certain embodiment, provided herein are methods of treating a urothelial cancer. In a certain embodiment, provided herein are methods of treating a gastro-intestinal cancer. In a certain embodiment, provided herein are methods of treating a gynecologic cancer. In a certain embodiment, provided herein are methods of treating a head and neck cancer. In a certain embodiment, provided herein are methods of treating a genitourinary cancer. In a certain embodiment, provided herein, the subject has not received prior therapy with a PD-1/PD-L1 antagonist. In certain embodiments, such methods comprise administering an anti-B7-H4 antibody or antigen-binding fragment thereof provided herein, or a pharmaceutical composition comprising anti-B7-H4 antibodies or antigen-binding fragments thereof provided herein, in combination with a PD-1/PD-L1 inhibitor or a pharmaceutical composition thereof provided herein, to a patient (e.g., a human patient) in need thereof.

In some embodiments, the cancer is a B7-H4 expressing cancer. In certain embodiments, the cancer is a solid tumor solid tumor that expresses B7-H4. In certain embodiments, B7-H4 has been detected (e.g., using immunohistochemistry (IHC)) in a biological sample obtained from the subject.

A biological sample may be any biological sample obtained from a subject, cell line, tissue, or other source of cells potentially expressing B7-H4. Methods for obtaining tissue biopsies and body fluids from humans are well known in the art. Biological samples include peripheral mononuclear blood cells. A biological sample may also be a blood sample, in which circulating tumor cells (or "CTCs") may express B7-H4 and be detected.

Assaying for the expression level of B7-H4 protein is intended to include qualitatively or quantitatively measuring or estimating the level of a B7-H4 protein in a first biological sample either directly (e.g., by determining or estimating absolute protein level) or relatively (e.g., by comparing to the protein level in a second biological sample). B7-H4 polypeptide expression level in the first biological sample can be measured or estimated and compared to a standard B7-H4 protein level, the standard being determined from a second biological sample that is not diseased or being determined by averaging levels from a population of samples that are not diseased. As will be appreciated in the art, once the "standard" B7-H4 polypeptide level is known, it can be used repeatedly as a standard for comparison.

In another embodiment, an anti-B7-H4 antibody or antigen-binding fragment thereof, or pharmaceutical composition, as described herein is administered to a patient (e.g., a human patient) diagnosed with cancer to increase the proliferation of T cells, CD4+ T cells, or CD8+T cells in the patient. In such embodiment, a PD-1/PD-L1 antagonist as described herein, e.g., pembrolizumab, is also administered to the patient to block binding of PD-1 to PD-L1 and PD-L2 and to activate T cells. In another embodiment, an anti-B7-H4 antibody or antigen-binding fragment thereof, or pharmaceutical composition, is administered to a patient (e.g., a human patient) diagnosed with cancer to increase interferon-gamma (IFNγ) production in the patient. In such embodiment, a PD-1/PD-L1 antagonist as described herein, e.g., pembrolizumab, is also administered to the patient to block binding of PD-1 to PD-L1 and PD-L2 and to activate T cells. In another embodiment, an anti-B7-H4 antibody or antigen-binding fragment thereof, or pharmaceutical composition, is administered to a patient (e.g., a human patient) diagnosed with cancer to block the inhibitory activity of B7-H4 against T cells in the patient. In such embodiment, a PD-1/PD-L1 antagonist as described herein, e.g., pembrolizumab, is also administered to the patient to block binding of PD-1 to PD-L1 and PD-L2 and to activate T cells. In another embodiment, an anti-B7-H4 antibody or antigen-binding fragment thereof, or pharmaceutical composition, is administered to a patient (e.g., a human patient) diagnosed with cancer to deplete B7-H4 expressing cancer cells in the patient. In such embodiment, a PD-1/PD-L1 antagonist as described herein, e.g., pembrolizumab, is also administered to the patient to block binding of PD-1 to PD-L1 and PD-L2 and to activate T cells.

In some embodiments, the present invention relates to an anti-B7-H4 antibody or antigen-binding fragment thereof or pharmaceutical composition provided herein for use in combination with a PD-1/PD-L1 antagonist, such as pembrolizumab or pharmaceutical composition thereof, as a medicament, wherein the medicament is for administration at about 0.1 mg/kg to about 20 mg/kg (e.g., about 0.1 mg/kg, about 0.3 mg/kg, about 1 mg/kg, about 3 mg/kg, about 10 mg/kg, or about 20 mg/kg) of the antibody or antigen-binding fragment thereof, and about 200 mg of the pembrolizumab. In such embodiments, the antibody or antigen-binding fragment thereof and the pembrolizumab may be co-formulated or separately formulated for administration concurrently or sequentially. In some aspects, the present invention relates to an anti-B7-H4 antibody or antigen-binding fragment thereof or pharmaceutical composition provided herein, for use in combination with a PD-1/PD-L1 antagonist, such as pembrolizumab or pharmaceutical composition thereof, in a method for the treatment of cancer wherein about 0.1 mg/kg to about 20 mg/kg (e.g., about 0.1 mg/kg, about 0.3 mg/kg, about 1 mg/kg, about 3 mg/kg, about 10 mg/kg, or about 20 mg/kg) of the antibody or antigen-binding fragment thereof is administered, and about 200 mg of the pembrolizumab is administered, and wherein the administrations are sequential or concurrent. In some aspects, the present invention relates to an ant-B7-H4 antibody or antigen-binding fragment thereof or pharmaceutical composition provided herein, for use in combination with a PD-1/PD-L1 antagonist, such as pembrolizumab, in a method for the treatment of cancer in a subject, comprising administering to the subject about 0.1 mg/kg to about 20 mg/kg (e.g., about 0.1 mg/kg, about 0.3 mg/kg, about 1 mg/kg, about 3 mg/kg, about 10 mg/kg, or about 20 mg/kg) of an antibody or antigen-binding fragment thereof or pharmaceutical composition provided herein, and administering about 200 mg pembrolizumab or a pharmaceutical composition provided herein, wherein the administrations are sequential or concurrent.

In some embodiments, the present invention relates to an anti-B7-H4 antibody or antigen-binding fragment thereof or pharmaceutical composition provided herein for use in combination with a PD-1/PD-L1 antagonist, such as pembrolizumab or pharmaceutical composition thereof, as a medicament, wherein the medicament is for administration at 0.1 mg/kg to 20 mg/kg (e.g., 0.1 mg/kg, 0.3 mg/kg, 1 mg/kg, 3 mg/kg, 10 mg/kg, or 20 mg/kg) of the antibody or antigen-binding fragment thereof, and 200 mg of the pembrolizumab. In such embodiments, the antibody or antigen-binding fragment thereof and the pembrolizumab may be co-formulated or separately formulated for administration concurrently or sequentially. In some aspects, the present invention relates to an anti-B7-H4 antibody or antigen-binding fragment thereof or pharmaceutical composition provided herein, for use in combination with a PD-1/PD-L1 antagonist, such as pembrolizumab or pharmaceutical composition thereof, in a method for the treatment of cancer wherein 0.1 mg/kg to 20 mg/kg (e.g., 0.1 mg/kg, 0.3 mg/kg, 1 mg/kg, 3 mg/kg, 10 mg/kg, or 20 mg/kg) of the antibody or antigen-binding fragment thereof is administered, and 200 mg of the pembrolizumab is administered, and wherein the administrations are sequential or concurrent. In some aspects, the present invention relates to an ant-B7-H4 antibody or antigen-binding fragment thereof or pharmaceutical composition provided herein, for use in combination with a PD-1/PD-L1 antagonist, such as pembrolizumab, in a method for the treatment of cancer in a subject, comprising administering to the subject 0.1 mg/kg to 20 mg/kg (e.g., 0.1 mg/kg, 0.3 mg/kg, 1 mg/kg, 3 mg/kg, 10 mg/kg, or 20 mg/kg) of an antibody or antigen-binding fragment thereof or pharmaceutical composition provided herein, and administering 200 mg pembrolizumab or a pharmaceutical composition provided herein, wherein the administrations are sequential or concurrent.

In certain aspects, the amino acid of human PD-1 is:

```
                                  (SEQ ID NO: 40)
MQIPQAPWPVVWAVLQLGWRPGWFLDSPDRPWNPPTFSPALLVVTEGDNAT

FTCSFSNTSESFVLNWYRMSPSNQTDKLAAFPEDRSQPGQDCRFRVTQLPN

GRDFHMSVVRARRNDSGTYLCGAISLAPKAQIKESLRAELRVTERRAEVPT

AHPSPSPRPAGQFQTLVVGVVGGLLGSLVLLVWVLAVICSRAARGTIGARR

TGQPLKEDPSAVPVFSVDYGELDFQWREKTPEPPVPCVPEQTEYATIVFPS

GMGTSSPARRGSADGPRSAQPLRPEDGHCSWPL.
```

In certain aspects, the amino acid sequence of human PD-L1 is:

```
                                  (SEQ ID NO: 41)
MRIFAVFIFMTYWHLLNAFTVTVPKDLYVVEYGSNMTIECKFPVEKQLDLA

ALIVYWEMEDKNIIQFVHGEEDLKVQHSSYRQRARLLKDQLSLGNAALQIT

DVKLQDAGVYRCMISYGGADYKRITVKVNAPYNKINQRILVVDPVTSEHEL

TCQAEGYPKAEVIWTSSDHQVLSGKTTTTNSKREEKLFNVTSTLRINTTTN

EIFYCTFRRLDPEENHTAELVIPELPLAHPPNERTHLVILGAILLCLGVAL

TFIFRLRKGRMMDVKKCGIQDTNSKKQSDTHLEET.
```

4.3 B7-H4 Antibodies and Antigen-Binding Fragments Thereof

Provided herein are methods of treating cancer in a human subject comprising administering to the subject antibodies (e.g., monoclonal antibodies, such as chimeric, humanized, or human antibodies) and antigen-binding fragments thereof which specifically bind to B7-H4 (e.g., human B7-H4), in combination with a PD-1/PD-L1 antagonist, such as pembrolizumab. Exemplary B7-H4 antibodies and antigen-binding fragments thereof that can be used in the methods provided herein are known in the art. The amino acid sequences for human, cynomolgus monkey, murine, and rat B7-H4 are known in the art and also provided herein as represented by SEQ ID NOs: 1-4, respectively.

```
Human B7-H4:
                                  (SEQ ID NO: 1)
MASLGQILFWSIISIIIILAGAIALIIGFGISGRHSITVTTVASAGNIGED

GILSCTFEPDIKLSDIVIQWLKEGVLGLVHEFKEGKDELSEQDEMFRGRTA

VFADQVIVGNASLRLKNVQLTDAGTYKCYIITSKGKGNANLEYKTGAFSMP

EVNVDYNASSETLRCEAPRWFPQPTVVWASQVDQGANFSEVSNTSFELNSE

NVTMKVVSVLYNVTINNTYSCMIENDIAKATGDIKVTESEIKRRSHLQLLN

SKASLCVSSFFAISWALLPLSPYLMLK

Cynomolgus monkey B7-H4:
                                  (SEQ ID NO: 2)
MASLGQILFWSIISIIFILAGAIALIIGFGISGRHSITVTTVASAGNIGED

GILSCTFEPDIKLSDIVIQWLKEGVIGLVHEFKEGKDELSEQDEMFRGRTA

VFADQVIVGNASLRLKNVQLTDAGTYKCYIITSKGKGNANLEYKTGAFSMP

EVNVDYNASSETLRCEAPRWFPQPTVVWASQVDQGANFSEVSNTSFELNSE

NVTMKVVSVLYNVTINNTYSCMIENDIAKATGDIKVTESEIKRRSHLQLLN

SKASLCVSSFLAISWALLPLAPYLMLK

Murine B7-H4
                                  (SEQ ID NO: 3)
MASLGQIIFWSIINIIIILAGAIALIIGFGISGKHFITVTTFTSAGNIGED

GTLSCTFEPDIKLNGIVIQWLKEGIKGLVHEFKEGKDDLSQQHEMFRGRTA

VFADQVVVGNASLRLKNVQLTDAGTYTCYIRTSKGKGNANLEYKTGAFSMP

EINVDYNASSESLRCEAPRWFPQPTVAWASQVDQGANFSEVSNTSFELNSE

NVTMKVVSVLYNVTINNTYSCMIENDIAKATGDIKVTDSEVKRRSQLQLLN

SGPSPCVFSSAFVAGWALLSLSCCLMLR

Rat B7-H4
                                  (SEQ ID NO: 4)
MASLGQIIFWSIINVIIILAGAIVLIIGFGISGKHFITVTTFTSAGNIGED

GTLSCTFEPDIKLNGIVIQWLKEGIKGLVHEFKEGKDDLSQQHEMFRGRTA

VFADQVVVGNASLRLKNVQLTDAGTYTCYIHTSKGKGNANLEYKTGAFSMP

EINVDYNASSESLRCEAPRWFPQPTVAWASQVDQGANFSEVSNTSFELNSE

NVTMKVVSVLYNVTINNTYSCMIENDIAKATGDIKVTDSEVKRRSQLELLN

SGPSPCVSSVSAAGWALLSLSCCLMLR
```

In certain embodiments, an antibody or antigen-binding fragment thereof for use in the methods described herein specifically binds to human B7-H4. In certain embodiments, an antibody or antigen-binding fragment thereof for use in the methods described herein specifically binds to human and cynomolgus monkey B7-H4. In certain embodiments, an antibody or antigen-binding fragment thereof for use in the methods described herein specifically binds to human, murine, and rat B7-H4. In certain embodiments, an antibody or antigen-binding fragment thereof for use in the methods described herein specifically binds to human, cynomolgus monkey, murine, and rat B7-H4.

B7-H4 contains an IgC ectodomain (amino acids 153-241 of SEQ ID NO:1) and an IgV ectodomain (amino acids 35-146 of SEQ ID NO:1). In certain embodiments, an antibody or antigen-binding fragment thereof for use in the methods described herein specifically binds to the IgV domain of human B7-H4. Accordingly, provided herein are methods of administering antibodies and antigen-binding fragments thereof that specifically bind to a polypeptide consisting of amino acids 35-146 of SEQ ID NO:1.

In certain embodiments, an antibody or antigen-binding fragment thereof for use in the methods described herein specifically binds to human B7-H4 and comprises the six CDRs of the 20502 antibody listed as provided in Tables 3 and 4. "20502" refers to the 20502 antibody, described herein.

TABLE 3

| VH CDR Amino Acid Sequences [1] | | |
|---|---|---|
| Anti-body | VH CDR1 (SEQ ID NO:) | VH CDR2 (SEQ ID NO:) | VH CDR3 (SEQ ID NO:) |
| 20502 | GSIKSGSYYWG (SEQ ID NO: 5) | NIYYSGSTYYNP SLRS (SEQ ID NO: 6) | AREGSYPNQFDP (SEQ ID NO: 7) |

[1] The VH CDRs in Table 1 are determined according to Kabat.

TABLE 4

| VL CDR Amino Acid Sequences [2] | | |
|---|---|---|
| Anti-body | VL CDR1 (SEQ ID NO:) | VL CDR2 (SEQ ID NO:) | VL CDR3 (SEQ ID NO:) |
| 20502 | RASQSVSSNLA (SEQ ID NO: 8) | GASTRAT (SEQ ID NO: 9) | QQYHSFPFT (SEQ ID NO: 10) |

[2] The VL CDRs in Table 2 are determined according to Kabat.

In certain embodiments, an antibody or antigen-binding fragment thereof for use in the methods described herein specifically binds to human B7-H4 and comprises the VH of the 20502 antibody listed in Table 5.

TABLE 5

| Variable Heavy Chain (VH) Amino Acid Sequences |
|---|
| Anti-body VH Amino Acid Sequence (SEQ ID NO) |
| 20502 QLQLQESGPGLVKPSETLSLTCTVSGGSIKSGSYYWGWIRQPP GKGLEWIGNIYYSGSTYYNPSLRSRVTISVDTSKNQFSLKLSS VTAADTAVYYCAREGSYPNQFDPWGQGTLVTVSS (SEQ ID NO: 11) |

In certain embodiments, an antibody or antigen-binding fragment thereof for use in the methods described herein specifically binds to human B7-H4 and comprises the VL of the 20502 antibody listed in Table 6.

TABLE 6

| Variable Light Chain (VL) Amino Acid Sequences |
|---|
| Anti-body VL Amino Acid Sequence (SEQ ID NO) |
| 20502 EIVMTQSPATLSVSPGERATLSCRASQSVSSNLAWYQQKPGQA PRLLIYGASTRATGIPARFSGSGSGTEFTLTISSLQSEDFAVY YCQQYHSFPFTFGGGTKVEIK (SEQ ID NO: 12) |

In certain embodiments, an antibody or antigen-binding fragment thereof for use in the methods described herein specifically binds to human B7-H4 and comprises the VH and the VL of the 20502 antibody listed in Tables 5 and 6.

In certain embodiments, an antibody or antigen-binding fragment thereof for use in the methods described herein specifically binds to human B7-H4 and comprises the VH framework regions of the 20502 antibody listed in Table 7.

TABLE 7

| VH FR Amino Acid Sequences [3] | | | |
|---|---|---|---|
| Anti-body | VH FR1 (SEQ ID NO:) | VH FR2 (SEQ ID NO:) | VH FR3 (SEQ ID NO:) | VH FR4 (SEQ ID NO:) |
| 20502 | QLQLQESGPGLVK PSETLSLTCTVSG (SEQ ID NO: 13) | WIRQPPGKGLE WIG (SEQ ID NO: 14) | RVTISVDTSKNQFSL KLSSVTAADTAVYY C (SEQ ID NO: 15) | WGQGTLVT VSS (SEQ ID NO: 16) |

[3] The VH framework regions described in Table 5 are determined based upon the boundaries of the Kabat numbering system for CDRs. Accordingly, the VH CDRs are determined by Kabat and the framework regions are the amino acid residues surrounding the CDRs in the variable region in the format FR1, CDR1, FR2, CDR2, FR3, CDR3, and FR4.

In certain embodiments, an antibody or antigen-binding fragment thereof for use in the methods described herein specifically binds to human B7-H4 and comprises the VL framework regions of the 20502 antibody listed in Table 8.

TABLE 8

| VL FR Amino Acid Sequences [4] | | | |
|---|---|---|---|
| Anti-body | VL FR1 (SEQ ID NO:) | VL FR2 (SEQ ID NO:) | VL FR3 (SEQ ID NO:) | VL FR4 (SEQ ID NO:) |
| 20502 | EIVMTQSPATLSVS PGERATLSC (SEQ ID NO: 17) | WYQQKPGQAP RLLIY (SEQ ID NO: 18) | GIPARFSGSGSGT EFTLTISSLQSEDF AVYYC (SEQ ID NO: 19) | FGGGTKVEI K (SEQ ID NO: 20) |

[4] The VL framework regions described in Table 6 are determined based upon the boundaries of the Kabat numbering system for CDRs. Accordingly, the VL CDRs are determined by Kabat and the framework regions are the amino acid residues surrounding the CDRs in the variable region in the format FR1, CDR1, FR2, CDR2, FR3, CDR3, and FR4.

In certain embodiments, an antibody or antigen-binding fragment thereof for use in the methods described herein specifically binds to human B7-H4 and comprises the four VH framework regions and the four VL framework regions of the 20502 antibody listed in Tables 7 and 8.

In certain embodiments, an antibody or antigen-binding fragment thereof for use in the methods described herein specifically binds to human B7-H4 and comprises the heavy chain sequence of the 20502 antibody listed in Table 9.

TABLE 9

| Full-length heavy chain amino acid sequences | |
|---|---|
| Anti-body | Full-Length Heavy Chain Amino Acid Sequence (SEQ ID NO) |
| 20502 | QLQLQESGPGLVKPSETLSLTCTVSGGSIKSGSYYWGWIRQPPGK<br>GLEWIGNIYYSGSTYYNPSLRSRVTISVDTSKNQFSLKLSSVTAA<br>DTAVYYCAREGSYPNQFDPWGQGTLVTVSSASTKGPSVFPLAPSS<br>KSTSGGTAALGCLVKDYFPEPVTVSWNSGALTSGVHTFPAVLQSS<br>GLYSLSSVVTVPSSSLGTQTYICNVNHKPSNTKVDKKVEPKSCDK<br>THTCPPCPAPELLGGPSVFLFPPKPKDTLMISRTPEVTCVVVDVS<br>HEDPEVKFNWYVDGVEVHNAKTKPREEQYNSTYRVVSVLTVLHQD<br>WLNGKEYKCKVSNKALPAPIEKTISKAKGQPREPQVYTLPPSRDE<br>LTKNQVSLTCLVKGFYPSDIAVEWESNGQPENNYKTTPPVLDSDG<br>SFFLYSKLTVDKSRWQQGNVFSCSVMHEALHNHYTQKSLSLSPGK<br>(SEQ ID NO: 21) |

In certain embodiments, an antibody or antigen-binding fragment thereof for use in the methods described herein specifically binds to human B7-H4 and comprises the light chain sequence of the 20502 antibody listed in Table 10.

TABLE 10

| Full-length light chain amino acid sequences | |
|---|---|
| Anti-body | Full-Length Light Chain Amino Acid Sequence (SEQ ID NO) |
| 20502 | EIVMTQSPATLSVSPGERATLSCRASQSVSSNLAWYQQKPGQAPR<br>LLIYGASTRATGIPARFSGSGSGTEFTLTISSLQSEDFAVYYCQQ<br>YHSFPFTFGGGTKVEIKRTVAAPSVFIFPPSDEQLKSGTASVVCL<br>LNNFYPREAKVQWKVDNALQSGNSQESVTEQDSKDSTYSLSSTLT<br>LSKADYEKHKVYACEVTHQGLSSPVTKSFNRGEC (SEQ ID NO: 22) |

In certain embodiments, an antibody or antigen-binding fragment for use in the methods described herein specifically binds to human B7-H4 and comprises the heavy chain sequence and the light chain sequence of the 20502 antibody listed in Tables 9 and 10.

In certain aspects, an antibody or antigen-binding fragment thereof for use in the methods described herein is described by its VL domain alone, or its VH domain alone, or by its 3 VL CDRs alone, or its 3 VH CDRs alone. See, for example, Rader C et al., (1998) PNAS 95: 8910-8915, which is incorporated herein by reference in its entirety, describing the humanization of the mouse anti-avβ3 antibody by identifying a complementing light chain or heavy chain, respectively, from a human light chain or heavy chain library, resulting in humanized antibody variants having affinities as high or higher than the affinity of the original antibody. See also Clackson T et al., (1991) Nature 352:624-628, which is incorporated herein by reference in its entirety, describing methods of producing antibodies that specifically bind a specific antigen by using a specific VL domain (or VH domain) and screening a library for the complementary VH domain or (VL domain). The screen produced 14 new partners for a specific VH domain and 13 new partners for a specific VL domain, which were strong binders, as determined by ELISA. See also Kim S J & Hong H J, (2007) J Microbiol 45:572-577, which is incorporated herein by reference in its entirety, describing methods of producing antibodies that specifically bind a specific antigen by using a specific VH domain and screening a library (e.g., human VL library) for complementary VL domains; the selected VL domains in turn could be used to guide selection of additional complementary (e.g., human) VH domains.

In certain aspects, the CDRs of an antibody or antigen-binding fragment thereof can be determined according to the Chothia numbering scheme, which refers to the location of immunoglobulin structural loops (see, e.g., Chothia C & Lesk A M, (1987), J Mol Biol 196:901-917; Al-Lazikani B et al., (1997) J Mol Biol 273:927-948; Chothia C et al., (1992) J Mol Biol 227:799-817; Tramontano A et al., (1990) J Mol Biol 215 (1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain aspects, provided herein are methods of administering antibodies and antigen-binding fragments thereof that specifically bind to B7-H4 (e.g., human B7-H4) and comprise the Chothia VH and VL CDRs of the 20502 antibody listed in Tables 5 and 6. In certain embodiments, provided herein are methods of administering antibodies or antigen-binding fragments thereof that specifically bind to B7-H4 (e.g., human B7-H4) and comprise one or more CDRs, in which the Chothia and Kabat CDRs have the same amino acid sequence. In certain embodiments, provided herein are methods of administering antibodies and antigen-binding fragments thereof that specifically bind to B7-H4 (e.g., human B7-H4) and comprise combinations of Kabat CDRs and Chothia CDRs.

In certain aspects, the CDRs of an antibody or antigen-binding fragment thereof can be determined according to the IMGT numbering system as described in Lefranc M-P, (1999) The Immunologist 7:132-136 and Lefranc M-P et al., (1999) Nucleic Acids Res 27:209-212. According to the IMGT numbering scheme, VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97. In a particular embodiment, provided herein are methods of administering antibodies and antigen-binding fragments thereof that specifically bind to B7-H4 (e.g., human B7-H4) and comprise the IMGT VH and VL CDRs of the 20502 antibody listed in Tables 5 and 6, for example, as described in Lefranc M-P (1999) supra and Lefranc M-P et al., (1999) supra).

In certain aspects, the CDRs of an antibody or antigen-binding fragment thereof can be determined according to MacCallum R M et al., (1996) J Mol Biol 262:732-745. See also, e.g., Martin A. "Protein Sequence and Structure Analysis of Antibody Variable Domains," in *Antibody Engineering*, Kontermann and Dübel, eds., Chapter 31, pp. 422-439, Springer-Verlag, Berlin (2001). In a particular embodiment, provided herein are methods of administering antibodies or antigen-binding fragments thereof that specifically bind to B7-H4 (e.g., human B7-H4) and comprise VH and VL CDRs of the 20502 antibody listed in Tables 5 and 6 as determined by the method in MacCallum R M et al.

In certain aspects, the CDRs of an antibody or antigen-binding fragment thereof can be determined according to the AbM numbering scheme, which refers AbM hypervariable regions which represent a compromise between the Kabat CDRs and Chothia structural loops, and are used by Oxford Molecular's AbM antibody modeling software (Oxford Molecular Group, Inc.). In a particular embodiment, provided herein are methods of administering antibodies or antigen-binding fragments thereof that specifically bind to B7-H4 (e.g., human B7-H4) and comprise VH and VL CDRs of the 20502 antibody listed in Tables 5 and 6 as determined by the AbM numbering scheme.

In specific aspects, provided herein are methods of administering antibodies that comprise a heavy chain and a light chain.

With respect to the light chain, in a specific embodiment, the light chain of an antibody described herein is a kappa light chain. The constant region of a human kappa light chain can comprise the following amino acid sequence:

```
                                    (SEQ ID NO: 23)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.
```

The constant region of a human kappa light chain can be encoded by the following nucleotide sequence:

```
                                    (SEQ ID NO: 24)
CGGACCGTGGCTGCACCATCTGTCTTCATCTTCCCGCCATCTGATGAGCAG

TTGAAATCTGGAACTGCCTCTGTTGTGTGCCTGCTGAATAACTTCTATCCC

AGAGAGGCCAAAGTACAGTGGAAGGTGGATAACGCCCTCCAATCGGGTAAC

TCCCAGGAGAGTGTCACAGAGCAGGACAGCAAGGACAGCACCTACAGCCTC

AGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTC

AACAGGGGAGAGTGT.
```

In a particular embodiment, an antibody which immunospecifically binds to a B7-H4 polypeptide (e.g., human B7-H4) for use in the methods described herein comprises a light chain wherein the amino acid sequence of the VL domain comprises the sequence set forth in Table 6, and wherein the constant region of the light chain comprises the amino acid sequence of a human kappa light chain constant region.

In a particular embodiment, an antibody which immunospecifically binds to B7-H4 (e.g., human B7-H4) for use in the methods described herein comprises a heavy chain wherein the amino acid sequence of the VH domain comprises the amino acid sequence set forth in Table 5 and wherein the constant region of the heavy chain comprises the amino acid sequence of a human gamma (γ) heavy chain constant region.

The constant region of a human IgG1 heavy chain can comprise the following amino acid sequence:

(SEQ ID NO: 25)
```
ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYKC

KVSNKALPAPIEKTISKAKGQPREPQVYTLPPSRDELTKNQVSLTCLVKGF

YPSDIAVEWESNGQPENNYKTTPPVLDSDGSFFLYSKLTVDKSRWQQGNVF

SCSVMHEALHNHYTQKSLSLSPGK.
```

The constant region of a human IgG$_1$ heavy chain can be encoded by the following nucleotide sequence:

(SEQ ID NO: 26)
```
GCCTCCACCAAGGGCCCATCGGTCTTCCCCCTGGCACCCTCCTCCAAGAGC

ACCTCTGGGGGCACAGCGGCCCTGGGCTGCCTGGTCAAGGACTACTTCCCC

GAACCGGTGACGGTGTCGTGGAACTCAGGCGCCCTGACCAGCGGCGTGCAC

ACCTTCCCGGCTGTCCTACAGTCCTCAGGACTCTACTCCCTCAGCAGCGTG

GTGACCGTGCCCTCCAGCAGCTTGGGCACCCAGACCTACATCTGCAACGTG

AATCACAAGCCCAGCAACACCAAGGTGGACAAGAAAGTTGAGCCCAAATCT

TGTGACAAAACTCACACATGCCCACCGTGCCCAGCACCTGAACTCCTGGGG

GGACCGTCAGTCTTCCTCTTCCCCCCAAAACCCAAGGACACCCTCATGATC

TCCCGGACCCCTGAGGTCACATGCGTGGTGGTGGACGTGAGCCACGAAGAC

CCTGAGGTCAAGTTCAACTGGTACGTGGACGGCGTGGAGGTGCATAATGCC

AAGACAAAGCCGCGGGAGGAGCAGTACAACAGCACGTACCGGGTGGTCAGC

GTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAA

GCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTC

TATCCCAGCGACATCGCCGTGGAGTGGGAGAGCAATGGGCAGCCGGAGAAC

AACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTTC

TCATGCTCCGTGATGCATGAGGCTCTGCACAACCACTACACGCAGAAGAGC

CTCTCCCTGTCTCCGGGTAAA.
```

In a specific embodiment, an antibody which immunospecifically binds to B7-H4 (e.g., human B7-H4) for use in the methods described herein comprises a VH domain and a VL domain comprising an amino acid sequence of any VH and VL domain described herein, and wherein the constant regions comprise the amino acid sequences of the constant regions of an IgG (e.g., a human IgG) immunoglobulin molecule. In another specific embodiment, an antibody which immunospecifically binds to B7-H4 (e.g., human B7-H4) for use in the methods described herein comprises a VH domain and a VL domain comprising an amino acid sequence of any VH and VL domain described herein, and wherein the constant regions comprise the amino acid sequences of the constant regions of an IgG$_1$ (e.g. human IgG$_1$) immunoglobulin molecule.

Antibodies with reduced fucose content have been reported to have an increased affinity for Fc receptors, such as, e.g., FcγRIIIA. Accordingly, in certain embodiments, an antibody or antigen-binding fragment thereof for use in the methods described herein has reduced fucose content or lacks fucose (i.e., is "afucosylated"). Such antibodies or antigen-binding fragments thereof can be produced using techniques known to one skilled in the art. For example, they can be expressed in cells deficient or lacking the ability to fucosylate. In a specific example, cell lines with a knockout of both alleles of the α1,6-fucosyltransferase gene (FUT8) can be used to produce antibodies or antigen-binding fragments thereof with reduced fucose content. The Potelligent® system (Lonza) is an example of such a system that can be used to produce antibodies and antigen-binding fragments thereof with reduced fucose content. Alternatively, antibodies or antigen-binding fragments thereof with reduced fucose content or no fucose content can be produced by, e.g.: (i) culturing cells under conditions which prevent or reduce fucosylation; (ii) posttranslational removal of fucose (e.g., with a fucosidase enzyme); (iii) post-translational addition of the desired carbohydrate, e.g., after recombinant expression of a non-glycosylated glycoprotein; or (iv) purification of the glycoprotein so as to select for antibodies or antigen-binding fragments thereof which are not fucsoylated. See, e.g., Longmore GD & Schachter H (1982) Carbohydr Res 100:365-92 and Imai-Nishiya H et al., (2007) BMC Biotechnol. 7:84 for methods for producing antibodies thereof with no fucose content or reduced fucose content.

In some embodiments, an afucosylated B7-H4 antibody or antigen-binding fragment thereof has enhanced ADCC activity in vitro compared to fucosylated B7-H4 antibodies or antigen-binding fragments thereof having the same amino acid sequence. In some embodiments, the afucosylated B7-H4 antibodies or antigen-binding fragments thereof cause specific lysis that is at least 10, at least 15, at least 20, at least 25, at least 30, at least 35, at least 40, at least 45, at least 50, at least 60, at least 65, at least 70, or at least 75 percentage points greater than specific lysis with fucosylated B7-H4 antibodies. Specific lysis may be determined as described in Example 2 herein.

In some embodiments, the B7-H4 antibody or antigen-binding fragment thereof has enhanced affinity for Fc gamma RIIIA compared to fucosylated B7-H4 antibodies or antigen-binding fragments thereof having the same amino acid sequence. In some embodiments, the afucosylated B7-H4 antibodies or antigen-binding fragments thereof bind to Fc gamma RIIIA with at least 2-fold, at least 3-fold, at least 4-fold, at least 5-fold, at least 7-fold, at least 10-fold, at least 12-fold, at least 15-fold, at least 17-fold, or at least 20-fold greater affinity than fucosylated B7-H4 antibodies or antigen-binding fragments thereof. In some embodiments, affinity for Fc gamma RIIIA is determined using surface plasmon resonance. In some embodiments, Fc gamma RIIIA is selected from Fc gamma RIIIA(V158) and Fc gamma RIIIA(F158). In some embodiments, Fc gamma RIIIA is Fc gamma RIIIA(V158).

In some embodiments, the presence of fucose can be determined by a method comprising high performance liquid chromatography (HPLC), capillary electrophoresis, or MALDI-TOF mass spectrometry.

In specific embodiments, an antibody or antigen-binding fragment thereof (i) comprises the CDR sequences of 20502, the VH and VL sequences of 20502, or the heavy and light chain sequences of 20502 and (ii) is afucosylated.

In specific embodiments, a composition comprises antibodies or antigen-binding fragments thereof that (i) comprises the CDR sequences of 20502, the VH and VL sequences of 20502, or the heavy and light chain sequences of 20502 and (ii) are afucosylated, e.g., wherein at least 95% of the antibodies in the composition are afucosylated or wherein fucosylation is undetectable in the composition.

Engineered glycoforms may be useful for a variety of purposes, including but not limited to enhancing or reducing effector function. Methods for generating engineered glyco-forms in an antibody or antigen-binding fragment thereof described herein include but are not limited to those dis-closed, e.g., in Umaña P et al., (1999) Nat Biotechnol 17:176-180; Davies J et al., (2001) Biotechnol Bioeng 74:288-294; Shields R L et al., (2002) J Biol Chem 277: 26733-26740; Shinkawa T et al., (2003) J Biol Chem 278:3466-3473; Niwa R et al., (2004) Clin Cancer Res 1:6248-6255; Presta L G et al., (2002) Biochem Soc Trans 30:487-490; Kanda Y et al., (2007) Glycobiology 17:104-118; U.S. Pat. Nos. 6,602,684; 6,946,292; and 7,214,775; U.S. Patent Publication Nos. US 2007/0248600; 2007/0178551; 2008/0060092; and 2006/0253928; International Publication Nos. WO 00/61739; WO 01/292246; WO 02/311140; and WO 02/30954; Potillegent™ technology (Biowa, Inc. Princeton, N.J.); and GlycoMAb® glycosy-lation engineering technology (Glycart biotechnology AG, Zurich, Switzerland). See also, e.g., Ferrara C et al., (2006) Biotechnol Bioeng 93:851-861; International Publication Nos. WO 07/039818; WO 12/130831; WO 99/054342; WO 03/011878; and WO 04/065540.

In certain embodiments, any of the constant region muta-tions or modifications described herein can be introduced into one or both heavy chain constant regions of an antibody or antigen-binding fragment thereof described herein having two heavy chain constant regions.

In another particular embodiment, an antibody or antigen-binding fragment thereof described herein, which immuno-specifically binds to B7-H4 (e.g., human B7-H4), comprises a heavy chain and a light chain, wherein (i) the heavy chain comprises a VH domain comprising the VH CDR1, VL CDR2, and VL CDR3 amino acid sequences of the 20502 antibody listed in Table 3 (SEQ ID NOs: 5, 6, and 7, respectively); (ii) the light chain comprises a VL domain comprising the VL CDR1, VH CDR2, and VH CDR3 amino acid sequences of the 20502 antibody listed in Table 4 (SEQ ID NOs: 8, 9, and 10, respectively); (iii) the heavy chain further comprises a constant heavy chain domain comprising the amino acid sequence of the constant domain of a human IgG₁ heavy chain; and (iv) the light chain further comprises a constant light chain domain comprising the amino acid sequence of the constant domain of a human kappa light chain.

In another particular embodiment, an antibody or antigen-binding fragment thereof described herein, which immuno-specifically binds to B7-H4 (e.g., human B7-H4), comprises a heavy chain and a light chain, wherein (i) the heavy chain comprises a VH domain comprising the amino acid sequence of the VH domain of the 20502 antibody listed in Table 5 (SEQ ID NO:11); (ii) the light chain comprises a VL domain comprising the amino acid sequence of the VL domain of the 20502 antibody listed in Table 6 (SEQ ID NO: 12); (iii) the heavy chain further comprises a constant heavy chain domain comprising the amino acid sequence of the constant domain of a human IgG₁ heavy chain; and (iv) the light chain further comprises a constant light chain domain comprising the amino acid sequence of the constant domain of a human kappa light chain.

In specific embodiments, an antibody or antigen-binding fragment thereof described herein, which immunospecifically binds to B7-H4 (e.g., human B7-H4) exhibits T cell checkpoint blockade activity. In specific embodiments, an antibody or antigen-binding fragment thereof described herein, which immunospecifically binds to B7-H4 (e.g., human B7-H4) increases interferon-gamma (IFNγ) produc-tion in T cells. In specific embodiments, an antibody or antigen-binding fragment thereof described herein, which immunospecifically binds to B7-H4 (e.g., human B7-H4) increases T cell proliferation. In specific embodiments, an antibody or antigen-binding fragment thereof described herein, which immunospecifically binds to B7-H4 (e.g., human B7-H4) increases CD4+ T cell proliferation. In specific embodiments, an antibody or antigen-binding frag-ment thereof described herein, which immunospecifically binds to B7-H4 (e.g., human B7-H4) increases CD8+ T cell proliferation.

In specific embodiments, an antibody or antigen-binding fragment thereof described herein, which immunospecifi-cally binds to B7-H4 (e.g., human B7-H4) exhibits anti-body-dependent cellular cytotoxicity (ADCC) activity. In specific embodiments, an antibody or antigen-binding frag-ment thereof described herein, which immunospecifically binds to B7-H4 (e.g., human B7-H4) exhibits antibody-dependent cellular cytotoxicity (ADCC) activity on cell lines with at least 300,000 cell surface B7-H4 molecules (e.g., SK-BR-3 cells). In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 100,000 cell surface B7-H4 molecules (e.g., HCC1569 cells). In specific embodiments, an antibody or antigen-binding fragment thereof described herein, which immunospecifically binds to B7-H4 (e.g., human B7-H4) exhibits antibody-dependent cellular cyto-toxicity (ADCC) activity on cell lines with at least 50,000 cell surface B7-H4 molecules (e.g., ZR-75-1 cells). In specific embodiments, an antibody or antigen-binding frag-ment thereof described herein, which immunospecifically binds to B7-H4 (e.g., human B7-H4) exhibits antibody-dependent cellular cytotoxicity (ADCC) activity on cell lines with at least 30,000 cell surface B7-H4 molecules (e.g., MDA-MB-468 cells). In specific embodiments, an antibody or antigen-binding fragment thereof described herein, which immunospecifically binds to B7-H4 (e.g., human B7-H4) exhibits antibody-dependent cellular cytotoxicity (ADCC) activity on cell lines with at least 15,000 cell surface B7-H4 molecules (e.g., HCC1964 cells).

In a specific aspect, an antigen-binding fragment as described herein, which immunospecifically binds to B7-H4 (e.g., human B7-H4), is selected from the group consisting of a Fab, Fab', F(ab')₂, and scFv, wherein the Fab, Fab', F(ab')₂, or scFv comprises a heavy chain variable region sequence and a light chain variable region sequence of an anti-B7-H4 antibody or antigen-binding fragment thereof as described herein. A Fab, Fab', F(ab')₂, or scFv can be produced by any technique known to those of skill in the art. In certain embodiments, the Fab, Fab', F(ab')₂, or scFv further comprises a moiety that extends the half-life of the antibody in vivo. The moiety is also termed a "half-life extending moiety." Any moiety known to those of skill in the art for extending the half-life of a Fab, Fab', F(ab')₂, or scFv in vivo can be used. For example, the half-life extending moiety can include a Fc region, a polymer, an albumin, or an albumin binding protein or compound. The polymer can include a natural or synthetic, optionally substituted straight or branched chain polyalkylene, polyalkenylene, polyoxyl-alkylene, polysaccharide, polyethylene glycol, polypropylene glycol, polyvinyl alcohol, methoxypolyethylene glycol, lactose, amylose, dextran, glycogen, or derivative thereof. Substituents can include one or more hydroxy, methyl, or methoxy groups. In certain embodiments, the Fab, Fab', F(ab')$_2$, or scFv can be modified by the addition of one or more C-terminal amino acids for attachment of the half-life extending moiety. In certain embodiments the half-life extending moiety is polyethylene glycol or human serum albumin. In certain embodiments, the Fab, Fab', F(ab')$_2$, or scFv is fused to an Fc region.

4.4 Pharmaceutical Compositions

Provided herein are methods of administering compositions comprising an anti-B7-H4 antibody or antigen-binding fragment thereof having the desired degree of purity in a physiologically acceptable carrier, excipient, or stabilizer (Remington's Pharmaceutical Sciences (1990) Mack Publishing Co., Easton, PA). Acceptable carriers, excipients, or stabilizers are nontoxic to recipients at the dosages and concentrations employed. (See, e.g., Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7th ed., Lippencott Williams and Wilkins (2004); Kibbe et al., Handbook of Pharmaceutical Excipients, 3rd ed., Pharmaceutical Press (2000)). The compositions to be used for in vivo administration can be sterile. This is readily accomplished by filtration through, e.g., sterile filtration membranes.

In some embodiments, methods of administering a pharmaceutical composition are provided, wherein the pharmaceutical composition comprises afucosylated anti-B7-H4 antibodies or antigen-binding fragments thereof and a pharmaceutically acceptable carrier. In specific embodiments, methods of administering a pharmaceutical composition are provided, wherein the pharmaceutical composition comprises afucosylated anti-B7-H4 antibodies or antigen-binding fragments e.g., wherein at least 80% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 85% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 90% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 95% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 96% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 97% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 98% of the antibodies in the composition are afucosylated. In specific embodiments, methods of administering a pharmaceutical composition are provided, wherein the pharmaceutical composition comprises afucosylated anti-B7-H4 antibodies or antigen-binding fragments e.g., wherein at least 99% of the antibodies in the composition are afucosylated. In specific embodiments, methods of administering a pharmaceutical composition are provided, wherein the pharmaceutical composition comprises afucosylated anti-B7-H4 antibodies or antigen-binding fragments wherein fucose is undetectable in the composition.

In some embodiments, methods of administering a pharmaceutical composition are provided, wherein the pharmaceutical composition comprises (i) an isolated antibody or antigen-binding fragment thereof that specifically binds to human B7-H4, comprising (a) the heavy chain variable region (VH) complementarity determining region (CDR) 1, VH CDR2, VH CDR3 and light chain variable region (VL) CDR1, CDR2, and CDR3 sequences of SEQ ID NOs: 5-10, respectively, (b) a variable heavy chain region comprising the amino acid sequence of SEQ ID NO: 11 and a variable light chain region comprising the amino acid sequence of SEQ ID NO:12, or (c) a heavy chain comprising the amino acid sequence of SEQ ID NO:21 and a light chain comprising the amino acid sequence of SEQ ID NO:22, and (ii) a pharmaceutically acceptable excipient.

Also provided herein is a method of administering a pharmaceutical composition, wherein the a pharmaceutical composition comprising (i) antibodies or antigen-binding fragments thereof that specifically bind to human B7-H4 and comprise the heavy chain variable region (VH) complementarity determining region (CDR) 1, VH CDR2, VH CDR3 and light chain variable region (VL) CDR1, CDR2, and CDR3 sequences of SEQ ID NOs: 5-10, respectively and (ii) a pharmaceutically acceptable excipient, wherein at least 80%, at least 85%, at least 90%, at least 95%, at least 96%, at least 97%, at least 98%, or at least 99% of the antibodies or antigen-binding fragments thereof in the composition are afucosylated. In one embodiment, (i) the antibody or antigen-binding fragment thereof comprises a variable heavy chain region comprising the amino acid sequence of SEQ ID NO:11 and a variable light chain region comprising the amino acid sequence of SEQ ID NO:12 or (ii) the antibody comprises a heavy chain comprising the amino acid sequence of SEQ ID NO:21 and a light chain comprising the amino acid sequence of SEQ ID NO: 22.

Also provided herein is a method of administering a further pharmaceutical composition, in addition to a pharmaceutical composition comprising an anti-B7-H4 antibody or antigen-binding fragment thereof. In such embodiments, the further pharmaceutical composition comprises an PD-1/PD-L1 antagonist, such as pembrolizumab. In such embodiments, the further pharmaceutical composition comprising pembrolizumab is provided as 50 mg lyophilized powder in a single dose vial for reconstitution, or as 100 mg/4 ml (25 mg/ml) solution in a single dose vial. In such embodiments, an amount of the further pharmaceutical composition is provided to deliver 200 mg pembrolizumab to the patient in a given administration. The further pharmaceutical composition may be administered concurrently or sequentially with the pharmaceutical composition comprising an anti-B7-H4 antibody or antigen-binding fragment thereof. 4.5 Antibody Production and Polynucleotides Antibodies and antigen-binding fragments thereof that immunospecifically bind to B7-H4 (e.g., human B7-H4) can be produced by any method known in the art for the synthesis of antibodies and antigen-binding fragments thereof, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Sambrook J et al., (2001) Molecular Cloning: A Laboratory Manual, Cold Spring Harbor Laboratory Press, Cold Spring Harbor, NY; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press.

In certain aspects, provided herein are methods of administering an anti-B7-H4 antibody or antigen-binding fragment thereof or a pharmaceutical composition comprising such antibodies or fragments, wherein the antibodies or fragments are produced by recombinant expression of a polynucleotide comprising a nucleotide sequence in a host cell.

In certain aspects, the anti-B7-H4 antibody or antigen-binding fragment administered according to the methods provided herein comprises a heavy chain variable region encoded by a polynucleotide comprising the nucleotide sequence shown in Table 11 (i.e. SEQ ID NO:27). In certain aspects, the anti-B7-H4 antibody or antigen-binding fragment administered according to the methods provided herein comprises a heavy chain variable region encoded by a polynucleotide comprising the nucleotide sequence shown in Table 11 (i.e. SEQ ID NO:27) and a nucleotide sequence encoding a human gamma (γ) heavy chain constant region. In certain aspects, the anti-B7-H4 antibody or antigen-binding fragment administered according to the methods provided herein comprises a heavy chain variable region encoded by a polynucleotide comprising the nucleotide sequence shown in Table 11 (i.e. SEQ ID NO:27) and a heavy chain constant domain encoded by a polynucleotide comprising the nucleotide sequence of SEQ ID NO:26.

TABLE 11

Heavy chain variable region-encoding polynucleotide sequences

| Anti-body | Heavy Chain Variable Region-Encoding Polynucleotide Sequence (SEQ ID NO) |
|---|---|
| 20502 | CAGCTGCAGCTGCAGGAGTCGGGCCCAGGACTGGTGAAGCCTTCG |
| | GAGACCCTGTCCCTCACCTGCACTGTCTCTGGTGGCTCCATCAAA |
| | AGTGGTAGTTACTACTGGGGCTGGATCCGCCAGCCCCCAGGGAAG |
| | GGGCTGGAGTGGATTGGGAACATCTATTATAGTGGGAGCACCTAC |
| | TACAACCCGTCCCTCAGAAGTCGAGTCACCATATCCGTAGACACG |
| | TCCAAGAACCAGTTCTCCCTGAAGCTGAGTTCTGTGACCGCCGCA |
| | GACACGGCGGTGTACTACTGCGCCAGAGAAGGATCTTACCCCAAT |
| | CAGTTTGATCCATGGGACAGGGTACATTGGTCACCGTCTCCTCA |
| | (SEQ ID NO: 27) |

In certain aspects, the anti-B7-H4 antibody or antigen-binding fragment administered according to the methods provided herein comprises a light chain variable region encoded by a polynucleotide comprising the nucleotide sequence shown in Table 12 (i.e., SEQ ID NO:28). In certain aspects, the anti-B7-H4 antibody or antigen-binding fragment administered according to the methods provided herein comprises a light chain variable region encoded by a polynucleotide comprising the nucleotide sequence shown in Table 12 (i.e. SEQ ID NO:28) and a nucleotide sequence encoding a human lambda light chain constant region. In certain aspects, the anti-B7-H4 antibody or antigen-binding fragment administered according to the methods provided herein comprises a light chain variable region encoded by a polynucleotide comprising the nucleotide sequence shown in Table 12 (i.e., SEQ ID NO:28) and a light chain constant domain encoded by a polynucleotide comprising the nucleotide sequence of SEQ ID NO:24.

TABLE 12

Light chain variable region-encoding polynucleotide sequences

| Anti-body | Light Chain Variable Region-Encoding Polynucleotide Sequence (SEQ ID NO) |
|---|---|
| 20502 | GAAATAGTGATGACGCAGTCTCCAGCCACCCTGTCTGTGTCTCCA |
| | GGGGAAAGAGCCACCCTCTCCTGCAGGGCCAGTCAGAGTGTTAGC |
| | AGCAACTTAGCCTGGTACCAGCAGAAACCTGGCCAGGCTCCCAGG |
| | CTCCTCATCTATGGTGCATCCACCAGGGCCACTGGTATCCCAGCC |
| | AGGTTCAGTGGCAGTGGGTCTGGGACAGAGTTCACTCTCACCATC |
| | AGCAGCCTGCAGTCTGAAGATTTTGCAGTTTATTACTGTCAGCAG |
| | TACCACTCCTTCCCTTTCACTTTTGGCGGAGGGACCAAGGTTGAG |
| | ATCAAA (SEQ ID NO: 28) |

In certain aspects, the anti-B7-H4 antibody or antigen-binding fragment administered according to the methods provided herein comprises a variable heavy chain encoded by a polynucleotide comprising the variable heavy chain-encoding nucleotide sequence shown in Table 11 (i.e. SEQ ID NO:27) and a variable light chain encoded by a polynucleotide comprising the variable light chain-encoding nucleotide sequence shown in Table 12 (i.e., SEQ ID NO:28).

In certain aspects, the anti-B7-H4 antibody or antigen-binding fragment administered according to the methods provided herein comprises (i) a heavy chain encoded by a polynucleotide comprising the variable heavy chain-encoding nucleotide sequence shown in Table 11 (i.e. SEQ ID NO:27) and a nucleotide sequence encoding a human gamma (γ) heavy chain constant region and (ii) a light chain encoded by a polynucleotide comprising the variable light chain-encoding nucleotide sequence shown in Table 12 (i.e. SEQ ID NO:28) and a nucleotide sequence encoding a human lambda light chain constant region.

In certain aspects, the anti-B7-H4 antibody or antigen-binding fragment administered according to the methods provided herein comprises (i) a heavy chain encoded by a polynucleotide comprising the variable heavy chain-encoding nucleotide sequence shown in Table 11 (i.e. SEQ ID NO: 27) and the heavy chain constant domain-encoding nucleotide sequence of SEQ ID NO:26 and (ii) a light chain encoded by a polynucleotide comprising the variable light chain-encoding nucleotide sequence shown in Table 12 (i.e., SEQ ID NO:28) and the light chain constant domain-encoding nucleotide sequence of SEQ ID NO:24.

In certain aspects, the anti-B7-H4 antibodies or antigen-binding fragments administered according to the methods provided herein are encoded by polynucleotides encoding anti-B7-H4 antibodies or antigen-binding fragments thereof or a domain thereof that are optimized, e.g., by codon/RNA optimization, replacement with heterologous signal sequences, and elimination of mRNA instability elements. Methods to generate optimized nucleic acids encoding an anti-B7-H4 antibody or antigen-binding fragment thereof or a domain thereof (e.g., heavy chain, light chain, VH domain, or VL domain) for recombinant expression by introducing codon changes (e.g., a codon change that encodes the same amino acid due to the degeneracy of the genetic code) and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly.

Polynucleotides can be, e.g., in the form of RNA or in the form of DNA. DNA includes cDNA, genomic DNA, and synthetic DNA. DNA can be double-stranded or single-stranded. If single stranded, DNA can be the coding strand or non-coding (anti-sense) strand. In certain embodiments, the polynucleotide is a cDNA or a DNA lacking one or more introns. In certain embodiments, a polynucleotide is a non-naturally occurring polynucleotide. In certain embodiments, a polynucleotide is recombinantly produced. In certain embodiments, the polynucleotides are isolated. In certain embodiments, the polynucleotides are substantially pure. In certain embodiments, a polynucleotide is purified from natural components.

In certain aspects, vectors (e.g., expression vectors) comprise nucleotide sequences encoding anti-B7-H4 antibodies and antigen-binding fragments thereof or a domain thereof for recombinant expression in host cells, preferably in mammalian cells. In certain aspects, cells, e.g. host cells, comprise such vectors for recombinantly expressing anti-B7-H4 antibodies or antigen-binding fragments thereof described herein (e.g., human or humanized antibodies or antigen-binding fragments thereof). Thus, a method for producing an antibody or antigen-binding fragment thereof described herein can comprise expressing such antibody or antigen-binding fragment thereof in a host cell.

An expression vector can be transferred to a cell (e.g., host cell) by conventional techniques and the resulting cells can then be cultured by conventional techniques to produce an antibody or antigen-binding fragment thereof described herein (e.g., an antibody or antigen-binding fragment thereof comprising the six CDRs, the VH, the VL, the VH and the VL, the heavy chain, the light chain, or the heavy and the light chain of 20502) or a domain thereof (e.g., the VH, the VL, the VH and the VL, the heavy chain, or the light chain of 20502).

In certain embodiments, anti-B7-H4 antibodies or antigen-binding fragment thereof (e.g., an antibody or antigen-binding fragment thereof comprising the CDRs of 20502) administered according to the methods provided herein are produced in Potelligent® CHOKISV cells.

In some embodiments, anti-B7-H4 antibodies or antigen-binding fragments thereof (e.g., an antibody or antigen-binding fragment thereof comprising the CDRs of 20502) administered according to the methods provided herein are produced in a host cell that lacks a functional alpha-1,6-fucosyltransferase gene (FUT8) gene. In some embodiments, the host cell is a CHO cell.

In specific embodiments, an antibody or antigen-binding fragment thereof administered according to the methods provided herein is isolated or purified. Generally, an isolated antibody or antigen-binding fragment thereof is one that is substantially free of other antibodies or antigen-binding fragments thereof with different antigenic specificities than the isolated antibody or antigen-binding fragment thereof. For example, in a particular embodiment, a preparation of an antibody or antigen-binding fragment thereof described herein is substantially free of cellular material and/or chemical precursors.

The following examples are offered by way of illustration and not by way of limitation.

5. EXAMPLES

The examples in this Section are offered by way of illustration, and not by way of limitation.

5.1 Example 1: Assessment of Prevalence of B7-H4 Expression in Multiple Indications The B7-H4 mouse monoclonal antibody A57.1 (ATCC Catalog No. PTA-5180) was used to detect the presence of B7-H4 on archival samples, a mixture of whole sections, and tumor microarrays. The samples were treated with the primary antibody and detected using a polymer detection system attached to DAB (Ventana Medical Systems).

B7-H4 was readily detected in the membrane and the cytosol in tumor tissues harvested from a variety of cancer patients, including invasive ductal carcinoma, triple negative breast cancer, ovarian cancer, non-small cell lung cancer and endometrial cancer. Moreover, frequency of expression was also high in the indications listed in Table 13.

TABLE 13

B7-H4 detection in tumors

| Tumor Type | #Total | #Positive | Percent Positive |
|---|---|---|---|
| Triple Negative Breast Cancer | 74 | 58 | 78% |
| Invasive Ductal Carcinoma | 51 | 38 | 74.50% |
| Endometrial Carcinoma | 77 | 54 | 70% |
| Ovarian Cancer | 141 | 85 | 60% |
| Non-Small Cell Lung Cancer (Squamous) | 47 | 19 | 40% |

B7-H4 is expressed in other cancers, such as breast cancer, kidney cancer (e.g., renal cell carcinoma), bladder cancer (e.g., urothelial cell carcinoma), pancreatic cancer, and thyroid cancer. See e.g., Zhu, J., et al., *Asian Pacific J. Cancer Prev.* 14:3011-3015 (2011), Krambeck A, et al., *PNAS* 103:10391-10396 (2006), Fan, M. et al., *Int. J. Clin. Exp. Pathol.* 7:6768-6775 (2014), Xu, H., et al., *Oncology Letters* 11:1841-1846 (2016), and Liu, W., et al., *Oncology Letters* 8:2527-2534 (2014).

5.2 Example 2: Afucosylated and Fucosylated 20502 Antibodies

Antibodies with Fc regions having reduced fucose content in glycan moieties may exhibit higher ADCC activity compared to a fully fucosylated antibody (Niwa R et al., *Clinical Cancer Research* 11 (6): 2327-36 (2005)). B7-H4 antibodies were generated in CHO-x cells (Yamane-Ohnuki N, et al. *Biotechnology and Bioengineering* 87 (5): 614-22 (2004)) to produce normally fucosylated antibodies and in a CHO cell line engineered to produce afucosylated antibodies (CHO-y cells) (id.).

The fucosylated and afucosylated 20502 antibodies were characterized by surface plasmon resonance (SPR). Briefly, anti-human Fab antibody was immobilized on a carboxyl-derivatized SPR chip surface, and anti-B7-H4 antibodies were captured on the resulting surface at 5 μg/ml for 30 seconds. B7-H4 IgV-huIgG1 at various concentrations (0 nM, 3.7 nM, 11.1 nM, 33.3 nM, 100 nM, and 300 nM) was then flowed over the surface and allowed to bind to the anti-B7-H4 antibodies during the association phase, followed by a buffer wash during the dissociation phase.

B7-H4 IgV-huIgG1:

(SEQ ID NO: 29)
MASLGQILFWSIISIIIILAGAIALIIGFGISGRHSITVTTVASAGNIGED

GILSCTFEPDIKLSDIVIQWLKEGVLGLVHEFKEGKDELSEQDEMFRGRTA

VFADQVIVGNASLRLKNVQLTDAGTYKCYIITSKGKGNANLEYKTGAFSGS

EPKSSDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQQ

GNVFSCSVMHEALHNHYTQKSLSLSPGK

Data was fitted using a 1:1 binding model, and the fucosylated and afucosylated 20502 showed similar binding to human B7-H4 protein. Thus there is no impact of the glycosylation on binding.

The binding affinities of the Fc regions of fucosylated 20502 (Ab-F) and afucosylated 20502 (Ab-A) to FcγRIIIa (V158) were also characterized by surface plasmon resonance (SPR). Briefly, Protein A was covalently attached to a dextran chip using the amine coupling kit with 100 mM ethylenediamine in 100 mM Sodium Borate buffer, pH 8.0 as the blocking reagent. Ab-A or Ab-F was captured at 2 densities on separate flow cells, and a Protein A derivatized flow served as a reference control. Fc gamma RIIIA(V158) was diluted in HBS-P+running buffer and injected at 6 concentrations (0 nM, 1.37 nM, 12.3 nM, 37 nM, 111 nM, 333 nM, and 1000 nM) in duplicate. The association constant, dissociation constant, and affinity for Ab-A binding were calculated using the Biacore T200 Evaluation Software 1:1 binding model. The affinity constant for Ab-A and Ab-F binding were determined using the Biacore T200 Evaluation Software steady state affinity model. The afucosylated B7-H4 antibody has a 140-fold higher affinity for Fc gamma receptor IIIA(V158) than the same antibody with a fucosylated Fc (Ab-F) (Table 14).

TABLE 14

| Fcγ receptor IIIa (FcγRIIIa) V158 allele binding | | | |
| --- | --- | --- | --- |
| | ka (1/Ms) | kd (1/s) | $K_D$ (nM) |
| Ab-A | 6.46E+05 | 9.54E-10 | 15 |
| Ab-F | N/A | N/A | 210 |

The T cell checkpoint blockade activity of fucosylated and afucosylated 20502 antibodies were also characterized. In these experiments, primary human T cells were enriched from PBMCs using the EasySep™ Human T Cell Enrichment Kit based on the manufacturer's instructions. Enriched T cells were incubated at $2\times10^5$ cell/mL with anti-CD3/anti-CD28 Dynabeads, at a one bead per cell ratio, at 37° C. Six days later, the beads were magnetically removed, and T cells were washed and incubated at $1\times10^6$ cell/mL with 10 U/mL IL-2 at 37° C. Four days later, T cells were washed and incubated at $1\times10^6$ cells/mL along with artificial antigen presenting cells (aAPCs) at a $2\times10^6$ cells/mL concentration at 37° C. in the presence of B7-H4 antibody dose titration. aAPCs were treated with Mitomycin C for one hour at 37° C. and then thoroughly washed prior to adding to the T cell co-culture. 72 hours after co-culture of T cells, aAPCs, and B7-H4 antibodies, plates were centrifuged and supernatants were harvested and assessed for IFNγ production by ELISA. IFNγ production was plotted vs. antibody concentration and the EC50 potency was calculated using nonlinear regression curve fit (GraphPad Prism).

The B7-H4 antibodies demonstrated potent T cell checkpoint blockade activity as measured by an increase in IFNγ production. Moreover, there was no demonstrable difference in potency between afucosylated and fucosylated antibodies (Table 15).

TABLE 15

| T Cell Checkpoint blockade potency | | | |
| --- | --- | --- | --- |
| | | aAPC Assay (EC50 +/- STD; nM) | |
| Antibody | BIN | Afucosylated | Fucosylated |
| 20502 | 3 | 0.89 +/- 0.44 | 0.74 +/- 0.39 |

In additional experiments, the ADCC activity of fucosylated and afucosylated 20502 antibodies was also characterized against a B7-H4-expressing target cell line. Specifically, primary human PBMCs cells were cytokine activated at $1\times10^6$ cells/mL with 200 IU/mL IL-2 at 37° C. The next day, cells were washed and incubated at a 40:1 Effector: Target ratio with SK-BR-3 target cells that were labeled with Calcein-AM. 4 hours after incubation, target cell lysis was quantified using a fluorimeter. A Triton/X treated sample served as the max lysis control sample, whereas a media alone treated sample served as the background lysis control sample. The percent (%) specific lysis was calculated as follows: [1-((sample-media control)/(max lysis-media control))]×100. The percent (%) specific lysis was plotted vs. antibody concentration and the EC50 potency was calculated using nonlinear regression curve fit (GraphPad Prism).

The B7-H4 antibodies demonstrated potent dose-dependent ADCC activity against the endogenous B7-H4 expressing breast cell line SK-BR-3. Moreover, the afucosylated antibodies demonstrated significantly more potent ADCC activity in comparison to the fucosylated antibodies (Table 16).

TABLE 16

| ADCC activity | | | |
| --- | --- | --- | --- |
| | | ADCC Assay (EC50 +/- STD; nM) | |
| Antibody | BIN | Afucosylated | Fucosylated |
| 20502 | 3 | 0.0007 +/- 1.1 × 10E-3 | 0.0370 +/- 6.2E-2 |

5.3 Example 3: Correlation of ADCC Activity with Receptor Density

B7-H4 density was quantified on the surface of SK-BR-3, HCC1569, ZR-75-1, MDA-MB-48, and HCC1964 cells by FACS according to the manufacturer's specifications. Specifically, $1\times10^5$ cells were incubated with 15 µg/mL B7-H4 antibody on ice for 25 minutes. In parallel, one drop of Quantum™ Simply Cellular (QSC) microspheres (pre-coated with increasing concentrations of anti-mouse IgG capture antibody) was also incubated with 15 µg/mL B7-H4 antibody on ice for 25 minutes. Following incubation, cells and QSC microspheres were pelleted and washed, and samples were acquired on a flow cytometer. Data was analyzed using the FlowJo software. Mean fluorescence intensity (MFI) was calculated and entered into the Quick-Cal® spreadsheet. A regression associating each bead's fluorescence channel value to its pre-assigned Antibody Binding Capacity (ABC) value will be calculated automatically. An ABC value was assigned once the MFI values for the labeled cells are also added into the template).

B7-H4 antibodies were assessed for ADCC activity against B7-H4 expressing target cell lines with different levels of B7-H4 cell surface density. Specifically, $1\times10^4$ SK-BR-3, HCC1569, ZR-75-1, MDA-MB-468, or HCC1964 target cells were co-incubated with dose-titrations of B7-H4 antibody at 4° C. 25 minutes later, a single use vial of Jurkat-huCD16 reporter cells from Promega was thawed, and $7.5\times10^4$ cells were added to the target cell/B7-H4 antibody mixture and incubated at 37° C. 24 hours later, the samples were brought to room temperature (RT) and incubated with Bio-Glo buffer. The substrate and luminescence were quantified on an En Vision multi-label reader. The data was plotted as luminescence vs. antibody concentration and the EC50 potency was calculated using nonlinear regression curve fit (GraphPad Prism).

B7-H4 antibody ADCC activity was dependent on B7-H4 cell surface density: as the numbers of cell surface molecules decreased, the amount of maximal ADCC activity also decreased. Moreover, afucosylated antibodies demonstrated improved ADCC activity in comparison to the fucosylated antibodies, especially against target cells with lower levels of B7-H4 cell surface density (FIG. 1).

5.4 Example 4: In Vivo Anti-Tumor Efficacy in Combination with Anti-PD-1 Antibody Methods: Eight week old female BALB/c mice were purchased from Charles River Laboratories (Hollister, CA) and were acclimated for up to two weeks before the start of the study. The murine breast carcinoma cell line 4T1 was engineered to express a chimeric protein containing the extracellular domain of murine B7-H4 and the transmembrane domain of murine B7H3. Tumor cells were implanted orthotopically in the mammary fat pad of the mice at $0.5\times10^5$ cells/50 ul/mouse. Prior to inoculation, the cells were cultured for no more than three passages in RPMI 1640 medium supplemented with 10% heat-inactivated Fetal Bovine Serum (FBS). Cells were grown at 37° C. in a humidified atmosphere with 5% CO2. Upon reaching 80-85% confluence, cells were harvested and resuspended in serum-free RPMI 1640 on the ventral flank of each mouse into the mammary fat pad.

Mice were monitored twice weekly following cell implantation for tumor growth. The length and width of each tumor was measured using calipers, and the volume was calculated according to the formula: Tumor volume (mm3)=(width (mm)×length (mm)2)/2. On the day of treatment initiation, all tumors were measured, outliers were excluded, and mice were randomly assigned to treatment groups. For the anti-B7-H4 treatment, a mouse surrogate of 20502 called 20502-msIgG2γ-F, which contains the 20502 variable region fused to fucosylated mouse IgG2a, was utilized. As a control, mice were administered msIgG2a (anti-HEL). 20502-msIgG2a-F or msIgG2a were administered four times via intravenous (i.v.) injection twice weekly beginning on Day 11 after inoculation. Anti-PD-1 (a modified version of RMP1-14 (Bio X Cell) containing a Fc silent msIgG2a domain) was administered three times via intraperitoneal (i.p.) injection twice weekly beginning on Day 11 after inoculation. Tumors continued to be measured at least twice per week until tumor volume exceeded 10% of animal weight, or approximately 2000 mm3.

Results: The change in tumor size, the change in mean tumor volume, and the percent survival are shown in FIGS. 1A, 1B and 1C, respectively. Treatment with either 20502-msIgG2a-F or anti-PD-1 significantly reduced tumor growth compared to msIgG2a control (p<0.05). The co-administration of 20502-msIgG2a-F and anti-PD-1 significantly enhanced tumor growth inhibition compared to either monotherapy (p<0.05). Moreover, combination therapy resulted in complete tumor regression in 5 of 12 mice. P-values were calculated using One-Way ANOVA analyses of the calculated tumor volumes on each day of the study with multiple comparisons between each group.

Figure 2:
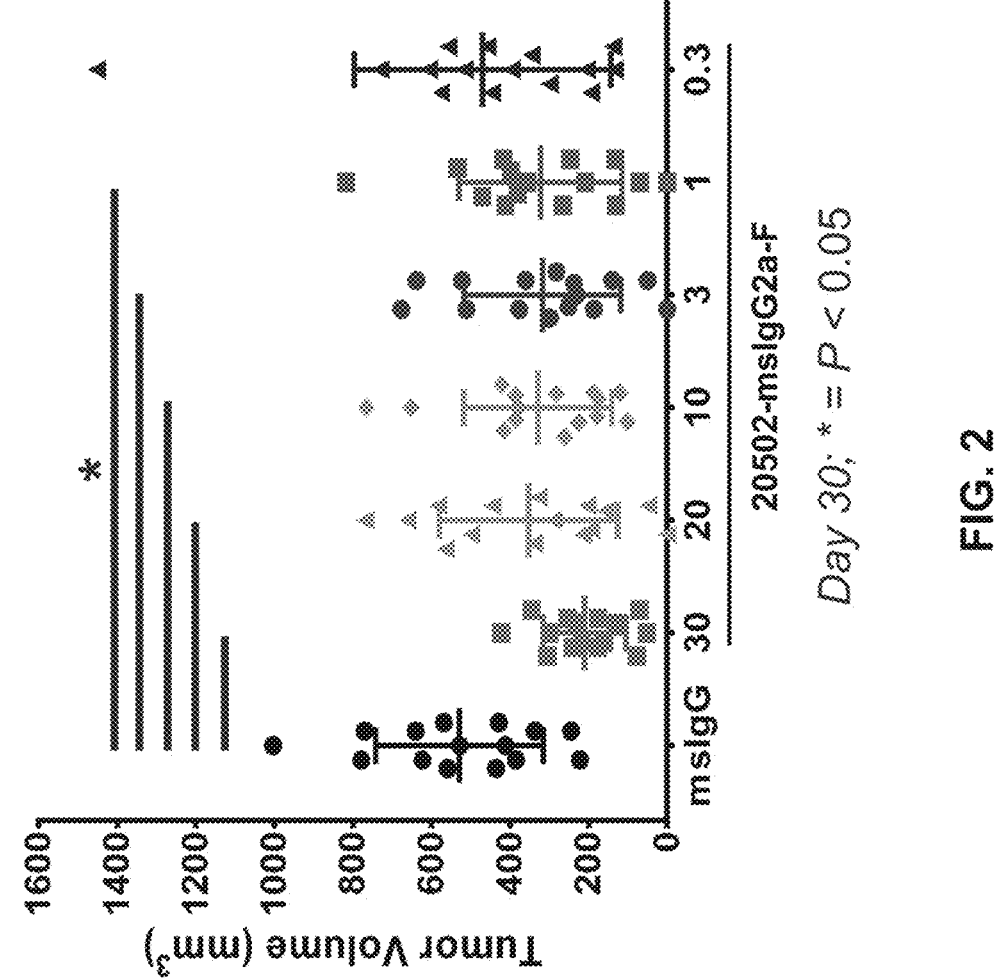
FIG. 2 shows the dose-dependent anti-tumor activity of an anti-B7-H4 antibody. (See Example 4.)
Figure 3:
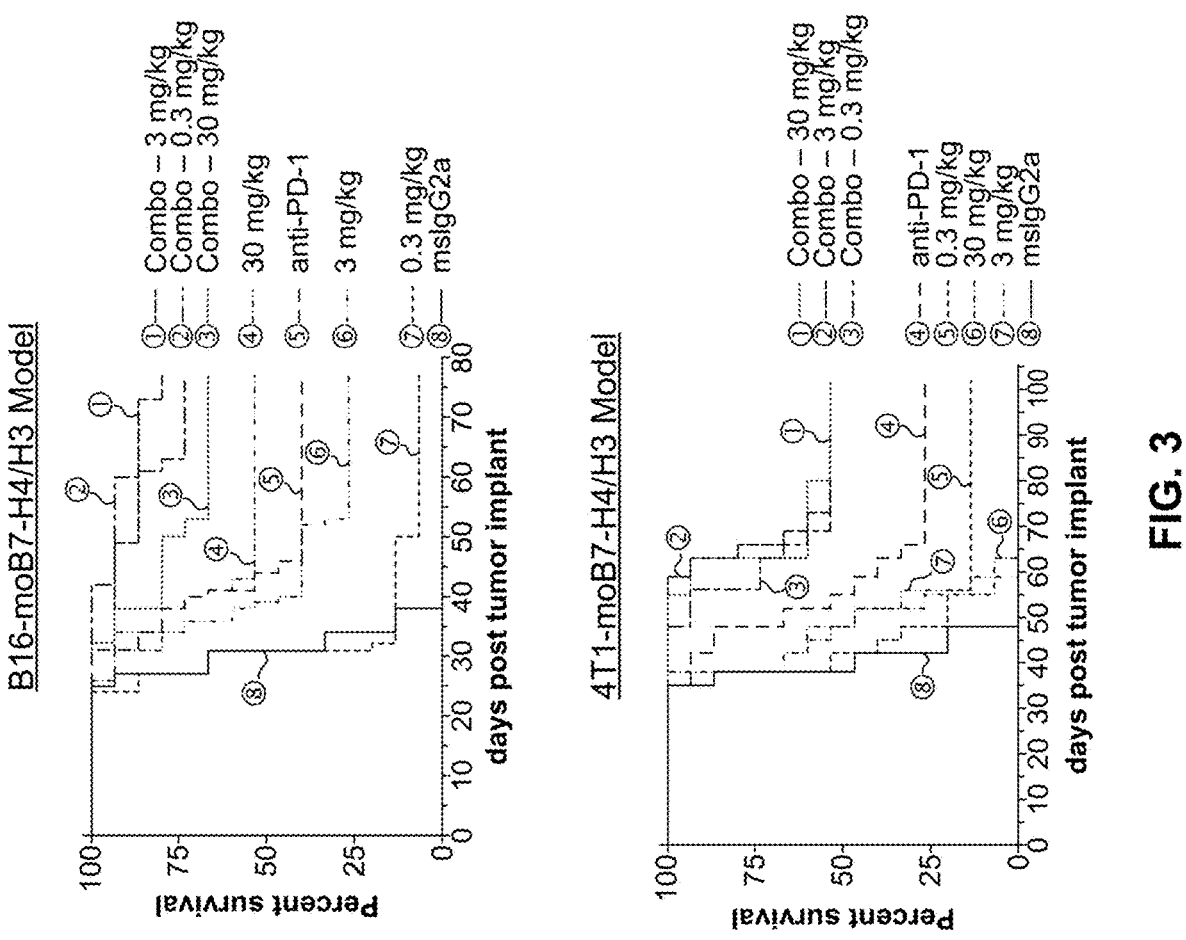
FIG. 3 shows that an anti-B7-H4 antibody combines synergistically with an anti-PD1 antibody, even when the anti-B7-H4 antibody is administered at a dose that is not effective as a monotherapy. (Sec Example 4.)

In additional experiments, 20502-msIgG2a-F demonstrated dose-dependent anti-tumor activity as a monotherapy in the engineered 4T1 model at doses as low as 1 and 3 mg/kg (FIG. 2). Combining 20502-msIgG2a-F at doses of 0.3 mg/kg, 3 mg/kg or 30 mg/kg with the anti-PD-1 antibody (5 mg/kg) resulted in synergistic anti-tumor activity in both the engineered 4T1 model and a similarly engineered B16 (melanoma) model at nearly all doses of 20502-msIgG2a-F tested (FIG. 3). (The PD-1 antibody was administered to the 4T1 model three times on the same days as the first three doses of 20502-msIgG2a-F and to the B16 model twice on the same days as the second and fourth doses of 20502-msIgG2a-F.) This synergistic effect was particularly unexpected for the 0.3 mg/kg dose, given that administration of 20502-msIgG2a-F alone at that dose did not have a significant effect on tumor volume (FIG. 2). Moreover, the efficacy (percent survival) observed at the 0.3 mg/kg dose of 20502-msIgG2a-F in combination with anti-PD1 was surprisingly comparable, or even superior, to the efficacy observed at either the 3 mg/kg or 30 mg/kg dose in combination with anti-PD1. Thus, these results show that anti-PD1 combines synergistically with an anti-B7-H4 antibody at doses of the latter that are non-efficacious as a monotherapy, and this may have advantages not only in terms of efficacy, but also safety.

5.5 Example 5: Nonclinical Pharmacokinetics

The pharmacokinetics (PK) and toxicokinetics (TK) of afucosylated 20502 were evaluated following a single and/or repeat weekly intravenous (IV) administration in mice, rats, and cynomolgus monkeys. PK characteristics observed were consistent across all studies. In all species, afucosylated 20502 demonstrated linear PK and a dose proportional increase in exposure (area under serum concentration-time curve [AUC]) with increasing dose. There was an approximate 2-fold increase in weekly exposure ($AUC_{0-7}$ days) following 4 weekly administrations of 20502 between first and last dose; however, steady state was not achieved. No substantial gender differences were apparent in the serum afucosylated 20502 concentration-time profiles. In the cynomolgus monkey (across 2 different studies), half-life estimated from recovery animals ranged from approximately 8.8 days to 12 days, with doses levels ranging from 1 to 100 mg/kg. The estimated half-life in rat following a single IV infusion administration at 40 mg/kg was approximately 13.2 days. The PK characteristics of afucosylated 20502 in animals support IV infusion in humans with a once every 3 week (Q3W) dose regimen.

5.6 Example 6: Toxicology

Toxicology studies with afucosylated 20502 were performed in rat and cynomolgus monkey. The studies included a pilot single dose pharmacokinetic (PK)/tolerability study in rats, a pilot repeat-dose toxicity study in cynomolgus monkeys, and investigational new drug (IND)-enabling Good Laboratory Practices (GLP) repeat-dose toxicity studies in rats and cynomolgus monkeys, as well as a GLP tissue cross-reactivity study with human, rat, and cynomolgus monkey tissues.

In the single dose pilot tolerability study in rats, the animals received doses up to 40 mg/kg as a 30-minute intravenous (IV) infusion. Afucosylated 20502 had no effect on clinical observations, body weights, food consumption, clinical pathology (serum chemistry or hematology) assessments, gross observations, organ weights, or histopathology assessment.

In the pilot repeat-dose toxicology study cynomolgus monkeys received 4 weekly IV doses of afucosylated 20502 up to 100 mg/kg as a 30-minute IV infusion. All doses were well tolerated by cynomolgus monkeys. There were no test article-related unscheduled mortalities or changes attributed to administration of afucosylated 20502 during assessment of clinical observations, body weights, clinical pathology, necropsy, organ weight, or histopathology parameters.

In the repeat-dose GLP toxicology studies, afucosylated 20502 was administered by IV at dose levels of 1, 10, and 100 mg/kg/dose to both rats and cynomolgus monkeys for 4 weekly doses. Reversibility of toxicity was evaluated during a 6-week recovery period following the final administration. Parameters for evaluation included ophthalmic examinations, clinical observations, body temperatures, body weights, food consumption, hematology, coagulation, clinical chemistry, urinalysis, organ weights, macroscopic, and microscopic evaluation. In the cynomolgus monkey study, electrocardiograms (ECGs) were also assessed to evaluate potential cardiac toxicities.

During the evaluation of the GLP rat study, afucosylated 20502 was generally well tolerated, and there were no toxic effects attributed to afucosylated 20502. The no-observed-adverse-effect level (NOAEL) in Sprague Dawley rats was considered to be 100 mg/kg/dose.

In the GLP cynomolgus monkey study, afucosylated 20502 was generally well tolerated, and there were no adverse events (AEs) attributed to afucosylated 20502 observed in any of the parameters evaluated. During the study, a higher incidence of diarrhea was observed at the end of the dosing phase in the higher dose groups. Due to the higher incidence of affected animals in the mid and high dose, as well as onset in the later phase of the dosing period, a relationship with afucosylated 20502 exposure is possible. There were no microscopic changes in the intestinal tract in animals treated with afucosylated 20502, including animals with diarrhea; therefore, this finding was considered non-adverse but possibly related to the test article. There was a single mortality in the study. One animal in the mid-dose recovery group was found dead on Study Day 35, 14 days post the last dose. Clinical observations, macroscopic and microscopic evaluation were consistent with the diagnosis of intestinal torsion. Intestinal torsions occasionally occur in cynomolgus monkeys, and this was considered a spontaneous condition in this animal and not test article-related. The NOAEL in cynomolgus monkey was considered to be 100 mg/kg/dose.

In addition to in vivo toxicology studies, a GLP-compliant tissue cross reactivity study was performed to compare the binding of afucosylated 20502 to a panel of 36 tissues from rat, cynomolgus monkey, and human. The results showed that the binding pattern of afucosylated 20502 was similar among the 3 species and limited to the mammary gland epithelium.

Thus, afucosylated 20502 was well tolerated in cynomolgus monkey and rat. The NOAEL in both species was considered to be 100 mg/kg/dose, the highest dose tested when given as 4 weekly IV doses.

5.7 Example 7: Phase 1a Dose Escalation/Safety Lead-In and Phase 1b Dose Expansion Studying Afucosylated 20502 in Combination with Pembrolizumab For convenience, Afucosylated 20502 is referred to as A-20502 in this Example.

Title: A Phase 1a/1b Study of an Anti-B7-H4 Antibody in Combination with Pembrolizumab (an Anti-PD1 Antibody) in Patients with Advanced Solid Tumors

TABLE 17

| OBJECTIVES | ENDPOINTS |
| --- | --- |
| | PRIMARY |
| | Safety |
| A-20502 Combined with Pembrolizumab | A-20502 Combined with Pembrolizumab |
| To evaluate the safety and tolerability of A-20502 in combination with pembrolizumab in patients with advanced solid tumors | The incidence of AEs, clinical laboratory abnormalities, and ECG abnormalities |
| To determine the maximum tolerated dose (MTD) and/or recommended dose (RD) of A-20502 in combination with pembrolizumab in patients with advanced solid tumors | The incidence of Grade 3 and Grade 4 AEs and clinical laboratory abnormalities defined as DLTs |

TABLE 17-continued

| OBJECTIVES | ENDPOINTS |
|---|---|
| SECONDARY<br>Pharmacokinetics | |
| A-20502 Combined with Pembrolizumab<br>To characterize the PK profile of A-20502 in combination with pembrolizumab in patients with advanced solid tumors | A-20502 Combined with Pembrolizumab<br>The following PK parameters will be derived from concentration-time data for A-20502 in combination with pembrolizumab when appropriate and applicable:<br>AUC (Area under serum concentration time curve)<br>$C_{max}$ (Maximum serum concentration)<br>$C_{trough}$ (trough serum concentration at the end of a dose interval)<br>CL (Clearance)<br>$t_{1/2}$ (Terminal half-life)<br>$V_{ss}$ (Volume of distribution at steady state)<br>Other parameters, such as dose proportionality, accumulation ratio, attainment of steady state, will also be calculated if the data are available for A-20502<br>Accumulation ratio of $C_{max}$ and $C_{trough}$ for pembrolizumab may be calculated if the data are available. |
| Immunogenicity | |
| A-20502 Combined with Pembrolizumab<br>To characterize the immunogenicity of A-20502 in combination with pembrolizumab in patients with advanced solid tumors | A-20502 Combined with Pembrolizumab<br>Immune response (ADAs) to A-20502<br>Immune response (ADAs) to pembrolizumab |
| EXPLORATORY<br>Efficacy | |
| A-20502 Combined with Pembrolizumab<br>To evaluate the clinical benefit of A-20502 in combination with pembrolizumab | A-20502 Combined with Pembrolizumab<br>Objective response rate (ORR), defined as the total number of patients with confirmed responses of either CR or PR per RECIST v1.1 divided by the total number of patients who are evaluable for a response<br>Duration of response (DOR), defined as the time from onset of response (CR or PR) that is subsequently confirmed to the first observation of progressive disease or death due to any cause<br>Progression free-survival (PFS), defined as the time from the patient's first dose to the first observation of progressive disease or death due to any cause |
| Pharmacodynamic Biomarkers | |
| A-20502 Combined with Pembrolizumab<br>To characterize the pharmacodynamic profile of A-20502 in combination with pembrolizumab through an analysis of the immune cell infiltrate in pre-treatment and on-treatment tumor biopsies<br>To characterize the pharmacodynamic profile of A-20502 in combination with pembrolizumab through evaluation of exploratory biomarkers in peripheral blood samples | A-20502 Combined with Pembrolizumab<br>Changes in markers of tumor immune infiltrate (eg, may include natural killer cells (NK), CD4, CD8, and/or other select immune biomarkers) by IHC and/or RNA analysis in patients treated with A-20502 in combination with pembrolizumab<br>Changes in cytokine levels (e.g., may include IL-2, IL-6, IL-10, TNF, IFNγ) as determined by multiplex analysis in patients treated with A-20502 in combination with pembrolizumab<br>Changes in selected additional pharmacodynamic markers in peripheral blood in patients treated with A-20502 in combination with pembrolizumab |

TABLE 18

| OBJECTIVES | ENDPOINTS |
|---|---|
| PRIMARY<br>Safety | |
| A-20502 Combined with Pembrolizumab<br>To evaluate the safety and tolerability of A-20502 in combination with pembrolizumab in selected patients with B7-H4 + advanced solid tumors treated at the MTD and/or RD | A-20502 Combined with Pembrolizumab<br>The incidence of AEs, clinical laboratory abnormalities, and ECG abnormalities in patients treated with A-20502 in combination with pembrolizumab |
| SECONDARY<br>Efficacy | |
| A-20502 Combined with Pembrolizumab<br>To evaluate the clinical benefit of A-20502 in | A-20502 Combined with Pembrolizumab<br>ORR, defined as the total number of patients with |

TABLE 18-continued

| OBJECTIVES | ENDPOINTS |
|---|---|
| combination with pembrolizumab in selected patients with B7-H4 + advanced solid tumors treated at the MTD and/or RD | confirmed responses of either CR or PR per RECIST v1.1 divided by the total number of patients who are evaluable for a response to A-20502 combined with pembrolizumab<br>DOR, defined as the time from onset of response (CR or PR) that is subsequently confirmed to the first observation of progressive disease or death due to any cause to A-20502 combined with pembrolizumab<br>PFS, defined as the time from the patient's first dose to the first observation of progressive disease or death due to any cause to A-20502 combined with pembrolizumab |

Pharmacokinetics

| OBJECTIVES | ENDPOINTS |
|---|---|
| A-20502 Combined with Pembrolizumab<br>To characterize the PK profile of A-20502 in combination with pembrolizumab in patients with B7-H4 + advanced solid tumors treated at the MTD and/or RD<br>To characterize the PK profile of perbrolizimab in combination with A-20502 in patients with advanced solid tumors | A-20502 Combined with Pembrolizumab<br>The following PK parameters will be derived from concentration-time data for A-20502 in combination with pembrolizumab when appropriate and applicable:<br>AUC<br>$C_{max}$<br>$C_{trough}$<br>CL<br>$t_{1/2}$<br>$V_{ss}$<br>Other parameters, such as accumulation ratio, attainment of steady state, will also be calculated if the data are available for patients treated with A-20502 combined with pembrolizumab<br>$C_{max}$ and $C_{trough}$ as well as the accumulation ratio of $C_{max}$ and $C_{trough}$ for pembrolizumab may be calculated if the data are available. |

Immunogenicity

| OBJECTIVES | ENDPOINTS |
|---|---|
| A-20502 Combined with Pembrolizumab<br>To characterize the immunogenicity of A-20502 in combination with pembrolizumab in selected patients with B7-H4 + advanced solid tumors treated at the MTD and/or RD<br>To characterize the immunogenicity of pembrolizumab in combination with A-20502 patients with with B7-H4 + advanced solid tumors treated at the MTD and/or RD | A-20502 Combined with Pembrolizumab<br>Immune response (ADAs) to A-20502<br>Immune response (ADAs) to pembrolizumab |

EXPLORATORY
Pharmacodynamic Biomarkers

| OBJECTIVES | ENDPOINTS |
|---|---|
| A-20502 Combined with Pembrolizumab<br>To characterize the pharmacodynamic profile of A-20502 in combination with pembrolizumab through an analysis of the immune cell infiltrate in pre-treatment and on-treatment tumor biopsies<br>To characterize the pharmacodynamic profile of FP150 in combination with pembroliumab through evaluation of exploratory biomarkers in peripheral blood samples | A-20502 Combined with Pembrolizumab<br>Changes in markers of tumor immune infiltrate, (eg, may include natural killer cells (NK), CD4, CD8, and/or other select immune biomarkers) by IHC and/or RNA analysis for patients treated with A-20502 in combination with pembrolizumab<br>Changes in cytokine levels (e.g., may include IL-2, IL-6, IL-10, TNF, IFNγ) as determined by multiplex analysis for patients treated with A-20502 in combination with pembrolizumab<br>Changes in selected additional pharmacodynamic biomarkers in peripheral blood samples for patients treated with A-20502 in combination with pembrolizumab |

Efficacy

| OBJECTIVES | ENDPOINTS |
|---|---|
| A-20502 Combined with Pembrolizumab<br>To evaluate the clinical benefit of A-20502 in combination with pembrolizumab in selected patients with B7-H4 + advanced solid tumors treated at the MTD and/or RD | A-20502 Combined with Pembrolizumab<br>Overall Survival (OS), defined as time from patient's first dose to death due to any cause for patients treated with A-20502 in combination with pembrolizumab |

In certain embodiments, pembrolizumab for injection is supplied as a sterile, preservative-free, white to off-white lyophilized powder in single-dose vials. Each vial may be reconstituted and diluted for intravenous infusion. Each 2 mL of such reconstituted solution contains 50 mg of pembrolizumab and is formulated in L-histidine (3.1 mg), polysorbate 80 (0.4 mg), and sucrose (140 mg). May contain hydrochloric acid/sodium hydroxide to adjust pH to 5.5. The lyophilized powder is reconstituted by adding 2.3 mL of Sterile Water for Injection, USP by injecting the water along the walls of the vial and not directly on the lyophilized powder (resulting concentration 25 mg/mL). The vial is slowly swirled (without shaking) and allowed up to 5 minutes for the bubbles to clear.

In other embodiments, pembrolizumab is available for injection as a 100 mg/4 mL (25 mg/mL) solution in a single use vial. The injection is a sterile, preservative-free, clear to slightly opalescent, colorless to slightly yellow solution that requires dilution for intravenous infusion. Each vial contains 100 mg of pembrolizumab in 4 mL of solution. Each 1 mL of solution contains 25 mg of pembrolizumab and is formulated in: L-histidine (1.55 mg), polysorbate 80 (0.2 mg), sucrose (70 mg) and Water for Injection, USP.

Study Design: This is a Phase 1a/1b open-label, multi-center, study to evaluate the dosing, safety, tolerability, pharmacokinetics (PK), pharmacodynamics, and preliminary efficacy of A-20502 in combination with pembrolizumab in advanced solid tumors.

This study includes a Phase 1a dose escalation/safety-lead in portion (Phase 1a Dose Escalation) and a Phase 1b dose expansion portion (Phase 1b Dose Expansion) for A-20502 in combination with pembrolizumab.

Archival tumor tissue (or fresh biopsy obtained if archival tissue is not available) may be pre-screened to test for B7-H4 (transmembrane protein of the B7 family also known as B7S1, B7x, or VTCN1) expression levels by immunohisto-chemistry (IHC) at a central laboratory for patients in Phase 1a Dose Exploration and Phase 1b Dose Expansion and for biomarker analysis.

In certain embodiments, Archival Tumor Tissue and/or Fresh Biopsies are provided as follows:

Phase 1a Dose Escalation:
Provision of archival tumor tissue (or fresh biopsy obtained if archival tissue is not available) for retrospective biomarker analysis for patients.

Phase 1a Dose Exploration:
Archival tumor tissue to evaluate for B7-H4 expression levels through IHC testing performed at a central laboratory for pre-screening and for biomarker analysis; fresh biopsy tissue will be used for this test if archival tissue is not available.
Fresh biopsies will be used during screening and post-treatment.

Phase 1b Dose Expansion:
Archival tumor tissue to evaluate for B7-H4 expression level through IHC testing performed at a central laboratory for pre-screening and for biomarker analysis; fresh biopsy tissue is used for this test if archival tissue is not available.
Fresh biopsies will be used for a subset of patients (e.g., at least 10 patients per 30-patient cohort) during screening and post-treatment, for expanded pharmacodynamic analysis.

Additional details are provided below for each study phase under Phase 1a Dose Escalation and Phase 1b Dose Expansion sections of this Synopsis.

Phase 1a Safety Lead-in (A-20502 in combination with pembrolizumab): At least 3 patients will be enrolled at the maximum tolerated dose (MTD) and/or recommended dose (RD) of A-20502 as monotherapy combined with 200 mg pembrolizumab Q3W and evaluated for dose limiting toxicities (DLTs). Additional patients for a total of up to 10 patients may be treated at the RD of A-20520 and pembrolizumab. If required, the dose of A-20502 may be reduced in accordance with the algorithm for de-escalation described below. The proposed dose levels are:
1aC1: A-20502 (RD)+pembrolizumab 200 mg IV Q3W
1aC2: A-20502 (10 mg/kg)+pembrolizumab 200 mg IV Q3W
1aC3: A-20502 (3 mg/kg)+pembrolizumab 200 mg IV Q3W Abbreviations: IV=intravenous; Q3W=once every 3 weeks; RD=recommended dose.

In some embodiments, the RD is 20 mg/kg. In a phase 1a/1b monotherapy study in patients with advanced solid tumors, A-20502 was well tolerated at doses as high as 20 mg/kg with no dose limiting toxicities. Based on pharmacokinetic studies of the patients in that phase 1a/1b monotherapy study, the observed trough concentration of A-20502 at the RD of 20 mg/kg is projected to achieve ≥95% receptor saturation for both B7-H4 and FcγIIIa based on affinities. A-20502 achieved dose-proportional exposures at doses ≥0.3 mg/kg and had a half-life of 1-2 weeks. The serum concentration of A-20502 at 20 mg/kg was similar over time across tumor types (breast, ovarian, and endometrial) and with or without pembrolizumab.

Other dose levels may be used (e.g., 0.1, 0.3, 1, or 20 mg/kg) in the combination study, e.g., based on safety, tolerability, objective response, PK, and pharmacodynamics and estimates of efficacious exposures extrapolated from nonclinical data. For example, lower or intermediate dose levels of A-20502 based on safety data may be used. The DLT criteria for the combination of A-20502 and pembrolizumab will be as follows:

DLTs during Phase 1a Dose Escalation are defined as any of the following events regardless of attribution (except for those events clearly due to the underlying disease or extraneous causes):
Any Grade 3 or higher non-hematologic toxicity (except Grade 3 nausea, vomiting and diarrhea) occurring within the 21 days of treatment
Grade 3 nausea, vomiting, diarrhea lasting >72 hours, despite optimal supportive care, occurring within first 21 days of treatment
Febrile neutropenia and/or documented infection with absolute neutrophil count (ANC)<$1.0\times10^9$ per L, Grade 4 neutropenia lasting for more than 7 days, Grade 4 thrombocytopenia (<$25.0\times10^9$ per L), or Grade 3 thrombocytopenia (<$50.0$-$25.0\times10^9$ per L) accompanied by bleeding within first 21 days of treatment
Aspartate aminotransferase/alanine transaminase (AST/ALT)>3× upper limit of normal (ULN) and concurrent total bilirubin >2× ULN not related to liver involvement with cancer
Any Grade 4 laboratory value regardless of clinical sequelae
Other Grade 3 laboratory values that are not of clinical significance according to Investigator and Sponsor agreement that do not resolve within 72 hours Specific DLT Considerations for the Combination of A-20502 and Pembrolizumab
Because pembrolizumab is a known immune checkpoint inhibitor and one of the proposed mechanisms of action of A-20502 is immune checkpoint blockade, immune-related adverse events (irAEs) are anticipated with this combination. An irAE is defined as a clinically significant AE that is associated with study drug exposure, of unknown etiology, and is consistent with an immune-mediated mechanism. Based on that background, the first occurrence of the following irAEs will not be considered a DLT because they are expected with immune therapy:
Grade 3 tumor flare (defined as local pain, irritation, or rash localized at sites of known or suspected tumor),
Grade 3 rash
Grade 3 immune-related adverse event (irAE) that resolved to a Grade 1 or less within 14 days.

Transient (resolving within 6 hours of onset) Grade 3 infusion-related AE

A second occurrence of these events (except Grade 3 tumor flare) either in the same or different patient will be considered a DLT.

The DLT evaluation interval begins on the first day of treatment upon start of infusion and continues for 21 days. The algorithm outlined in the table below will apply for dosing decisions. The dose of A-20502 may be lowered as needed in response to DLTs. The MTD and/or RD of A-20502 in combination with pembrolizumab will be a dose where ≤1/3-6 patients encounter a DLT.

TABLE 19

Algorithm for Dose De-Escalation Decisions for A-20502 Safety Lead-in in Combination with Pembrolizumab in phase 1a:

| Number of Patients with DLT at a Given Dose Level | Dosing Decision Rule |
|---|---|
| 0/3 | Proceed with enrollment of up to 10 total patients at that dose level for additional safety assessment |
| 1/3 | Enroll 3 additional patients at current dose level (current cohort) |
| ≥2/3 | Stop enrollment at current cohort and de-escalate A-20502 to one dose level below current dose |
| 1/6 | Proceed with enrollment of up to 10 total patients at that dose level |
| ≥2/6 | Stop enrollment at current cohort and de-escalate A-20502 to one dose level below current dose. |

Phase 1b Combination Expansion:

Phase 1b may consist of cohorts of prospectively identified as having B7-H4 expression by IHC. In certain embodiments, there will be two cohorts of A-20502 in combination with pembrolizumab in the following selected tumor types:

Cohort 1bC1: TNBC (A-20502 in combination with pembrolizumab)

Cohort 1bC2: Ovarian cancer (A-20502 in combination with pembrolizumab)

In another embodiment, the Phase 1b Combination has one initial cohort, and other cohorts such as TNBC may be enrolled subsequently in the Phase 1b trial:

Cohort 1bC1: Ovarian Cancer (A-20502 in combination with pembrolizumab)

In certain embodiments, up to 3 additional combination cohorts may be added.

Based on emerging available clinical and translational data from the study, cohorts for additional tumor types to be treated with A-20502 in combination with pembrolizumab may be opened during the trial (e.g., 30 patients or less in any individual cohort).

Dosing: In certain embodiments, A-20502 will be administered as a single agent in a 60-minute (±5 minutes) IV infusion Q3W, on Day 1 of each 21-day cycle. The dose of A-20502 will be based on body weight at Cycle 1 Day 1 (C1D1). After Cycle 1, the A-20502 dose will be recalculated at each infusion visit only if the patient's weight has changed >10% from Cycle 1, Day 1.

Pembrolizumab will be administered after completion of A-20502 IV infusion at a dose of 200 mg by IV infusion over 30 minutes (±5 minutes) starting on Cycle 1, Day 1 and repeated Q3W on Day 1 of each 21-day cycle.

There is no pre-specified maximum number of doses of A-20502 in combination with pembrolizumab. Patients may continue receiving both drugs in combination according to their study specified cohort/dose until investigator assessed disease progression or the patient meets any of the other protocol-specified withdrawal criteria. If a patient discontinues one of the two drugs, the patient may continue to receive the other drug alone.

Treatment beyond disease progression may be allowed in patients with progressive disease according to Response Evaluation Criteria in Solid Tumors version 1.1 (RECIST v1.1) if the benefit/risk assessment favors continued administration of study treatment (e.g., if patients are continuing to experience clinical benefit as assessed by the Investigator and tolerating treatment).

Study Duration: The duration of study for an individual patient includes screening (up to 28 days), treatment, and an End of Treatment (EOT) follow-up period which will include visits at approximately 28 (±7) days and 100 (±7) days after the last dose. Since all patients are eligible to be treated until disease progression, the actual treatment duration for each individual patient will vary depending on the anticipated time to progression for their respective tumor type.

In addition, patients enrolled in Phase 1b Dose Expansion will be followed for survival (LTFU including scans and survival status Q12W) for up to 2 years.

Number of Patients: The number of patients planned for this study is estimated as follows but this number may be adjusted as appropriate.

Phase 1a may enroll from 6 to 22 patients or 10 to 22 patients who will receive A-20502 in combination with pembrolizumab in the safety lead-in. The one or two additional cohorts evaluating A-20502 in combination with pembrolizumab will be enrolled, e.g., with 30 patients or less.

Eligibility Criteria:

Inclusion Criteria: Phase 1a Inclusion Criteria

Inclusion criteria for patients enrolling into Phase 1a are as follows:

1) Histologically confirmed solid tumors except primary central nervous system (CNS) tumors.

2) Disease that is unresectable, locally advanced, or metastatic.

3) Able to understand and sign an Institutional Review Board/Independent Ethics Committee (IRB/IEC)-approved Informed Consent Form (ICF) prior to any study-specific evaluation. 4) Patients should be refractory to or intolerant of existing therapy(ies) known to provide clinical benefit for their condition.

5) All patients must have at least one measurable lesion at baseline according to RECIST v1.1; tumor sites situated in a previously irradiated area, or in an area subjected to other loco-regional therapy, are not considered measurable unless there has been demonstrated progression in the lesion.

6) Adequate washout for prior anti-cancer therapy (ie, >5 half-lives or 4 weeks since the last dose, whichever is shorter).

7) Availability of archival tumor tissue and consent to providing archival tumor for retrospective biomarker analysis, or patient must undergo a fresh tumor biopsy during screening if archival tissue is not available (a biopsy is required for patients in the Phase 1a Dose Exploration portion).

8) Age >18 years at the time the ICF is signed.

9) Eastern Cooperative Oncology Group (ECOG) performance status of 0 or 1.

10) Life expectancy of at least 3 months in the opinion of the Investigator.

11) Willing and able to comply with all study procedures.

12) Prior radiotherapy must be completed at least 2 weeks before the first dose of study drug.

13) Prior radiopharmaceuticals (e.g., strontium, samarium) must be completed at least 8 weeks before the first dose of study drug.

14) Prior surgery that requires general anesthesia must be completed at least 1 week before first dose of study drug administration. Surgery requiring local/epidural anesthesia must be completed at least 72 hours before first dose of study drug administration. Patients must have recovered from any surgery.

15) Screening laboratory values must meet the following criteria:

Hematologic a. Neutrophils ≥1200 cells/μL b. Platelets ≥75×10³/μL c. Hemoglobin (Hb) ≥9.0 g/dL Renal:

Serum creatinine <1.5× ULN or creatinine clearance (CrCl) of ≥40 mL/minute (using Cockcroft/Gault Formula)

$$\text{Female } CrCl \; \frac{(140 - \text{age in years}) \times (\text{weight in kg}) \times 0.85}{72 \times (\text{serum creatinine in mg/dL})}$$

$$\text{Male } CrCl \; \frac{(140 - \text{age in years}) \times (\text{weight in kg})}{72 \times (\text{serum creatinine in mg/dL})}$$

Hepatic:

d. AST and ALT≤3× ULN (AST and ALT <5× ULN in patients with liver metastases is permitted)

e. Bilirubin <1.5× ULN (except patients with Gilbert's syndrome, who must have total bilirubin <3 mg/dL)

16) Negative serum β-human chorionic gonadotropin (β-hCG) pregnancy test ≤96 hours prior to treatment on Cycle 1, Day 1 (women of childbearing potential only).

17) In sexually active patients (women of child bearing potential and males), willingness to use 2 effective methods of contraception, of which 1 must be a physical barrier method (condom, diaphragm, or cervical/vault cap) until 6 months after the last dose of A-20502. Other effective forms of contraception include:

Permanent sterilization (hysterectomy and/or bilateral oophorectomy, or bilateral tubal ligation with surgery, or vasectomy) at least 6 months prior to Screening Women of childbearing potential who are on stable oral contraceptive therapy or intrauterine or implant device for at least 90 days prior to the study, or abstain from sexual intercourse as a way of living Phase 1b Inclusion Criteria are as Follows:

18) All Inclusion Criteria for Phase 1a (Exception: Inclusion Criterion #1).

19) Positive for B7-H4 expression in an archival or fresh tumor sample as evaluated by an accompanying validated central laboratory IHC assay.

20) History of other malignancy is permitted provided it has been definitively treated with no evidence of recurrence within the past 2 years (Exception: Definitively treated non-melanoma skin cancer, lobular cancer in situ, and cervical cancer in situ within 2 years are permitted).

Additional Cohort-Specific Inclusion Criteria for Phase 1b

Cohort 1bC1 Ovarian Cancer:

Histologically or cytologically confirmed diagnosis of recurrent epithelial ovarian, primary peritoneal, or fallopian tube carcinoma that is refractory to existing therapy(ies) known to provide clinical benefit Progressive disease on or after at least two prior regimens of treatment including at least one platinum-containing regimen, or unable to tolerate additional chemotherapy No prior therapy with an anti-PD1 or PD-L1 directed agent Cohort 1bC2 TNBC:

Histologically or cytologically confirmed metastatic TNBC.

At least two prior lines of systemic chemotherapy with at least one being administered in the metastatic setting No prior therapy with an anti-PD1 or PD-L1 directed agent Eligibility Criteria: Exclusion Criteria (Phase 1a and Phase 1b)

Patients who meet any of the following criteria may be excluded:

1) Immunosuppressive doses of systemic medications, such as steroids or absorbed topical steroids (doses ≥10 mg/day prednisone or equivalent daily) must be discontinued at least 2 weeks before the first dose of study drug. Short courses of high dose steroids, continuous low dose (prednisone <10 mg/day), inhaled, intranasal, intraocular, and joint injections of steroids are allowed.

2) Decreased cardiac function with New York Heart Association (NYHA)>Class 2 at screening.

3) Uncontrolled or significant heart disorder such as unstable angina

4) QT interval corrected for heart rate (QTc) per institutional guidelines >450 msec for males or >470 msec for females at screening.

5) History of anti-drug antibodies (ADAs), severe allergic, anaphylactic, or other infusion-related reaction to a previous biologic agent.

6) Known hypersensitivity to any component of the investigational product (IP) formulation and/or to pembrolizumab.

7) Vaccines (e.g., human papilloma virus [HPV] vaccine) within 4 weeks before the first dose of study drug. The inactivated seasonal influenza vaccine can be given to patients before treatment and while on therapy without restriction. Influenza vaccines containing live virus or other clinically indicated vaccinations for infectious diseases (i.e., pneumovax, varicella, etc.) may be permitted, but must be discussed with the Sponsor's Medical Monitor and may require a study drug washout period prior to and after administration of the vaccine.

8) Current unresolved infection or history of chronic, active, clinically significant infection (viral, bacterial, fungal, or other) which, in the opinion of the Investigator, would preclude the patient from exposure to a biologic agent or may pose a risk to patient safety.

9) Patients with abnormal serum chemistry values that in the opinion of the Investigator are considered to be clinically significant. This includes patients who show clinical signs and symptoms related to their abnormal serum chemistry values, as well as patients whose serum chemistry values are asymptomatic, but clinically significant according to the Investigator (e.g., hypokalemia or hyponatremia).

10) Any uncontrolled medical condition or psychiatric disorder which, in the opinion of the Investigator, would pose a risk to patient safety or interfere with study participation or interpretation of individual patient results.

11) Pregnant or breastfeeding.

12) Active, known, or suspected autoimmune disease requiring treatment in the past 2 years. Patients with Type I diabetes mellitus, hypothyroidism requiring only hormone replacement, skin disorders (such as vitiligo, psoriasis, or alopecia) not requiring systemic treatment, or conditions not expected to recur in the absence of an external trigger, are permitted to enroll.

13) Known history of testing positive for human immunodeficiency virus (HIV) 1 or 2 or known acquired immunodeficiency syndrome (AIDS).

14) Positive test for hepatitis B virus surface antigen (HBsAg) or detectable hepatitis C virus ribonucleic acid (HCV RNA) indicating acute or chronic infection.

15) Ongoing adverse effects from prior treatment >Grade 1 (with the exception of Grade 2 alopecia or peripheral neuropathy) based on National Cancer Institute (NCI) Common Terminology Criteria for Adverse Events (CTCAE).

16) Symptomatic interstitial lung disease or inflammatory pneumonitis.

17) Untreated or active CNS or leptomeningeal metastases. Patients are eligible if metastases have been treated and patients are neurologically returned to baseline or neurologically stable (except for residual signs or symptoms related to the CNS treatment) for at least 2 weeks before the first dose of study drug.

18) Evidence of coagulopathy or bleeding diathesis. Patients receiving stable therapeutic doses of anticoagulants will be permitted.

19) Transfusion of blood or platelets completed within 72 hours before the first dose of study drug.

20) Any uncontrolled inflammatory GI disease including Crohn's Disease and ulcerative colitis Tests and Observations: Safety assessments include vital signs, body weight, physical exam, ECOG score, laboratory tests (hematology, serum chemistries, and urinalysis), electrocardiograms (ECGs), and monitoring of adverse events (AEs) and concomitant medications.

Archival tumor tissue and consent to provide archival tumor (or willingness to undergo a fresh tumor biopsy during screening) will be collected for biomarker analysis to explore the relationship between baseline target levels, tumor immune phenotype and pharmacodynamic response.

Pre- and on-treatment tumor tissue may be collected for all patients in Phase 1a Dose Exploration and a subset of patients (up to 15 patients per cohort of 30 patients) in Phase 1b Dose Expansion for expanded pharmacodynamic analysis.

Efficacy assessments may consist of radiographic imaging performed every 6 weeks. Responses will be assessed according to RECIST v1.1.

Statistical Methods:

Efficacy Analysis

The ORR may be summarized by frequencies and percentages with 90% confidence interval (CI) by each dose/cohort. The duration of response (DOR) for complete response (CR) and partial response (PR) patients may be summarized with number of responders, number and percentage of event/censored, and Kaplan-Meier estimate of median DOR with 95% CI. Progression-free survival (PFS) for treated patients may be summarized with number and percentage of patients with PFS by each dose/cohort. PFS may also be summarized using Kaplan-Meier method with 95% CI. The ORR, DOR, and PFS may be determined using RECIST v1.1.

Pharmacokinetic Analysis

Individual and mean (±SD) serum A-20502 concentration-time data may be tabulated and plotted by dose level/cohort. PK parameters may be tabulated and summarized by dose level/cohort when appropriate and applicable. The impact of immunogenicity on A-20502 exposure may be assessed, tabulated, and summarized by dose level/cohort as data allow. Individual and mean (±SD) $C_{max}$ and $C_{trough}$ of pembrolizumab concentration-time data may be tabulated and plotted by cohort. PK parameters, such as accumulation ratio and attainment of steady state, may be tabulated and summarized by dose level/cohort if the data are available.

Immunogenicity Analysis

A baseline ADA-positive subject is defined as a subject who has an ADA positive sample at baseline. An ADA-positive subject is a subject with at least one ADA-positive sample relative to baseline after initiation of the treatment. The frequency distribution of baseline ADA-positive subjects and ADA-positive subjects after initiation of the treatment may be summarized for A-20502 and pembrolizumab, respectively.

Pharmacodynamic Analysis

Selected pharmacodynamic biomarkers will be assessed for meaningful changes between pretreatment and on-treatment tumor and peripheral blood samples.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of treating a solid tumor in a human subject, the method comprising administering to the subject (i) about 0.1 to about 20 mg/kg of an anti-B7-H4 antibody or antigen-binding fragment thereof that specifically binds to human B7-H4 and comprises a heavy chain variable region (VH) complementarity determining region (CDR) 1 comprising the amino acid sequence of SEQ ID NO:5, a VH CDR2 comprising the amino acid sequence of SEQ ID NO: 6, a VH CDR3 comprising the amino acid sequence of SEQ ID NO:7, a light chain variable region (VL) CDR1 comprising the amino acid sequence of SEQ ID NO:8, a VL CDR2 comprising the amino acid sequence of SEQ ID NO:9, and a VL CDR3 comprising the amino acid sequence of SEQ ID NO: 10; and (ii) about 200 mg of an anti-PD-1 antibody or antigen-binding fragment thereof comprising a VH CDR1 comprising the amino acid sequence of SEQ ID NO:34, a VH CDR2 comprising the amino acid sequence of SEQ ID NO:35, a VH CDR3 comprising the amino acid sequence of SEQ ID NO:36, a VL CDR1 comprising the amino acid sequence of SEQ ID NO: 37, a VL CDR2 comprising the amino acid sequence of SEQ ID NO:38, and a VL CDR3 comprising the amino acid sequence of SEQ ID NO:39.

2. The method of claim 1, wherein about 20 mg/kg of the anti-B7-H4 antibody or antigen-binding fragment thereof is administered to the subject.

3. The method of claim 1, wherein about 10 mg/kg of the anti-B7-H4 antibody or antigen-binding fragment thereof is administered to the subject.

4. The method of claim 1, wherein about 3 mg/kg of the anti-B7-H4 antibody or antigen-binding fragment thereof is administered to the subject.

5. The method of claim 1, wherein about 1 mg/kg of the anti-B7-H4 antibody or antigen-binding fragment thereof is administered to the subject.

6. The method of claim 1, wherein about 0.3 mg/kg of the anti-B7-H4 antibody or antigen-binding fragment thereof is administered to the subject.

7. The method of claim 1, wherein about 0.1 mg/kg of the anti-B7-H4 antibody or antigen-binding fragment thereof is administered to the subject.

8. The method of claim 1, wherein the anti-B7-H4 antibody or antigen-binding fragment thereof and the anti-PD-1 antibody or antigen-binding fragment thereof are administered concurrently.

9. The method of claim 1, wherein the anti-B7-H4 antibody or antigen-binding fragment thereof and the anti-PD-1 antibody or antigen-binding fragment thereof are administered sequentially.

10. The method of claim 1, wherein the anti-B7-H4 antibody or antigen-binding fragment thereof is administered about once every three weeks.

11. The method of claim 1, wherein the anti-PD-1 antibody or antigen-binding fragment thereof is administered about once every three weeks.

12. The method of claim 1, wherein the anti-B7-H4 antibody or antigen-binding fragment thereof and the anti-PD-1 antibody or antigen-binding fragment thereof are each administered about once every three weeks.

13. The method of claim 1, wherein the anti-B7-H4 antibody or antigen-binding fragment thereof comprises a VH comprising the amino acid sequence set forth in SEQ ID NO:11 and/or a VL comprising the amino acid sequence set forth in SEQ ID NO: 12.

14. The method of claim 1, wherein the anti-B7-H4 antibody or antigen-binding fragment thereof comprises a heavy chain constant region and/or a light chain constant region.

15. The method of claim 14, wherein the heavy chain constant region is a human immunoglobulin IgG1 heavy chain constant region and/or wherein the light chain constant region is a human immunoglobulin IgGκ light chain constant region.

16. The method of claim 1, wherein the anti-B7-H4 antibody or antigen-binding fragment thereof comprises a heavy chain constant region comprising the amino acid sequence set forth in SEQ ID NO:25 and/or a light chain constant region comprising the amino acid sequence set forth in SEQ ID NO:23.

17. The method of claim 1, wherein the anti-B7-H4 antibody or antigen-binding fragment thereof comprises a heavy chain comprising the amino acid sequence set forth in SEQ ID NO:21 and/or a light chain comprising the amino acid sequence set forth in SEQ ID NO:22.

18. The method of claim 1, wherein the anti-B7-H4 antibody or antigen-binding fragment thereof is a human antibody or antigen-binding fragment thereof.

19. The method of claim 1, wherein the anti-B7-H4 antibody or antigen-binding fragment thereof is a full length antibody.

20. The method of claim 1, wherein the anti-B7-H4 antibody or antigen-binding fragment thereof is an antigen-binding fragment.

21. The method of claim 20, wherein the antigen-binding fragment comprises a Fab, Fab', F(ab')$_2$, single chain Fv (scFv), disulfide linked Fv, V-NAR domain, IgNar, intra-body, IgGΔCH2, minibody, F(ab')$_3$, tetrabody, triabody, dia-body, single-domain antibody, DVD-Ig, Fcab, mAb$^2$, (scFv)$_2$, or scFv-Fc.

22. The method of claim 1, wherein the anti-PD-1 antibody or antigen-binding fragment thereof comprises a VH comprising the amino acid sequence of SEQ ID NO:32 and a VL comprising the amino acid sequence SEQ ID NO:33.

23. The method of claim 1, wherein the anti-PD-1 antibody or antigen-binding fragment thereof is pembrolizumab.

24. The method of claim 1, the method comprising administering to the subject (i) 3, 10 or 20 mg/kg of an anti-B7-H4 antibody or antigen-binding fragment thereof that specifically binds to human B7-H4 and comprises a VH comprising the amino acid sequence set forth in SEQ ID NO:11 and a VL comprising the amino acid sequence set forth in SEQ ID NO: 12, wherein the anti-B7-H4 antibody or antigen-binding fragment thereof is not detectably fucosylated; and (ii) 200 mg of pembrolizumab;

wherein (i) and (ii) are administered intravenously as separate formulations on the same day.

25. The method of claim 24, wherein the anti-B7-H4 antibody comprises a heavy chain comprising the amino acid sequence set forth in SEQ ID NO:21 and a light chain comprising the amino acid sequence set forth in SEQ ID NO:22.

26. The method of claim 1, the method comprising administering to the subject (i) about 20 mg/kg of an anti-B7-H4 antibody that spe-cifically binds to human B7-H4 and comprises a VH comprising the amino acid sequence of SEQ ID NO: 11 and a VL comprising the amino acid sequence of SEQ ID NO: 12; and (ii) about 200 mg of an anti-PD-1 antibody comprising a VH comprising the amino acid sequence of SEQ ID NO:32 and a VL comprising the amino acid sequence of SEQ ID NO:33, wherein the anti-B7-H4 antibody and the anti-PD-1 antibody are administered intrave-nously about once every three weeks.

27. The method of claim 26, wherein the anti-B7-H4 antibody comprises a heavy chain comprising the amino acid sequence set forth in SEQ ID NO: 21 and a light chain comprising the amino acid sequence set forth in SEQ ID NO:22.

28. The method of claim 26, wherein the anti-PD-1 antibody comprises a heavy chain comprising the amino acid sequence set forth in SEQ ID NO: 30 and a light chain comprising the amino acid sequence set forth in SEQ ID NO:31.

29. The method of claim 27, wherein the anti-PD-1 antibody comprises a heavy chain comprising the amino acid sequence set forth in SEQ ID NO: 30 and a light chain comprising the amino acid sequence set forth in SEQ ID NO:31.

30. The method of claim 1, wherein the solid tumor is selected from the group consisting of breast cancer, ductal carcinoma, endometrial carcinoma, ovarian cancer, urothe-lial cancer, non-small cell lung cancer, pancreatic cancer, thyroid cancer, kidney cancer and bladder cancer.

31. The method of claim 30, wherein the solid tumor is triple negative breast cancer.

32. The method of claim 30, wherein the solid tumor is a hormone-receptor (HR)-positive breast cancer.

33. The method of claim 30, wherein the non-small cell lung cancer is squamous cell carcinoma.

34. The method of claim 1, wherein the patient has not received prior therapy with a PD-1/PD-L1 antagonist.

35. The method of claim 1, wherein the method further comprises monitoring the number of immune cells in the tumor and/or monitoring cytokine levels in the subject.

36. The method of claim 1, wherein the anti-B7-H4 antibody or antigen-binding fragment thereof is present in a pharmaceutical composition comprising a pharmaceutically acceptable excipient, wherein at least 95% of the anti-B7-H4 antibodies or antigen-binding fragments thereof in the com-position are afucosylated.

37. The method of claim 36, wherein fucosylation of the anti-B7-H4 antibody or antigen-binding fragment thereof is undetectable in the composition.

38. The method of claim 36, the method comprising administering to the subject (a) a pharmaceutical composition comprising (i) anti-B7-H4 antibodies that specifically bind to human B7-H4 and comprise a VH comprising the amino acid sequence of SEQ ID NO: 11 and a VL comprising the amino acid sequence of SEQ ID NO: 12 and (ii) a pharmaceutically acceptable excipient, wherein at least 95% of the anti-B7-H4 antibodies thereof in the com-position are afucosylated, and wherein about 20 mg/kg of the antibodies are administered; and (b) a pharmaceutical composition comprising an anti-PD-1 antibody or antigen-binding fragment thereof comprising a VH comprising the amino acid sequence of SEQ ID NO:32 and a VL comprising the amino acid sequence of SEQ ID NO:33 and a pharmaceutically acceptable excipient, wherein about 200 mg of the antibody or antigen-binding fragment thereof is admin-istered, wherein (a) and (b) are administered intravenously about once every three weeks.

39. The method of claim 38, wherein the anti-B7-H4 antibodies comprise a heavy chain comprising the amino acid sequence set forth in SEQ ID NO: 21 and a light chain comprising the amino acid sequence set forth in SEQ ID NO:22.

40. The method of claim 38, wherein the anti-PD-1 antibody comprises a heavy chain comprising the amino acid sequence set forth in SEQ ID NO: 30 and a light chain comprising the amino acid sequence set forth in SEQ ID NO:31.

41. The method of claim 39, wherein the anti-PD-1 antibody comprises a heavy chain comprising the amino acid sequence set forth in SEQ ID NO: 30 and a light chain comprising the amino acid sequence set forth in SEQ ID NO:31.

* * * * *